United States Patent
Yang et al.

(10) Patent No.: US 10,016,137 B1
(45) Date of Patent: Jul. 10, 2018

(54) SYSTEM AND METHOD FOR SIMULTANEOUSLY DETECTING PHASE MODULATED OPTICAL SIGNALS

(71) Applicant: HI LLC, Los Angeles, CA (US)

(72) Inventors: Changhuei Yang, Pasadena, CA (US); Adam Marblestone, Arlington, MA (US); Jamu Alford, Simi Valley, CA (US); Daniel Sobek, Portola Valley, CA (US); Christian Wentz, Providence, RI (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 15/853,209

(22) Filed: Dec. 22, 2017

Related U.S. Application Data

(60) Provisional application No. 62/598,961, filed on Dec. 14, 2017, provisional application No. 62/596,446, (Continued)

(51) Int. Cl.
*A61B 5/00* (2006.01)
*A61B 5/1455* (2006.01)
(Continued)

(52) U.S. Cl.
CPC .......... *A61B 5/0097* (2013.01); *A61B 5/0042* (2013.01); *A61B 5/14553* (2013.01);
(Continued)

(58) Field of Classification Search
CPC ... A61B 5/0059; A61B 5/1455; A61B 5/1451; A61B 5/14552; A61B 5/14532;
(Continued)

(56) References Cited

U.S. PATENT DOCUMENTS

| 5,213,105 A | 5/1993 | Gratton et al. |
| 5,856,667 A | 1/1999 | Spirig et al. |

(Continued)

FOREIGN PATENT DOCUMENTS

| AU | 2009305257 B2 | 5/2014 |
| CN | 102176859 B | 1/2014 |

(Continued)

OTHER PUBLICATIONS

Atlan, M. et al., Pulsed acousto-optic imaging in dynamic scattering media with heterodyne parallel speckle detection, Optics Letters, vol. 30, No. 11, Jun. 1, 2005, 1360-1362.

(Continued)

*Primary Examiner* — Eric Winakur
*Assistant Examiner* — Chu Chuan (J J) Liu
(74) *Attorney, Agent, or Firm* — Michael J. Bolan; Vista IP Law Group, LLP

(57) ABSTRACT

An optical detection method and system are provided. Sample light is delivered into an anatomical structure having a target voxel, whereby a portion of the sample light passing through the target voxel is scattered by the anatomical structure as signal light, and another portion of the sample light not passing through the target voxel is scattered by the anatomical structure as background light that is combined with the signal light to create a sample light pattern. The sample light pattern and the reference light having an M number of different phases are concurrently combined to respectively generate an M number of interference light patterns. The M number of interference light patterns are detected. M pluralities of values representative of spatial components of the respective M number of interference light patterns are generated, and a physiologically-dependent optical parameter of the target voxel is determined based on the M pluralities of values.

30 Claims, 30 Drawing Sheets

Related U.S. Application Data filed on Dec. 8, 2017, provisional application No. 62/590,150, filed on Nov. 22, 2017.

(51) Int. Cl.
*H04N 5/225* (2006.01)
*H04N 5/89* (2006.01)

(52) U.S. Cl.
CPC .......... *A61B 5/4875* (2013.01); *A61B 5/6803* (2013.01); *H04N 5/2256* (2013.01); *H04N 5/2258* (2013.01); *A61B 2562/04* (2013.01); *A61B 2576/026* (2013.01); *H04N 5/89* (2013.01)

(58) Field of Classification Search
CPC ....... A61B 5/72; A61B 5/0066; A61B 5/0097; A61B 5/0042; A61B 5/14551; A61B 5/24532; A61B 5/14553; A61B 5/6803; A61B 5/4875
See application file for complete search history.

(56) References Cited

U.S. PATENT DOCUMENTS

| | | | |
|---|---|---|---|
| 6,041,248 A | 3/2000 | Wang | |
| 6,205,353 B1 | 3/2001 | Alfano et al. | |
| 6,334,699 B1 | 1/2002 | Gladnick | |
| 6,738,653 B1 | 5/2004 | Sfez et al. | |
| 6,777,659 B1 | 8/2004 | Schwarte | |
| 6,825,455 B1 | 11/2004 | Schwarte | |
| 6,957,096 B2 | 10/2005 | Sfez et al. | |
| 7,053,357 B2 | 5/2006 | Schwarte | |
| 7,060,957 B2 | 6/2006 | Lange et al. | |
| 7,119,906 B2 | 10/2006 | Pepper et al. | |
| 7,144,370 B2 | 12/2006 | Fomitchov | |
| 7,498,621 B2 | 3/2009 | Seitz | |
| 7,508,505 B2 | 3/2009 | Lustenberger et al. | |
| 7,515,948 B1 | 4/2009 | Balberg et al. | |
| 7,521,663 B2 | 4/2009 | Wäny | |
| 7,541,602 B2 | 6/2009 | Metzger et al. | |
| 7,560,701 B2 | 7/2009 | Oggier et al. | |
| 7,586,077 B2 | 9/2009 | Lehmann et al. | |
| 7,595,476 B2 | 9/2009 | Beer et al. | |
| 7,620,445 B2 | 11/2009 | Tsujita | |
| 7,622,704 B2 | 11/2009 | Wäny | |
| 7,647,830 B2 | 1/2010 | Sfez et al. | |
| 7,671,671 B2 | 3/2010 | Buettgen et al. | |
| 7,701,028 B2 | 4/2010 | Kaufmann et al. | |
| 7,733,742 B2 | 6/2010 | Gross et al. | |
| 7,747,301 B2 | 6/2010 | Cheng et al. | |
| 7,884,310 B2 | 2/2011 | Buettgen | |
| 7,889,257 B2 | 2/2011 | Oggier et al. | |
| 7,897,928 B2 | 3/2011 | Kaufmann et al. | |
| 7,898,649 B2 | 3/2011 | Masumura | |
| 7,917,312 B2 | 3/2011 | Wang et al. | |
| 7,923,673 B2 | 4/2011 | Büttgen et al. | |
| 8,017,858 B2 | 9/2011 | Mann | |
| 8,044,999 B2 | 10/2011 | Mullen et al. | |
| 8,103,329 B2 | 1/2012 | Fomitchov et al. | |
| 8,106,472 B2 | 1/2012 | Kaufmann et al. | |
| 8,108,022 B2 | 1/2012 | Balberg et al. | |
| 8,115,158 B2 | 2/2012 | Buettgen | |
| 8,126,524 B2 | 2/2012 | Balberg et al. | |
| 8,143,605 B2 | 3/2012 | Metzger et al. | |
| 8,223,215 B2 | 7/2012 | Oggier et al. | |
| 8,280,494 B2 | 10/2012 | Masumura | |
| 8,289,502 B2 | 10/2012 | Yoshida | |
| 8,299,504 B2 | 10/2012 | Seitz | |
| 8,315,483 B2 | 11/2012 | Shuster | |
| 8,326,567 B2 | 12/2012 | Masumura | |
| 8,336,391 B2 | 12/2012 | Rokni et al. | |
| 8,385,691 B2 | 2/2013 | Shuster | |
| 8,400,149 B2 | 3/2013 | Stoughton et al. | |
| 8,405,823 B2 | 3/2013 | Pfaff | |
| 8,423,116 B2 | 4/2013 | Balberg et al. | |
| 8,450,674 B2 | 5/2013 | Yang et al. | |
| 8,454,512 B2 | 6/2013 | Wang et al. | |
| 8,525,998 B2 | 9/2013 | Yaqoob et al. | |
| 8,562,658 B2 | 10/2013 | Shoham et al. | |
| 8,644,900 B2 | 2/2014 | Balberg et al. | |
| 8,717,574 B2 | 5/2014 | Yang et al. | |
| 8,754,939 B2 | 6/2014 | Oggier et al. | |
| 8,803,967 B2 | 8/2014 | Oggier et al. | |
| 8,817,255 B2 | 8/2014 | Masumura | |
| 8,830,573 B2 | 9/2014 | Cui et al. | |
| 8,867,798 B2 | 10/2014 | Shuster | |
| 8,917,442 B2 | 12/2014 | Baym et al. | |
| 8,922,759 B2 | 12/2014 | Gassert et al. | |
| 8,954,130 B2 | 2/2015 | Masumura | |
| 8,964,028 B2 | 2/2015 | Oggier | |
| 8,976,433 B2 | 3/2015 | Masumura | |
| 8,997,572 B2 | 4/2015 | Wang et al. | |
| 9,000,349 B1 | 4/2015 | Lehmann et al. | |
| 9,027,412 B2 | 5/2015 | Rokni et al. | |
| 9,046,338 B2 | 6/2015 | Boccara et al. | |
| 9,057,695 B2 | 6/2015 | Masumura | |
| 9,076,709 B2 | 7/2015 | Felber et al. | |
| 9,086,365 B2 | 7/2015 | Wang et al. | |
| 9,117,712 B1 | 8/2015 | Oggier et al. | |
| 9,131,170 B2 | 9/2015 | Mandelis et al. | |
| 9,131,880 B2 | 9/2015 | Balberg et al. | |
| 9,140,795 B2 | 9/2015 | Lehmann et al. | |
| 9,164,033 B2 | 10/2015 | Edwards et al. | |
| 9,209,327 B2 | 12/2015 | Neukom et al. | |
| 9,226,666 B2 | 1/2016 | Wang et al. | |
| 9,232,896 B2 | 1/2016 | Baym et al. | |
| 9,234,841 B2 | 1/2016 | Wang et al. | |
| 9,237,850 B2 | 1/2016 | Metzger et al. | |
| 9,282,931 B2 | 3/2016 | Tearney et al. | |
| 9,304,490 B2 | 4/2016 | Masumura | |
| 9,313,423 B2 | 4/2016 | Wang et al. | |
| 9,329,035 B2 | 5/2016 | Oggier | |
| 9,335,154 B2 | 5/2016 | Wax et al. | |
| 9,335,605 B2 | 5/2016 | Wang et al. | |
| 9,341,715 B2 | 5/2016 | Buettgen et al. | |
| 9,351,705 B2 | 5/2016 | Wang et al. | |
| 9,435,891 B2 | 9/2016 | Oggier | |
| 9,442,196 B2 | 9/2016 | Buettgen et al. | |
| 9,466,938 B2 | 10/2016 | Dupret et al. | |
| 9,486,128 B1 | 11/2016 | Hannaford et al. | |
| 9,488,573 B2 | 11/2016 | Edwards et al. | |
| 9,528,966 B2 | 12/2016 | Wang et al. | |
| 9,555,444 B2 | 1/2017 | Goodman et al. | |
| 9,619,486 B2 | 4/2017 | Shuster | |
| 9,655,527 B2 | 5/2017 | Wang et al. | |
| 9,668,672 B2 | 6/2017 | Zalevsky et al. | |
| 9,698,196 B2 | 7/2017 | Buettgen et al. | |
| 9,713,448 B2 | 7/2017 | Caplan et al. | |
| 9,720,505 B2 | 8/2017 | Gribetz et al. | |
| 9,730,649 B1 | 8/2017 | Jepsen | |
| 9,839,365 B1 | 12/2017 | Homyk et al. | |
| 2004/0080754 A1* | 4/2004 | Tobiason ........... | G01B 9/02056 356/495 |
| 2005/0085725 A1 | 4/2005 | Nagar et al. | |
| 2005/0256403 A1 | 11/2005 | Fomitchov | |
| 2006/0023621 A1 | 2/2006 | Hwang et al. | |
| 2006/0025659 A1* | 2/2006 | Kiguchi ............ | A61B 5/14532 600/316 |
| 2006/0063985 A1* | 3/2006 | Hogan ................ | A61B 5/0059 600/310 |
| 2006/0122475 A1 | 6/2006 | Balberg et al. | |
| 2006/0184042 A1 | 8/2006 | Wang et al. | |
| 2006/0184049 A1 | 8/2006 | Tsujita | |
| 2006/0224053 A1 | 10/2006 | Black et al. | |
| 2006/0247506 A1 | 11/2006 | Balberg et al. | |
| 2006/0253007 A1 | 11/2006 | Cheng et al. | |
| 2006/0264717 A1 | 11/2006 | Pesach et al. | |
| 2007/0093702 A1 | 4/2007 | Yu et al. | |
| 2008/0219584 A1 | 9/2008 | Mullen et al. | |
| 2008/0296514 A1 | 12/2008 | Metzger et al. | |
| 2008/0312533 A1 | 12/2008 | Balberg et al. | |
| 2009/0066949 A1 | 3/2009 | Masumura | |
| 2009/0069674 A1 | 3/2009 | Masumura et al. | |

(56) References Cited

U.S. PATENT DOCUMENTS

| | | | |
|---|---|---|---|
| 2009/0069676 | A1 | 3/2009 | Nishihara |
| 2009/0069685 | A1 | 3/2009 | Nishihara et al. |
| 2009/0069687 | A1 | 3/2009 | Igarashi |
| 2009/0124902 | A1 | 5/2009 | Herrmann |
| 2009/0171210 | A1 | 7/2009 | Wang |
| 2009/0253989 | A1 | 10/2009 | Caplan et al. |
| 2009/0264722 | A1 | 10/2009 | Metzger et al. |
| 2010/0000330 | A1 | 1/2010 | Rokni et al. |
| 2010/0069750 | A1 | 3/2010 | Masumura |
| 2010/0070233 | A1 | 3/2010 | Masumura |
| 2010/0073674 | A1 | 3/2010 | Yoshida |
| 2010/0152559 | A1 | 6/2010 | Cheng et al. |
| 2010/0152591 | A1 | 6/2010 | Yu et al. |
| 2010/0276573 | A1* | 11/2010 | Duerksen .............. G01J 1/4257 250/208.6 |
| 2010/0285518 | A1 | 11/2010 | Viator et al. |
| 2011/0071402 | A1 | 3/2011 | Masumura |
| 2011/0101241 | A1 | 5/2011 | Cattier et al. |
| 2011/0172513 | A1 | 7/2011 | Nakajima et al. |
| 2011/0228097 | A1 | 9/2011 | Motta |
| 2011/0237956 | A1 | 9/2011 | Edwards et al. |
| 2011/0249912 | A1 | 10/2011 | Shuster |
| 2012/0022381 | A1 | 1/2012 | Tearney et al. |
| 2012/0070817 | A1 | 3/2012 | Wang et al. |
| 2012/0127557 | A1 | 5/2012 | Masumura |
| 2012/0275262 | A1 | 11/2012 | Song et al. |
| 2014/0218748 | A1 | 8/2014 | Wax et al. |
| 2015/0238092 | A1 | 8/2015 | Masumura |
| 2015/0245771 | A1 | 9/2015 | Wang et al. |
| 2016/0187533 | A1 | 6/2016 | Maucec et al. |
| 2016/0235305 | A1 | 8/2016 | Wang et al. |
| 2016/0249812 | A1 | 9/2016 | Wang et al. |
| 2016/0299218 | A1 | 10/2016 | Lehmann |
| 2016/0305914 | A1 | 10/2016 | Wang et al. |
| 2017/0038000 | A1 | 2/2017 | Fuchsle et al. |
| 2017/0038300 | A1 | 2/2017 | Dake et al. |
| 2017/0038459 | A1 | 2/2017 | Kubacki et al. |
| 2017/0065182 | A1 | 3/2017 | Wang et al. |
| 2017/0090018 | A1 | 3/2017 | Buettgen et al. |
| 2017/0105636 | A1 | 4/2017 | Wang et al. |
| 2017/0122915 | A1 | 5/2017 | Vogt et al. |

FOREIGN PATENT DOCUMENTS

| | | |
|---|---|---|
| CN | 104107051 A | 10/2014 |
| CN | 104382558 A | 3/2015 |
| EP | 1 458 087 B1 | 10/2005 |
| EP | 1 771 844 | 4/2007 |
| EP | 2016891 A1 | 1/2009 |
| EP | 2036487 A2 | 3/2009 |
| EP | 2036488 A2 | 3/2009 |
| EP | 2036490 A1 | 3/2009 |
| EP | 2163189 A1 | 3/2010 |
| EP | 1675501 B1 | 9/2013 |
| EP | 1771882 B1 | 9/2013 |
| EP | 2240798 B1 | 8/2016 |
| EP | 2016891 B1 | 10/2016 |
| EP | 2594959 B1 | 1/2017 |
| EP | 2815251 B1 | 3/2017 |
| JP | 2009501581 A | 1/2009 |
| WO | WO2005025399 A2 | 3/2005 |
| WO | WO2005025399 A3 | 5/2005 |
| WO | 2006/025649 A1 | 3/2006 |
| WO | 2006/093666 A2 | 9/2006 |
| WO | WO2007035934 A2 | 3/2007 |
| WO | WO2008040771 A2 | 4/2008 |
| WO | WO2008040771 A3 | 8/2008 |
| WO | WO2010043851 A1 | 4/2010 |
| WO | WO2012080837 A2 | 6/2012 |
| WO | WO2012080838 A2 | 6/2012 |
| WO | WO2014106823 A2 | 7/2014 |
| WO | WO2016138637 A1 | 9/2016 |
| WO | WO2016193554 A1 | 12/2016 |

OTHER PUBLICATIONS

Choma, Michael A. et al., Instantaneous quadrature low-coherence interferometry with 3×3 fiber-optic couplers, Optic Letters, vol. 28, No. 22, Nov. 15, 2003, 2162-2164.

Hale, Thomas C. et al., Photorefractive optical lock-in vibration spectral measurement, Applied Optics, vol. 36, No. 31, Nov. 1, 1997, 8248-8258.

Khoury, Jehad et al., Photorefractive optical lock-in detector, Optics Letters, vol. 16, No. 18, Sep. 15, 1991, 1442-1444.

Li, Youzhi et al., Pulsed ultrasound-modulated optical tomography using spectral-hole burning as a narrowband spectral filter, Applied Physics Letter, 93, 011111 (2008).

Liu, Yan et al., Bit-efficient, sub-millisecond wavefront measurement using a lock-in camera for time-reversal based optical focusing inside scattering media, Opt. Lett. Apr. 1, 2016; 41(7): 1321-1324.

Liu, Yan et al., Lock-in camera based heterodyne holography for ultrasound-modulated optical tomography inside dynamic scattering media, Appl. Phys. Lett. 108, 231106 (2016).

Mao, Shu et al., Optical Lock-In Detection of FRET Using Synthetic and Genetically Encoded Optical Switches, Biophysical Journal, vol. 94, Jun. 2008, 4515-4524.

Marriott, Gerard et al., Optical lock-in detection imaging microscopy for contrast-enhanced imaging in living cells, PNAS, Nov. 18, 2008, vol. 105, No. 46, 17789-17794.

Ruan, Haowen et al., Pulsed ultrasound modulated optical tomography with harmonic lock-in holography detection, J. Opt. Soc. Am. A, vol. 30, No. 7, Jul. 2013, 1409-1416.

Strauss, Charlie E.M. et al., Synthetic-array heterodyne detection: a single-element detector acts as an array, Oct. 15, 1994, vol. 19, No. 20, Optics Letters, 1609-1611.

Tucker-Schwartz, Jason M. et al., Photothermal optical lock-in optical coherence tomography for in vivo imaging, Jun. 1, 2015, vol. 6, No. 6, DOI:10.1364/BOE.6.002268, Biomedical Optics Express, 2268-2282.

Yaqoob, Zahid et al., Harmonically-related diffraction gratings-based interferometer for quadrature phase measurements, Sep. 4, 2006, vol. 14, No. 18, Optics Express, 8127-8137.

Gratton, Gabriele et al., Dynamic brain imaging: Event-related optical signal (EROS) measures of the time course and localization of cognitive-related activity, Psychonomic Bulletin & Review, 1998, 5 (4), 535-563.

Matthews, Thomas E. et al., Deep tissue imaging using spectroscopic analysis of multiply scattered light, Optica, vol. 1, No. 2, Aug. 2014, 105-111.

Giacomelli, Michael G. et al., Imaging beyond the ballistic limit in coherence imaging using multiply scattered light, Optics Express, Feb. 28, 2011, vol. 19, No. 5, 4268-4279.

Puszka, Agathe et al., Time-resolved diffuse optical tomography using fast-gated single-photon avalanche diodes, Aug. 1, 2013, vol. 4, No. 8, DOI:10.1364/BOE4.001351, Biomedical Optics Express, 1351-1365.

Broussard GJ, Liang R, Tian L., Monitoring activity in neural circuits with genetically encoded indicators, Frontiers in molecular neuroscience, 2014;7.

Franceschini MA, Fantini S, Toronov V, Filiaci ME, Gratton E., "Cerebral hemodynamics measured by near-infrared spectroscopy at rest and during motor activation". In Proceedings of the Optical Society of America in Vivo Optical Imaging Workshop 2000 (pp. 73-80), Optical Society of America.

Franceschini, MA and Boas, DA, "Noninvasive Measurement of Neuronal Activity with Near-Infrared Optical Imaging," Neuroimage, vol. 21, No. 1, pp. 372-386 (Jan. 2004)).

Goense J, Merkle H, Logothetis NK, "High-resolution of fMRI reveals laminar differences in neurovascular coupling between positive and negative BOLD responses". Neuron, Nov. 8, 2012; 76(3):629-39.

Gratton G, Fabiani M., "Fast optical imaging of human brain function", Frontiers in human neuroscience, 2010;4.

Horinaka H, Osawa M. Hashimoto K, Wada K, Cho Y., "Extraction of quasi-straightforward-propagating photons from diffused light

(56) References Cited

OTHER PUBLICATIONS transmitting through a scattering medium by polarization modulation". Optics Letters, Jul. 1, 1995; 20(13):1501-3.

Horstmeyer R., Ruan H, Yang C, "Guidestar-Assisted Wavefront-Shaping Methods for Focusing Light into Biological Tissue," Nature Photonics, vol. 9, No. 9, pp. 563-571 (Sep. 1, 2015).

Laforest T, Verdant A, Dupret A, Gigan S., Ramaz F, Tessier G, "Co-Integration of a Smart CMOS Image Sensor and a Spatial Light Modulator for Real-Time Optical Phase Modulation," Proc. of SPIE-IS&T, vol. 2014, 9022:90220N-1 (Mar. 2014).

Leveque S, Boccara AC, Lebec M, Saint-Jalmes H, "Ultrasonic tagging of photon paths in scattering media: parallel speckle modulation processing". Optics Letters, Feb. 1, 1999; 24(3):181-3.

Liu Y, Ma C, Shen Y, Wang LV, "Bit-Efficient, Sub-Millisecond Wavefront Measurement Using a Lock-In Camera for Time-Reversal Based Optical Focusing Inside Scattering Media," Optics Letters, vol. 41, No. 7, pp. 1321-1324, Apr. 1, 2016.

Liu Y, Shen Y, Ma C, Shi J, Wang LV, "Lock-in Camera Based Heterodyne Holography for Ultrasound-Modulated Optical Tomography Inside Dynamic Scattering Media," Applied Physics Letters, vol. 108, No. 23, 231106, Jun. 6, 2016.

Mahan GD, Engler WE, Tiemann JJ, Uzgiris E, "Ultrasonic Tagging of Light: Theory," Proceedings of the National Academy of Sciences, vol. 95, No. 24, pp. 14015-14019, Nov. 24, 1998.

Patwardhan SV, Culver JP. Quantitative diffuse optical tomography for small animals using an ultrafast gated image intensifier. Journal of biomedical optics. Jan. 1, 2008; 13(1):011009.

Powell S., Srridge SR, Leung TS, "Gradient-Based Quantitative Image Reconstruction in Ultrasound-Modulated Optical Tomography: First Harmonic Measurement Type in a Linearized Diffusion Formulation," IEEE Transactions on Medical Imaging, vol. 35, No. 2, pp. 456-467 (Feb. 2016).

Qureshi MM, Brake J., Jeon HJ, Ruan H, Liu Y, Safi AM, Eom TJ, Yang C., Chung E, "In Vivo Study of Optical Speckle Decorrelation Time Across Depths in the Mouse Brain," Biomedical Optics Express, vol. 8, No. 11, pp. 4855-4864 (Nov. 1, 2017).

Sakadzic S, Wang LV, "High-Resolution Ultrasound-Modulated Optical Tomography in Biological Tissues," Optics Letters, vol. 29, No. 23, pp. 2770-2772, Dec. 1, 2004).

Schmitt, JM, Gandjbackhche, AH, Bonner RF, "Use of polarized light to discriminate short-part photons in a multiply scattering medium". Applied Optics, Oct. 20, 1992; 31(30):6535-46.

Steinbrink J, Villringer A, Kempf F, Haux D. Boden S, Obrig H., "Illuminating the BOLD Signal: Combined fMRI-fNIRS Studies," Magnetic Resonance Imaging, vol. 24, No. 4, pp. 495-505, May 31, 2006).

Van der Laan JD, Wright JB, Scrymgeour DA, Kemme SA, Dereniak EL, "Evolution of circular and linear polarization in scattering environments", Optics Express, Dec. 14, 2015; 23(25):31874-88.

Wang YM, Judkewitz B, DiMarzio CA, Yang C., "Deep-Tissue Focal Fluorescence Imaging with Digitally Time-Reversed Ultrasound-Encoded Light," Nature Communications, vol. 3, Article 928 (Jun. 16, 2012).

Wang, RK, Jacques SL, Ma Z, Hurst S, Hanson SR, Gruber A, Three dimensional optical angiography. Optics Express, Apr. 2, 2007; 15(7):4083-97.

Xu X, Liu H., Wang LV, "Time-Reversed Ultrasonically Encoded Optical Focusing into Scattering Media," Nature Photonics, vol. 5, No. 3, pp. 154-157 (Mar. 1, 2011).

* cited by examiner

SYSTEM AND METHOD FOR SIMULTANEOUSLY DETECTING PHASE MODULATED OPTICAL SIGNALS

RELATED APPLICATION DATA

Pursuant to 35 U.S.C. § 119(e), this application claims the benefit of U.S. Provisional Patent Application 62/590,150, filed Nov. 22, 2017, U.S. Provisional Patent Application 62/596,446, filed Dec. 8, 2017, and U.S. Provisional Patent Application 62/598,961, filed Dec. 14, 2017, which are expressly incorporated herein by reference. This application is also related to U.S. patent application Ser. Nos. 15/844, 370, 15/844,398, and 15/844,411, all filed on Dec. 15, 2017, which are expressly incorporated herein by reference.

FIELD OF THE INVENTION

The present invention relates to methods and systems for non-invasive measurements in the human body, and in particular, methods and systems related to detecting physiologically dependent optical parameters in the human body.

BACKGROUND OF THE INVENTION

Measuring neural activity in the brain is useful for medical diagnostics, neuromodulation therapies, neuroengineering, or brain-computer interfacing. For example, it may be desirable to measure neural activity in the brain of a patient to determine if a particular region of the brain has been impacted by reduced blood irrigation, a hemorrhage, any other type of damage. For instance, in cases where the patient has suffered a traumatic brain injury, such as stroke, it may be desirable to determine whether the patient should undergo a therapeutic procedure. Measuring neural activity in the brain also may be used to determine the efficacy of such a therapeutic procedure.

Conventional methods for measuring neural activity in the brain include diffuse optical tomography (DOT), and functional near-infrared spectroscopy (fNIRS), as well as others. These applications only employ a moderate amount of near-infrared or visible light radiation, thus being comparatively safe and gentle for a biological subject in comparison to X-Ray Computed Tomography (CT) scans, positron emission tomography (PET), or other methods that use higher-energy and potentially harmful radiation. Moreover, in contrast to methods, such as functional magnetic resonance imaging (fMRI), these optically-based imaging methods do not require large magnets or magnetic shielding, and thus, can be scaled to wearable or portable form factors, which is especially important in applications such as brain-computer interfacing.

Because DOT and fNIRS rely on light, which scatters many times inside brain, skull, dura, pia, and skin tissues, the light paths occurring in these techniques comprise random or "diffusive" walks, and therefore, only limited spatial resolution can be obtained by a conventional optical detector, often on the order of centimeters. The reason for this limited spatial resolution is that the paths of photons striking the detector in such schemes are highly variable and difficult, and even impossible to predict without detailed microscopic knowledge of the scattering characteristics of the brain volume of interest, which is typically unavailable in practice (i.e., in the setting of non-invasive measurements through skull for brain imaging and brain interfacing). In summary, light scattering prevents optical imaging from achieving high resolution deep inside tissue.

There is an increasing interest in ultrasound modulated optical tomography (UOT) to detect more precisely localized changes in biological tissues, e.g., on a sub-millimeter length scale, inside thick biological tissue, such as the brain (see U.S. Pat. No. 8,423,116; Sakadzic S, Wang L V, "High-Resolution Ultrasound-Modulated Optical Tomography in Biological Tissues," Optics Letters, Vol. 29, No. 23, pp. 2770-2772, Dec. 1, 2004). These localized changes may include changes in light absorption in the brain that reflect neural activity and neurovascular coupling, such as a blood-oxygen-level dependent signal, for application in diagnostics, therapeutics, or, notably, brain computer interfacing (see Steinbrink J, Villringer A, Kempf F, Haux D. Boden S, Obrig H., "Illuminating the BOLD Signal: Combined fMRI-fNIRS Studies," Magnetic Resonance Imaging, Vol. 24, No. 4, pp. 495-505, May 31, 2006). Thus, there is an increasing interest in ultrasound modulated optical tomography (UOT) in biomedical applications due to its potential to simultaneously achieve good resolution and imaging depth.

In UOT, a highly localized ultrasound focus, e.g., millimeter or sub-millimeter in size, is used to selectively perturb (i.e., "tag") light (e.g., light generated by a near-infrared coherent laser) passing through a voxel size of tissue defined by the size of the ultrasound focus. Due to the acousto-optic effect, light passing through the ultrasonic beam undergoes a frequency shift defined by multiples of the ultrasonic frequency. By detecting the frequency-shifted light, i.e., the tagged light, spatial information characterizing the biological tissue within the voxel can be acquired. As a result, spatial resolution is boosted from the centimeter-scale diffusive spread of light in the biological tissue to approximately a millimeter-scale voxel size. This ultrasound tagging of light relies on mechanisms known in the field (see Mahan G D, Engler W E, Tiemann J J, Uzgiris E, "Ultrasonic Tagging of Light: Theory," Proceedings of the National Academy of Sciences, Vol. 95, No. 24, pp. 14015-14019, Nov. 24, 1998).

Typical UOT implementations generate weak signals that make it difficult to differentiate ultrasound-tagged light passing through the focal voxel from a much larger amount of unmodulated light which is measured as DC shot noise. Thus, conventional UOT has the challenge of obtaining optical information through several centimeters of biological tissue, for example, noninvasive measurements through the human skull used to measure functional changes in the brain.

Various methods have been developed to detect the very small fraction of tagged light out of a large background of untagged light by detecting the speckle pattern of light resulting from the interference of many multiply-scattered optical waves with different phases and amplitudes, which combine in a resultant wave whose amplitude, and therefore intensity, as well as phase, varies randomly. In the context of neuroengineering and brain computer interfacing, a key challenge is to render these methods to be sufficiently sensitive to be useful for through-human-skull functional neuroimaging.

One technique uses a narrow spectral filter to separate out the untagged light striking a single-pixel detector, and is immune to "speckle decorrelation" (greater than ~0.1 ms-1 ms) due to the scatters' motion (for example, blood flow) inside living biological tissue, but requires bulky and expensive equipment.

Another technique uses crystal-based holography to combine a reference light beam and the sample light beam into a constructive interference pattern, but can be adversely affected by rapid speckle decorrelation, since the response time of the crystal is usually much longer than the speckle correlation time.

Still another technique, referred to as heterodyne parallel speckle detection (PSD), employs optical interference together with a spatially resolved detector array (e.g., a conventional charge-coupled device (CCD) camera) used as an array of independent detectors for collecting the signal over a large number of coherence areas (see Atlan M, Forget B C, Ramaz F, Boccara A C, Gross M, "Pulsed Acousto-Optic Imaging in Dynamic Scattering Media With Heterodyne Parallel Speckle Detection," Optics Letter, Vol. 30, No. 11, pp. 1360-1362, Jun. 1, 2005). Such configuration improves the signal-to-noise ratio relative to a single-detector and relative to approaches based on other modes of separating tagged and untagged light, such as spectral filters. However, the conventional CCD cameras used for heterodyne PSD have low frame rates, and therefore suffer from a relatively low speed relative to the speckle decorrelation time, thereby making this set up insufficient for in vivo deep tissue applications. Furthermore, conventional CCD cameras record both the AC signal and the DC background for each pixel. Thus, only a few bits of a pixel value can be used to represent the useful AC signal, while most of the bits are wasted in representing the DC background, resulting in a low efficiency in the use of bits.

Besides the challenges posed by the signal-to-noise ratio, speckle decorrelation time, and efficient pixel bit processing, another challenge involves obtaining sufficient axial resolution (i.e., the depth resolution or ultrasound propagation direction). To address this challenge, UOT has been applied in a pulsed wave (PW) mode for heterodyne PSD, rather than a continuous (CW) mode (see Li Y Zhang H, Kim C, Wagner K H, Hemmer P., Wang L V, "Pulsed Ultrasound-Modulated Optical Tomography Using Spectral-Hole Burning as a Narrowband Spectral Filter," Applied Physics Letters, Vol. 93, No. 1, 011111, Jul. 7, 2008; Ruan H, Mather M L, Morgan S P, "Pulsed Ultrasound Modulated Optical Tomography with Harmonic Lock-In Holography Detection," JOSA A, Vol. 30, No. 7, pp. 1409-1416, Jul. 1, 2013).

PW UOT has the benefit of enabling improved axial resolution compared to CW UOT. That is, with CW UOT, any light passing through the tissue, even though outside of the focal voxel, may be inadvertently tagged by the continuously propagating ultrasound energy along the ultrasound axis, thereby decreasing the signal-to-noise ratio. With PW UOT, the light passing through the tissue is pulsed only when the ultrasound pulses travels through the focal voxel, such that light outside of the focal voxel will not be tagged by the ultrasound energy. Although PW UOT improves axial resolution, the pulsed UOT signals are weak relative to continuous UOT signals.

Lock-in cameras, as compared to conventional CCD cameras, have been used to demodulate frequency-encoded light signals, e.g., to selectively extract ultrasound-modulated light from a light field consisting of a combination of ultrasound-modulated and unmodulated light, which has been theorized in ultrasound modulated optical tomography (UOT) (see Liu Y, Shen Y, Ma C, Shi J, Wang L V, "Lock-in Camera Based Heterodyne Holography for Ultrasound-Modulated Optical Tomography Inside Dynamic Scattering Media," Applied Physics Letters, Vol. 108, No. 23, 231106, Jun. 6, 2016), and digital optical phase conjugation (DOPC) (see Liu Y, Ma C, Shen Y, Wang L V, "Bit-Efficient, Sub-Millisecond Wavefront Measurement Using a Lock-In Camera for Time-Reversal Based Optical Focusing Inside Scattering Media," Optics Letters, Vol. 41, No. 7, pp. 1321-1324, Apr. 1, 2016).

A "lock-in camera" can be defined as a form of digital camera that can rapidly sample and store changes in a light field, in precise temporal synchrony with an external trigger signal, and which may also perform on-chip computations on the stored samples. The key feature of lock-in cameras is the ability to rapidly capture and store multiple sequential samples of the light field, which sample-to-sample latencies shorter than readout times of conventional cameras. Essentially, lock-in cameras capture and store, at each pixel multiple captured intensity values taken in short succession, with each captured intensity value stored in a separate "bin," rather than storing only a single captured intensity value as in conventional cameras. This enables lock-in cameras, for example, to sample a modulated light field at the same frequency as the modulation, such that subtraction across successive samples, or other operations, such as quadrature detection, will extract the component of the light that is modulated at the modulation frequency, while subtracting off the unmodulated ("DC") background. Similarly, lock-in cameras can be used to make a series of such measurements or comparisons, locked to an external trigger signal, rapidly in order to extract such modulated components from a rapidly changing light field arising from dynamic, disordered biological specimen.

The use of lock-in cameras for measurement and demodulation of modulated light fields has, however, a number of disadvantages, particularly in the context of rapid measurement signals from dynamic, strongly scattering biological tissues. First, lock-in cameras cannot sample a light field arbitrarily fast, and therefore, have a minimum latency between the bins. Second, lock-in cameras have only achieved limited scale to date, e.g., less than 100,000 pixels (e.g., the Heliotis Helicam C3), and do not have the large industrial support base of the conventional camera industry (e.g., with a digital camera that is now included within every smart phone). Third, lock-in cameras support only a limited number of "bins" per pixel (currently, four bins per pixel) due to limitations on pixel area and photodetector fill factor, and thus, support only a limited number of temporal samples in the lock-in detection process.

The first of these disadvantages, in particular the limited sampling speed, poses a key challenge for the use of lock-in cameras to support imaging deep inside dynamic, highly scattering biological tissues, such as the human skull and brain. In particular, in the setting of UOT of a dynamic, highly scattering biological tissue using lock-in detection, a series of multiple lock-in camera detection events (bins) must be acquired within the "speckle decorrelation time" of the biological medium, which rapidly decreases with the depth at which the tissue is to be imaged, falling to microseconds or below as the imaging depth extends to the multi-centimeter range, and scaling inversely as the square of the imaging depth into tissue. This poses an obstacle for lock-in camera based detection, since the speed of lock-in cameras is limited.

Thus, although the UOT schemes described above may be sufficient for certain applications, particularly when using lock-in cameras, such UOT schemes are inappropriate for the application of 3D-resolved, highly sensitive detection of small signals (e.g., blood-oxygen-level dependent signals) non-invasively through thick scattering layers, such as the human skull.

SUMMARY OF THE INVENTION

In accordance with a first aspect of the present inventions, a non-invasive optical detection system comprises an interferometer configured for delivering sample light into the anatomical structure having a target voxel (e.g., brain matter), whereby a portion of the sample light passing through the target voxel is scattered by the anatomical structure as signal light, and another portion of the sample light not passing through the target voxel is scattered by the anatomical structure as background light that is combined with the signal light to create a sample light pattern. The interferometer is further configured for concurrently combining the sample light pattern and reference light having an M number of different phases relative to the sample light pattern, to respectively generate an M number of interference light patterns. In one embodiment, M equals 2, and the different phases are 0 and $\pi$. In another embodiment, M equals 4, and the different phases are 0, $\pi/2$, $\pi$, and $3\pi/2$.

In one embodiment, the interferometer comprises at least one beam splitter/combiner configured for splitting the reference light respectively into the M number of different phases, and concurrently combining the sample light pattern and the reference light having the M number of different phases to respectively generate the M number of interference light patterns. If M equals two, the beam splitter/combiner(s) may comprise a single beam splitter/combiner configured for splitting the reference light respectively into two of the different phases, and concurrently combining the sample light pattern and the reference light having the two different phases to respectively generate the two interference light patterns.

In another embodiment, the interferometer comprises at least one beam splitter configured for splitting the sample light pattern into an M number of sample light pattern portions, in which case, the interferometer may be configured for concurrently combining the sample light pattern and the reference light having the M number of different phases by respectively combining the M number of sample light pattern portions and the reference light having the M number of different phases. If M equals four, the beam splitter(s) may comprise a single beam splitter configured for splitting the sample light pattern into first and second sample light pattern portions. The beam splitter/combiner(s) may comprise a first beam splitter/combiner configured for splitting the reference light respectively into a first two of the four different phases, and concurrently combining the first sample light portion and the reference light having the first two of the four different phases to respectively generate the first two of the four interference light patterns; and further comprise a second beam splitter/combiner configured for splitting the reference light respectively into a second two of the four different phases, and concurrently combining the second sample light pattern portion and the reference light having the second two of the four different phases to respectively generate the second two of the four interference light patterns. The first two of the four different phases and the second two of the four different phases may be ninety degrees out of phase with each other.

The optical detection system further comprises a camera system having an M number of optically registered detector arrays respectively configured for detecting the M number of interference light patterns, and generating M pluralities of values representative of spatial components of the respective M number of interference light patterns. Each of the interference light patterns may comprise a light speckle pattern, in which case, the spatial components may comprise speckle grains of the light speckle pattern.

The M number of detector arrays may, e.g., be mechanically disposed on separate camera microchips, or may be mechanically integrated together on a single camera microchip. The optical detection assembly further comprises a processor configured for determining a physiologically-dependent optical parameter of the target voxel (e.g., the level of deoxygenated and/or oxygenated hemoglobin concentration or relative abundance or the level of water concentration or relative water concentration of brain matter) based on the M pluralities of values. The processor may be configured for computing the amplitude of the signal light using the plurality of values generated by each detector array, and determining the physiologically-dependent optical parameter of the target voxel based on the computed amplitude of the signal light. If the plurality of values are generated by each detector array are intensities of the spatial components of the respective interference light pattern, the processor may be configured for using the plurality of values generated by each detector array to determine a product of the amplitude of the signal light and a known amplitude of the reference light, and determining the amplitude of the signal light from the determined product. The processor may optionally be configured for determining neural activity within the target voxel based on the determined physiologically-dependent optical parameter.

In one embodiment, the optical detection assembly further comprises processing circuitry integrated within the single camera microchip. In this case, the processing circuitry may be configured for performing an arithmetic function on the M pluralities of values (e.g., a sum of the absolute differences between corresponding values of the M pluralities of values), and outputting at least one value, and the processor is configured for determining the physiologically-dependent optical parameter of the target voxel based on the value(s). In another embodiment, M equals two, and the two detector arrays are respectively mechanically integrated on opposite sides of the single camera microchip.

In still another embodiment, the interferometer comprises at least one array of beam splitter/combiners integrated within the single camera microchip. In this case, the arrays of beam splitter/combiners may be configured for splitting the reference light respectively into the M number of different phases, and concurrently combining the sample light pattern and the reference light having the M number of different phases to respectively generate the M number of interference light patterns. The M number of detector arrays may be interlaced with each other on the single camera microchip. The single camera microchip may further comprise an array of reference input ports and an array of sample input ports, the interferometer may further a first grate configured for transforming the reference light into an array of reference beamlets, a first lens configured for focusing the array of reference beamlets into the array of reference input ports, a second grate configured for transforming the sample light pattern into an array of sample light pattern beamlets, and a second lens configured for focusing the array of sample light pattern beamlets into the array of sample input ports. The array(s) of beam splitter/combiners may be configured for splitting the array of reference beamlets respectively into the M number of different phases, and concurrently combining the array of sample light pattern beamlets to and the array of reference beamlets having the M number of different phases to respectively generate the M number of interference light patterns.

The signal light may, e.g., be frequency encoded or path-length encoded. If frequency encoded, the optical detection system may further comprise an acoustic assembly configured for delivering ultrasound into the target voxel, such that the signal light is frequency shifted by the ultrasound, and a controller configured for operating the acoustic assembly and the interferometer to pulse the ultrasound and the sample light in synchrony, such that only the signal light is frequency shifted by the ultrasound. The controller may be configured for operating the acoustic assembly and the interferometer to pulse the ultrasound and the sample light in synchrony, such that only a single pulse of the sample light is delivered into the anatomical structure for each pulse of the ultrasound delivered into the target voxel. The interferometer may be configured for combining the signal light and the reference light in a homodyne manner. The interferometer may be further configured for frequency shifting the sample light by the frequency of the ultrasound, such that the signal light and the reference light are combined in the homodyne manner.

In accordance with a second aspect of the present inventions, a non-invasive optical detection method comprises delivering sample light into the anatomical structure having a target voxel (e.g., brain matter), whereby a portion of the sample light passing through the target voxel is scattered by the anatomical structure as signal light, and another portion of the sample light not passing through the target voxel is scattered by the anatomical structure as background light that is combined with the signal light to create a sample light pattern.

The method further comprises concurrently combining the sample light pattern and reference light having an M number of different phases relative to the sample light pattern, to respectively generate an M number of interference light patterns. In one method, M equals 2, and the different phases are 0 and $\pi$. In another method, M equals 4, and the different phases are 0, $\pi/2$, $\pi$, and $3\pi/2$.

One method further comprises splitting the reference light respectively into the M number of different phases, and concurrently combining the sample light pattern and the reference light having the M number of different phases to respectively generate the M number of interference light patterns. If M equals two, the method may comprise splitting the reference light respectively into two of the different phases, and concurrently combining the sample light pattern and the reference light having the two different phases to respectively generate the two interference light patterns.

Another method further comprises splitting the sample light pattern into an M number of sample light pattern portions, in which case, the method may further comprises concurrently combining the sample light pattern and the reference light having the M number of different phases by respectively combining the M number of sample light pattern portions and the reference light having the M number of different phases. If M equals four, the method may further comprise splitting the sample light pattern into first and second sample light pattern portions, splitting the reference light respectively into a first two of the four different phases, concurrently combining the first sample light portion and the reference light having the first two of the four different phases to respectively generate the first two of the four interference light patterns, splitting the reference light respectively into a second two of the four different phases, concurrently combining the second sample light pattern portion and the reference light having the second two of the four different phases to respectively generate the second two of the four interference light patterns. The first two of the four different phases and the second two of the four different phases may be ninety degrees out of phase with each other.

The method further comprises detecting the M number of interference light patterns, and generating M pluralities of values representative of spatial components of the respective M number of interference light patterns. Each of the interference light patterns may comprise a light speckle pattern, in which case, the spatial components may comprise speckle grains of the light speckle pattern.

The method further comprises determining a physiologically-dependent optical parameter of the target voxel (e.g., the level of deoxygenated and/or oxygenated hemoglobin concentration or relative abundance or the level of water concentration or relative water concentration of brain matter) based on the M pluralities of values. One method may further comprise computing the amplitude of the signal light using the plurality of values generated by each detector array, and determining the physiologically-dependent optical parameter of the target voxel based on the computed amplitude of the signal light. If the plurality of values are generated by each detector array are intensities of the spatial components of the respective interference light pattern, the plurality of values generated by each detector array may be used to determine a product of the amplitude of the signal light and a known amplitude of the reference light, and determining the amplitude of the signal light from the determined product. An optional method further comprises determining neural activity within the target voxel based on the determined physiologically-dependent optical parameter.

The signal light may, e.g., be frequency encoded or path-length encoded. If frequency encoded, the method may further comprise delivering ultrasound into the target voxel, such that the signal light is frequency shifted by the ultrasound, and pulsing the ultrasound and the sample light in synchrony, such that only the signal light is frequency shifted by the ultrasound. The ultrasound and the sample light may be pulsed in synchrony, such that only a single pulse of the sample light is delivered into the anatomical structure for each pulse of the ultrasound delivered into the target voxel. The method may further comprise combining the signal light and the reference light in a homodyne manner, e.g., by frequency shifting the sample light by the frequency of the ultrasound, such that the signal light and the reference light are combined in the homodyne manner.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The ultrasound modulated optical tomography (UOT) systems described herein utilize the combination of a pulsed ultrasound sequence that tags light propagating through an anatomical structure, and a selective lock-in camera that detects the tagged light (e.g., via parallel speckle detection (PSD)), as opposed to a conventional camera, to provide a highly efficient and scalable scheme that enables detection of highly localized and high spatial resolution UOT signals (e.g., blood-oxygen level dependent signals) at great depth inside a biological specimen, e.g., noninvasively through the entire thickness of the human skull and into the underlying cerebral cortical brain matter. The UOT systems may utilize a specific homodyne interference scheme that enables shot noise limited detection of the signal light. Such UOT signals may be used for, e.g., brain-computer interfacing, medical diagnostics, or medical therapeutics. Although the UOT systems are described herein as being used to image brain tissue for exemplary purposes, such UOT system can be used to image other anatomical parts of the body.

Figure 1:
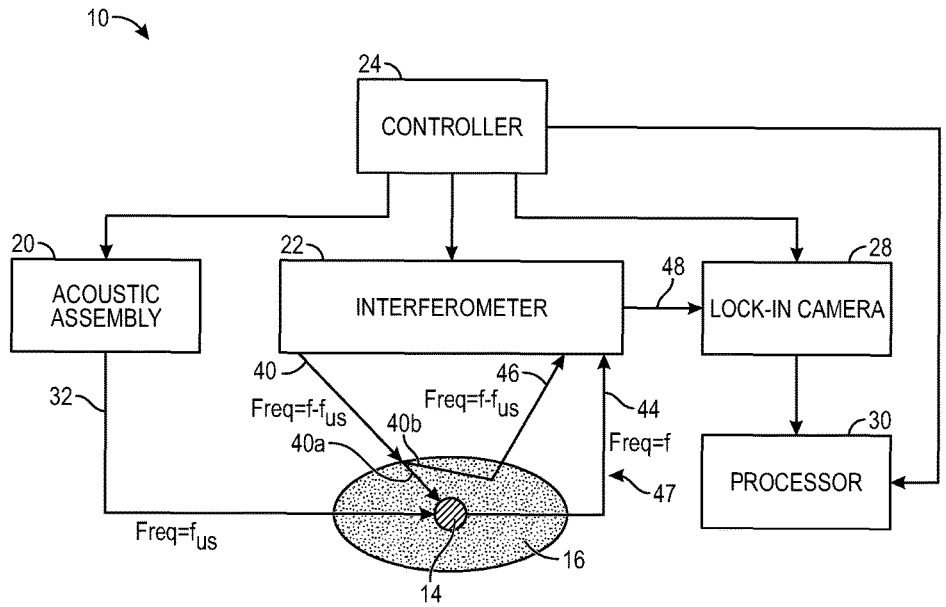
FIG. 1 is a block diagram of an ultrasound modulating optical tomography (UOT) system constructed in accordance with one embodiment of the present inventions.

Referring to FIG. 1, an ultrasound modulated optical tomography (UOT) system 10 constructed in accordance with one embodiment of the present inventions will be described. The UOT system 10 is designed to non-invasively measure a physiologically-dependent optical parameter of a target voxel 14 in an anatomical structure 16. In the illustrated embodiment, the anatomical structure 16 is the intact head of a patient 18 (shown in FIG. 12), including the scalp, skull, and brain, with the target voxel 14 being a portion of the brain. In a practical implementation, the UOT system 10 will acquire data from multiple target voxels 14 ("data voxels") spatially separated from each other within a volume of interest (not shown). A "target voxel" may be defined as a small contiguous sub-volume of space (e.g., a cube) within the anatomical structure 16. For purposes of brevity, the UOT system 10 will be described as acquiring one data voxel (i.e., data representative of a physiologically-dependent optical parameter of the target voxel 14), although it should be understood that the UOT system 10 may be capable of acquiring more than one data voxel from the volume of interest of the anatomical structure 16.

In the illustrated embodiment, the physiologically-dependent optical parameter may be, e.g., a level of deoxygenated and/or oxygenated hemoglobin concentration or relative abundance, although in other embodiments, the physiologically-dependent optical parameter can be any parameter that varies in accordance with a change in an optical property of the target voxel 14 (e.g., light absorption). The physiologically-dependent optical parameters may alternatively comprise an analyte concentration in the blood, analyte/metabolite in tissue, concentration of a substance (e.g., blood, hemoglobin) or a structure within tissue, the presence and concentration of lamellar bodies in amniotic fluid for determining the level of lung maturity of a fetus, the presence and/or concentration of meconium in the amniotic fluid, optical properties of other extravascular fluids, such as pleural, pericardial, peritoneal, and synovial fluids. The physiologically-dependent optical parameter may be used internally within the UOT system 10 or may be transmitted to external devices for use therein, e.g., medical devices, entertainment devices, neuromodulation stimulation devices, alarm systems, video games, etc.

The UOT system 10 generally includes an acoustic assembly 20, an interferometer 22, a controller 24, a lock-in camera 28, and a processor 30.

The acoustic assembly 20 is configured for delivering ultrasound 32 into the target voxel 14. Preferably, the acoustic assembly 20 focuses the ultrasound 32 on this target voxel 14 in order to maximize the imaging resolution of the UOT system 10; that is, the more focused the ultrasound 32 is, the smaller the target voxel 14 may be defined, thereby increasing the resolution of the UOT system 10.

Preferably, the frequency $f_{us}$ of the ultrasound 32 is selected (e.g., in the range of 100 KHz-10 MHz), such that the ultrasound 32 can pass efficiently through the skull and brain matter without significant attenuation that would otherwise cause insufficient ultrasound pressure at the target voxel 14, so that detectable UOT modulation of the light is created, as described in further detail below. It should be appreciated that the wavelength of such ultrasound in brain matter, given that the speed of sound in brain matter is similar to that of water (1500 meter/second), is on the order of fractions of a millimeter to a few millimeters. Thus, the acoustic assembly 20 may obtain ultrasound focal confinement at the target voxel 14 laterally on the order of the wavelength of the ultrasound 32 (e.g., less than 1 mm), and axially on the order of the wavelength of the ultrasound 32 when the acoustic assembly 20 is operated to pulse the ultrasound 32 at short durations (e.g., a single cycle), as will be described in further detail below.

Figure 2:
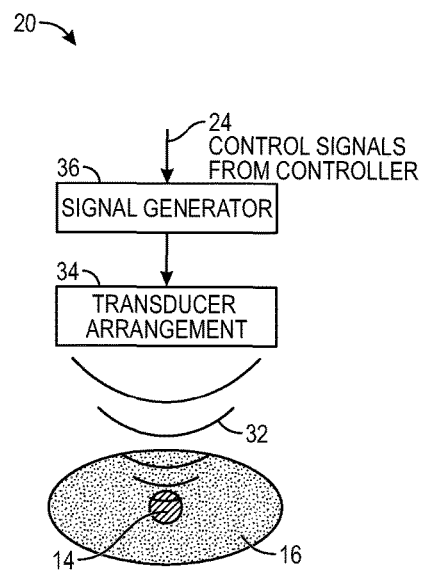
FIG. 2 a block diagram of one embodiment of an acoustic assembly used in the UOT system of FIG. 1.

Referring further to FIG. 2, one embodiment of the acoustic assembly 20 includes an ultrasound transducer arrangement 34 and a signal generator 36. The ultrasound transducer arrangement 32 may take the form of any device that emits ultrasound 32 (in the illustrated embodiment, focused ultrasound) at a defined frequency and duration in response to a controlled drive signal; for example, signal acoustic element configured for emitting ultrasound beams with a fixed focus; or a piezoelectric phased array capable of emitting ultrasound beams with variable direction, focus, duration, and phase, or may be an array of pressure generating units (e.g., silicon, piezoelectric, polymer or other units), an ultrasound imaging probe, or even an array of laser generated ultrasound (LGU) elements.

The signal generator 36 is configured for generating alternating current (AC) signals for driving the ultrasound transducer arrangement 34 at a defined ultrasound frequency, duration, and intensity. The AC drive signal may be electrical or optical, depending on the nature of the ultrasound transducer arrangement. The signal generator 36 includes control inputs (not shown) for receiving control signals from the controller 24 that cause the ultrasound transducer arrangement 34 to emit the ultrasound 32 at a selected time, duration, and intensity. Thus, as will be described in further detail below, the controller 24 may selectively pulse the ultrasound 32.

In one particular embodiment, the transducer arrangement 34 is a head-mounted steerable ultrasonic array coupled to the skin of the patient via hydrogel or other means of mechanical coupling in order to effectively launch the ultrasound 32 towards the precisely defined target voxel 14 within the anatomical structure 16, and in this case, the three-dimensional volume of the brain, while compensating the ultrasound wavefront using well-known phased array techniques to achieve efficient and selective ultrasound delivery to the target voxel 14.

Referring to FIGS. 1 and 3, the interferometer 22 is configured for delivering sample light 40 into the anatomical structure 16, where it scatters diffusively, e.g., through the human skull, into the brain, and back out again. Thus, a portion 40a of the sample light 40 will pass through the target voxel 14 and will be scattered by the anatomical structure 16 as signal light 44, and another portion 40b of the sample light 40 will not pass through the target voxel 14 and will be scattered by the anatomical structure 16 as background light 46. The signal light 44 and background light 44 combine together to create a sample light pattern 47 that exits the anatomical structure 16. The interferometer 22 is further configured for combining reference light 42 with the sample light pattern 47 to generate an interference light pattern 48 (e.g., speckle light pattern, which can be defined as an intensity pattern produced by the mutual interference of a set of scattered wavefronts; that is, a speckle light pattern results from the interference of many waves, but having different phases and amplitudes, which add together to give a result wave whose amplitude, and therefore intensity and phase, varies randomly). In the illustrated embodiment, the interferometer 22 is configured for splitting source light 38 into the sample light 40 and reference light 42, as will be described in further detail below.

The reference light 42 may be combined with the signal light 44 in the sample light pattern 47 in a homodyne manner, e.g., by initially frequency shifting the sample light 40 by the frequency $f_{us}$ of the ultrasound 32 delivered into the target voxel 14 by the acoustic assembly 20. That is, if unmodified, the sample light portion 40a passing through the target voxel 14 will be frequency shifted (i.e., tagged) by the ultrasound 32 that also passes through the target voxel 14, such that the signal light 44 will have frequencies $f-f_{us}$. Presumably, the sample light portion 40b not passing through the target voxel 14 will not be frequency shifted (i.e., untagged) by the ultrasound 32, such that the background light 46 will have a frequency f, i.e., the frequency of the sample light 40. It is also that not all of the sample light portion 40a passing through the target voxel 14 will be tagged by the ultrasound 32 (i.e., there exists a tagging efficiency (i.e., the number of tagged photons relative to a number of untagged photons scattered by the target voxel 14)), and therefore, some of the sample light portion 40a passing through the target voxel 14 will be scattered by the anatomical structure 16 as background light 46.

However, assuming that the reference light 42 and the sample light 40 output by the interferometer 22 have the same frequency f, in order to combine the ultrasound tagged signal light 44 in the sample light pattern 47 and the reference light 42 in a homodyne manner, which requires the reference light 42 and signal light 44 to have the same frequency, the frequency f of the sample light 40 or the reference light 42 must initially be shifted relative to each other by the ultrasound frequency $f_{us}$, such that, upon combining by the interferometer 22, the frequency of the ultrasound tagged signal light 44 will be shifted to the same frequency as the reference light 42, and the frequency of the untagged background light 46 will differ from the frequency of the reference light 42 by the ultrasound frequency $f_{us}$. Thus, either the sample light 40 or the reference light 42 will be pre-conditioned, such that the ultrasound tagged signal light 44 will interfere with the reference light 42 in a homodyne manner, resulting in a DC interference component between the reference light 42 and signal light 44 that can be detected by the lock-in camera 28 as the signal component during each pulse, as will be described in further detail below. In contrast, the frequency shifting of the sample light 40 before it enters the anatomical structure 16, or the frequency shifting of the reference light 42, will prevent the untagged background light 46 from interfering with the reference light 42 in a homodyne manner.

In the embodiment illustrated in FIG. 1, the interferometer 22 down frequency shifts the sample light 40 by the ultrasound frequency $f_{us}$ to $f-f_{us}$, such that the ultrasound tagged signal light 44 has the frequency f, the untagged background light 46 has the frequency $f-f_{us}$, and the reference light 42 has a frequency $f_{us}$, thereby enabling combination of the reference light 42 and signal light 44 in a homodyne manner, as further described below with respect to FIG. 3a. However, it is noted that because the ultrasound 32 will tag the signal light 44 with the ultrasound frequencies $+f_{us}$ and $-f_{us}$, as well as other positive and negative multiples of the ultrasound frequency $f_{us}$, other frequency shifting implementations are possible to effect homodyne combination of the reference light 42 and signal light 44. For example, as described in further detail below, the interferometer 22 may up frequency shift the sample light 40 by the ultrasound frequency $f_{us}$ to $f+f_{us}$, such that the ultrasound tagged signal light 44 has the frequency f, the untagged background light 46 has the frequency $f+f_{us}$, and the reference light 42 has a frequency f (see FIG. 3b); may up frequency shift the reference light 42 by the ultrasound frequency $f_{us}$ to $f+f_{us}$, such that the ultrasound tagged signal light 44 has the frequency $f+f_{us}$, the untagged background light 46 has the frequency f, and the reference light 42 has a frequency $f+f_{us}$ (see FIG. 3c); may down frequency shift the reference light 42 by the ultrasound frequency $f_{us}$ to $f-f_{us}$, such that the ultrasound tagged signal light 44 has the frequency $f-f_{us}$, the untagged background light 46 has the frequency f, and the reference light 42 has a frequency $f-f_{us}$ (see FIG. 3d); or perform any other frequency shift of the sample light 40 or reference light 42 that results in the homodyne combination of the reference light 42 and the signal light 44.

The interferometer 22 is further configured for modulating (and in the illustrated embodiment, phase modulating) the interference light pattern to generate a plurality of different interference light patterns, which as will be described in further detail below, enables the amplitude of the signal light 44 to be distinguished from the background light 46.

Figure 3A:
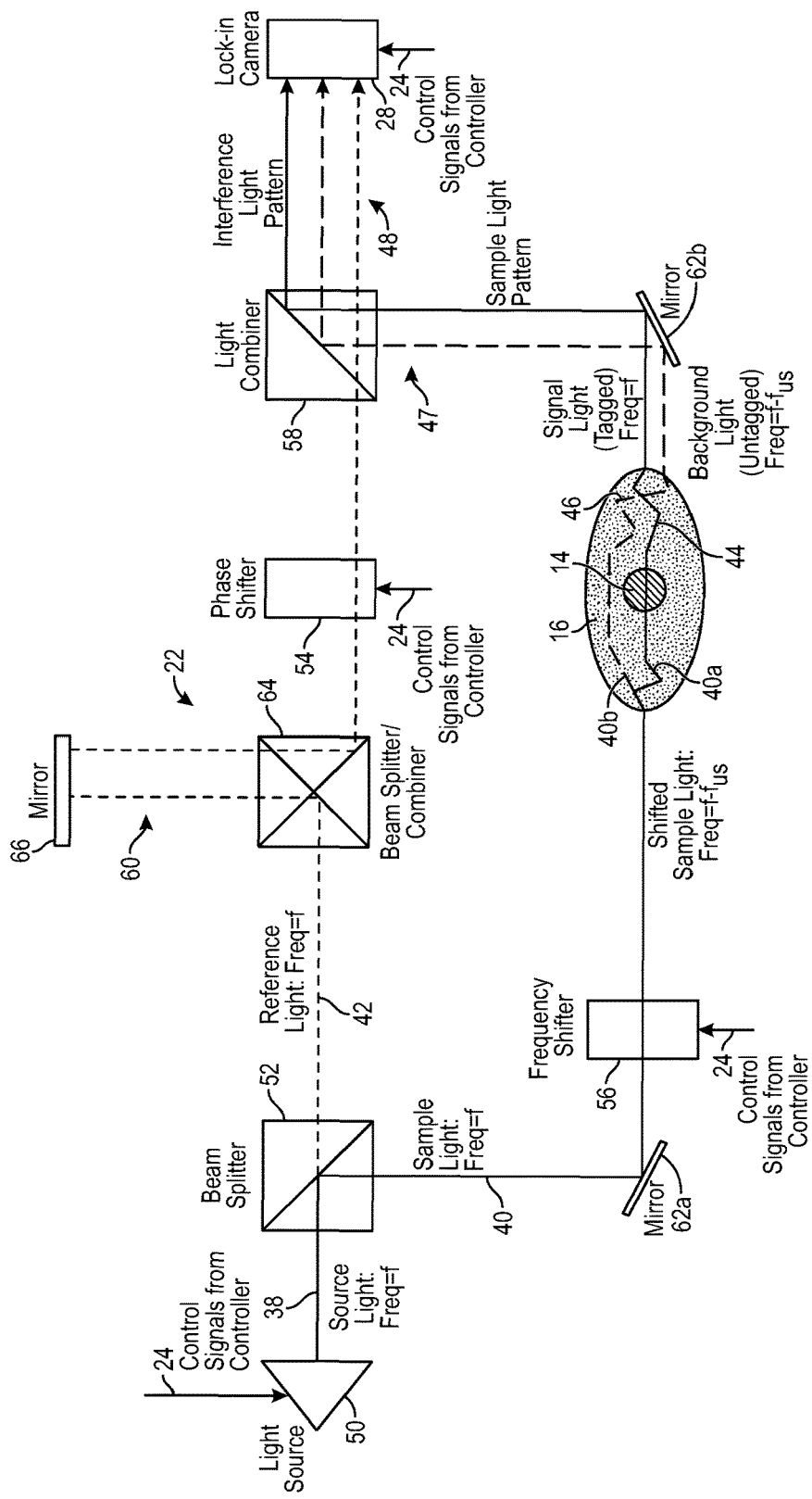
FIG. 3a is a block diagram of one embodiment of an interferometer used in the UOT system of FIG. 1.
Figure 3B:
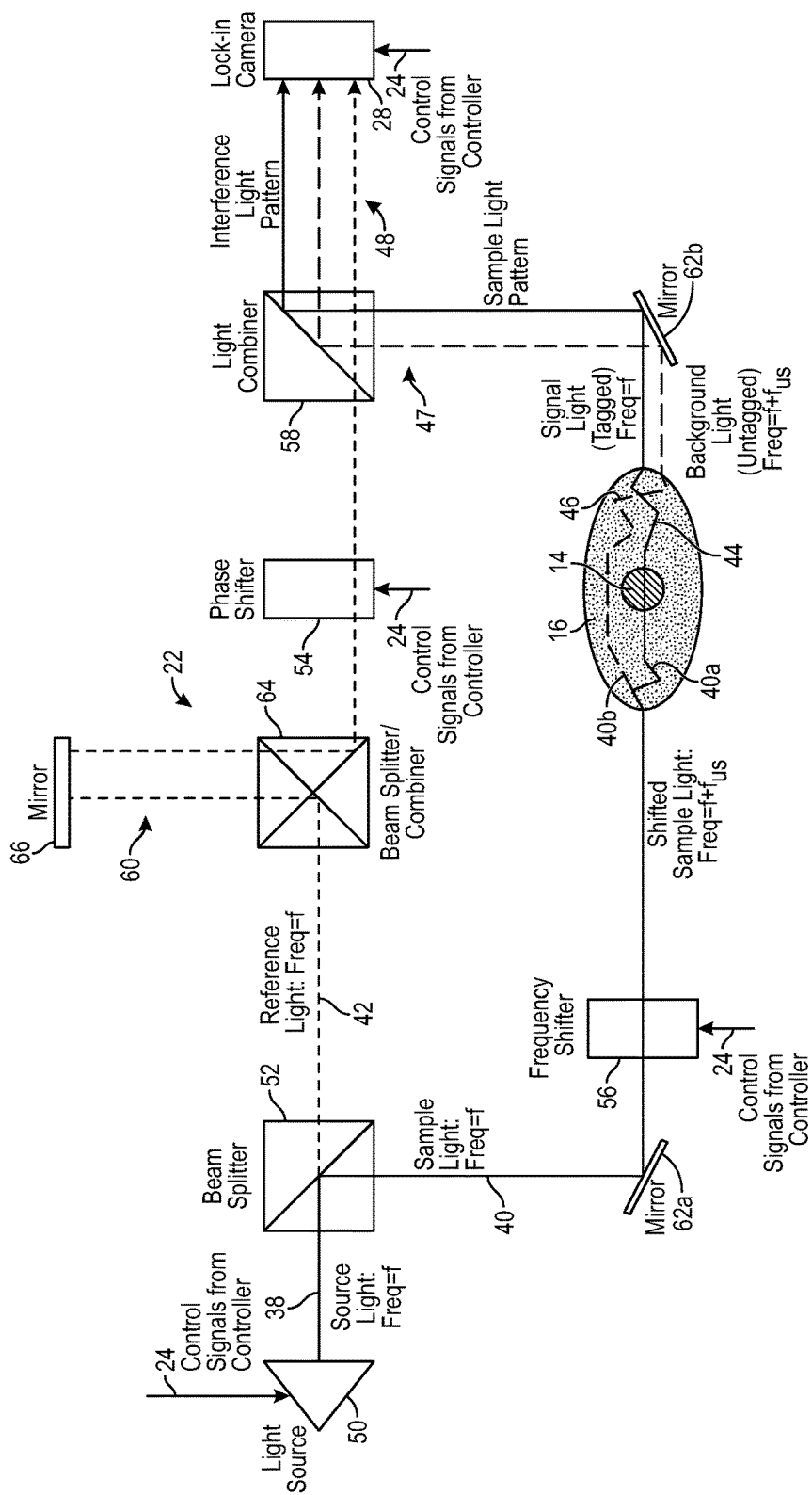
FIG. 3b is a block diagram of another embodiment of an interferometer used in the UOT system of FIG. 1.
Figure 3C:
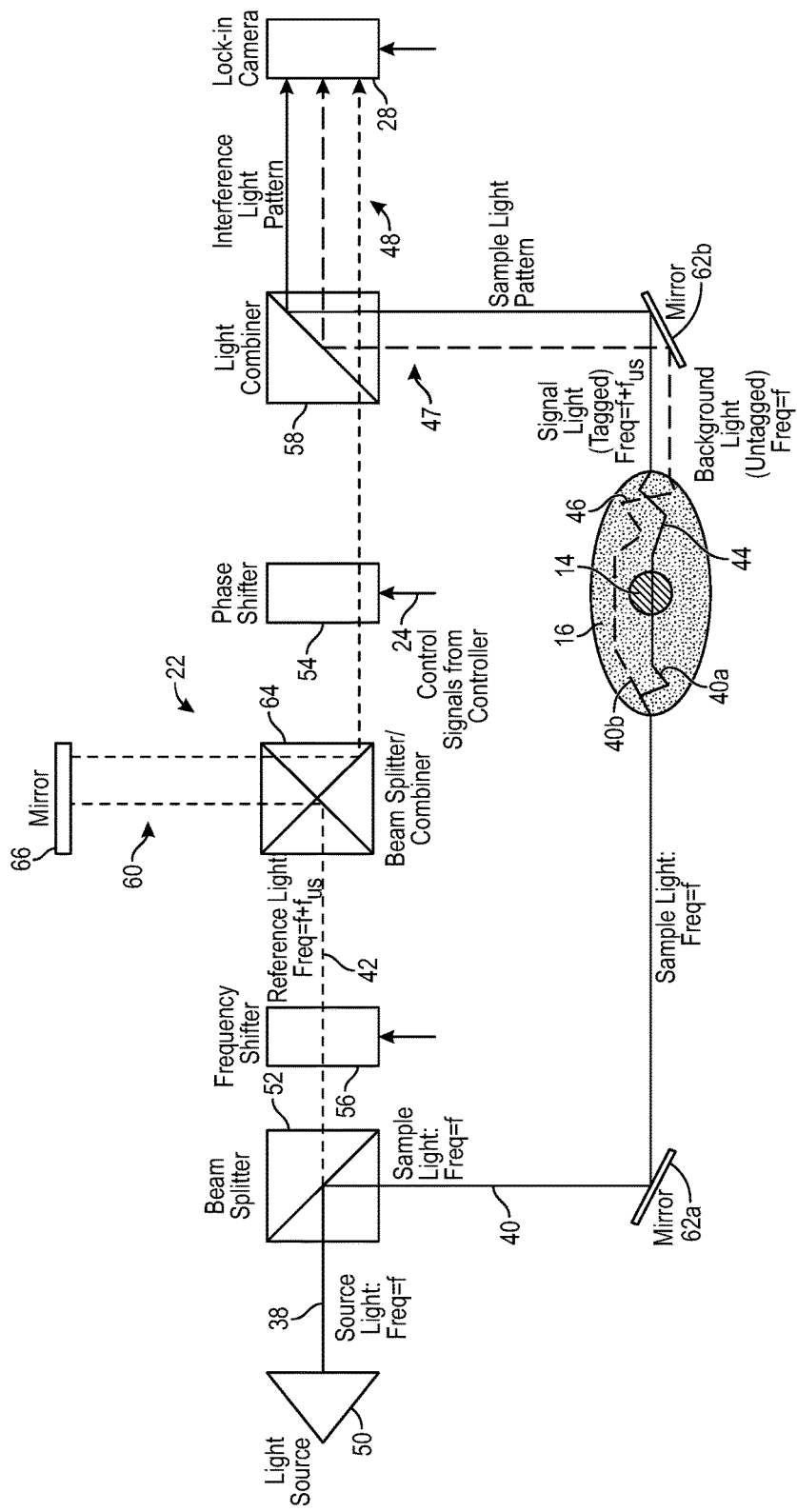
FIG. 3c is a block diagram of still another embodiment of an interferometer used in the UOT system of FIG. 1.
Figure 3D:
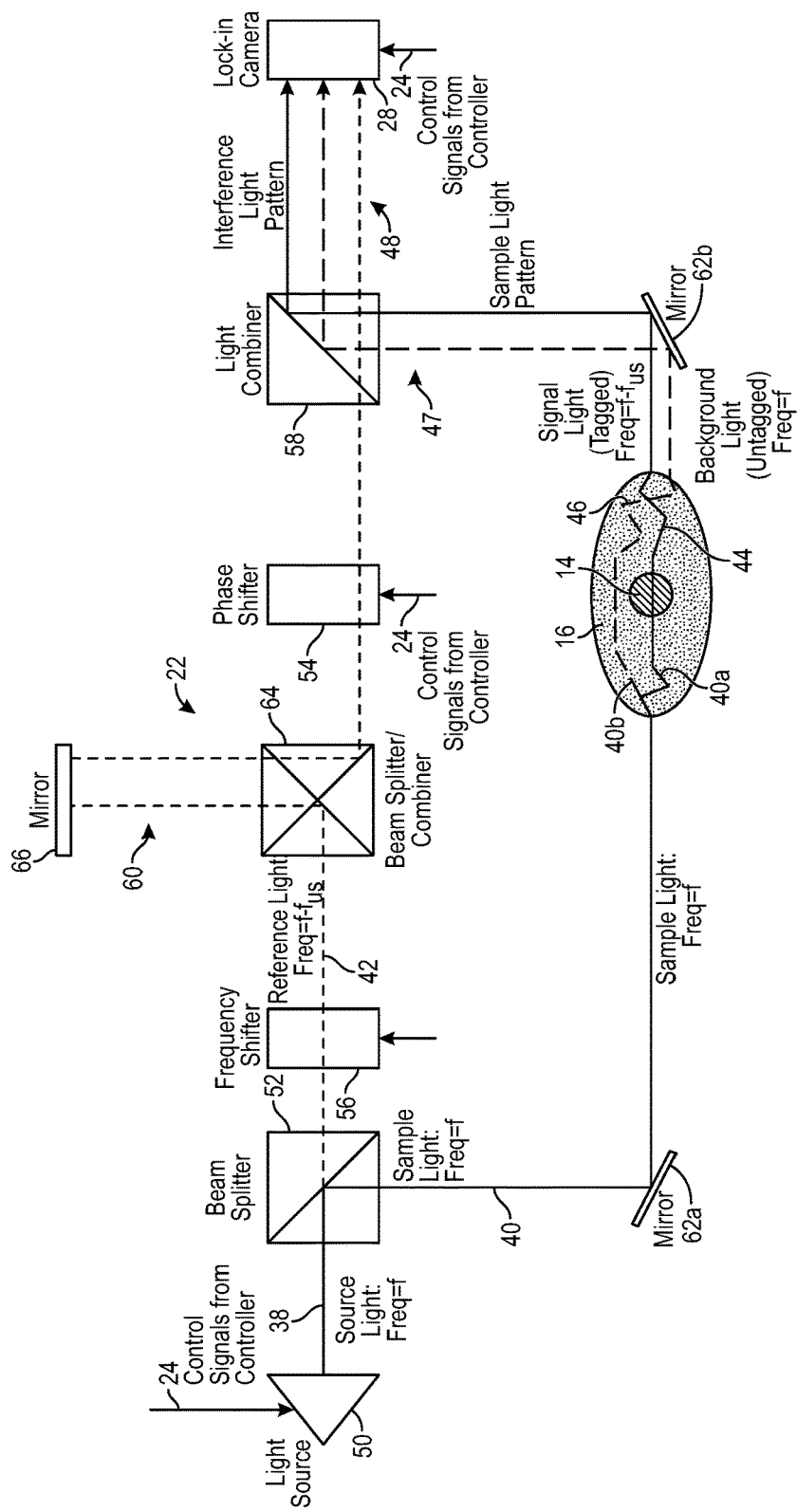
FIG. 3d is a block diagram of yet another embodiment of an interferometer used in the UOT system of FIG. 1.

Referring further to FIG. 3a, one embodiment of the interferometer 22 includes a light source 50, a beam splitter 52, an optical phase shifter 54, an optical frequency shifter 56, a light combiner 58, a path length adjustment mechanism 60, and a set of mirrors 62a, 62b (generally, 62).

The light source 50 is configured for generating coherent light as the source light 38, preferably at a single wavelength (e.g., in the range of 605 nm to 1300 nm), and may take the form of, e.g., a laser diode. In alternative embodiments, multiple light source(s) (not shown) may be used to generate the source light 38 at multiple distinct wavelengths, e.g., one generating source light 38 within the range of 605 nm to 800 nm, and another generating source light 38 within the range of 800 nm to 1300 nm. The coherence length of the source light 38 is preferably at least one meter in order to generate the best speckle contrast in the speckle light pattern 48. The light source 50 may receive power from a drive circuit (not shown), which may include control inputs for receiving control signals from the controller 24 that cause the light source 50 to emit the source light 38 at a selected time, duration, and intensity. Thus, as will be described in further detail below, the controller 24 may selectively pulse the source light 38, and thus the sample light 40 and reference light 42.

As specifically illustrated in FIG. 3a, the beam splitter 52 is configured for splitting the source light 38 into the sample light 40 that propagates along a sample arm of the interferometer 22 and reference light 42 that propagates along a reference arm of the interferometer 22. In the illustrated embodiment, the beam splitter 52 (e.g., a partially transparent mirror) splits the source light 38 via amplitude division by reflecting a portion of the source light 38 as the sample light 40, and transmitting the remaining portion of the source light 38 as the reference light 42, although the beam splitter 52 may alternatively reflect a portion of the source light 38 as the reference light 42, and transmit the remaining portion of the source light 38 as the sample light 40. In alternative embodiments, the beam splitter 52 may split the source light 38 via wavefront division by splitting a portion of the wavefront into the sample light 40 and splitting the remaining portion of the wavefront into the reference light 42. In either case, the beam splitter 52 may not necessarily split the source light 38 equally into the sample light 40 and reference light 42, and it may actually be more beneficial for the beam splitter 52 to split the source light 38 unevenly, such that the amplitude of the sample light 40 is less than the amplitude of the reference light 42 (e.g., 10/90 power ratio) in order to comply with tissue safety standards. That is, the amplitude of the sample light 40 will preferably be relatively low to avoid damaging the tissue, whereas the amplitude of the reference light 42, which will be used to boost the signal light 44 in the interference light pattern 46, will be relatively high.

The optical phase shifter 54 is configured for setting the phase difference between the sample light 40 and reference light 42. The optical phase shifter 54 may include control inputs (not shown) for receiving control signals from the controller 24 that cause the optical phase shifter 54 to set the phase of the reference light 42 relative to the sample light 40. Thus, as will be described in further detail below, the controller 24 may selectively set the phase between the sample light 40 and the reference light 42.

The optical frequency shifter 56 is configured for down frequency shifting the sample light 40 by the ultrasound frequency $f_{us}$ to $f-f_{us}$, such that the frequency of the ultrasound tagged signal light 44 will be f, while the frequency of the background light 46 will be $f-f_{us}$, thereby enabling the homodyne combination of the reference light 42 at frequency f and the ultrasound tagged signal light 44 at frequency f, as described above with respect to FIG. 1. In one alternative embodiment illustrated in FIG. 3*b*, the optical frequency shifter 56 is configured for up frequency shifting the sample light 40 by the ultrasound frequency $f_{us}$ to $f+f_{us}$, such that the frequency of the ultrasound tagged signal light 44 will be f, while the frequency of the background light 46 will be $f+f_{us}$, thereby enabling the homodyne combination of the reference light 42 at frequency f and the ultrasound tagged signal light 44 at frequency f. In one alternative embodiment illustrated in FIG. 3*c*, the optical frequency shifter 56 is configured for up frequency shifting the reference light 42 by the ultrasound frequency $f_{us}$ to $f+f_{us}$, such that the frequency of the ultrasound tagged signal light 44 will be $f+f_{us}$, while the frequency of the background light 46 will be f, thereby enabling the homodyne combination of the reference light 42 at frequency $f+f_{us}$ and the ultrasound tagged signal light 44 at frequency $f+f_{us}$. In still another alternative embodiment illustrated in FIG. 3*d*, the optical frequency shifter 56 is configured for down frequency shifting the reference light 42 by the ultrasound frequency $f_{us}$ to $f-f_{us}$, such that the frequency of the ultrasound tagged signal light 44 will be $f-f_{us}$, while the frequency of the background light 46 will be f, thereby enabling the homodyne combination of the reference light 42 at frequency $f-f_{us}$ and the ultrasound tagged signal light 44 at frequency $f-f_{us}$.

In any event, the frequency shifter 54 may include a local oscillator (not shown) that outputs a signal having a fixed or variable frequency. The local oscillator may be variable, in which case, it may have a control input for receiving control signals from the controller 24 that cause the local oscillator to output a signal at a defined frequency. Alternatively, the local oscillator may be fixed, in which case, it will output a signal having a fixed frequency. In either case, the frequency of the signal output by the local oscillator will be equal to the frequency $f_{us}$ of the ultrasound 32 emitted by the acoustic assembly 20.

The light combiner 58 is configured for combining the reference light 42 with the sample light pattern 47 via superposition to generate the interference light pattern 48. The light combiner 58 can take the form of, e.g., a combiner/splitter mirror.

The path length adjustment mechanism 60 is configured for adjusting the optical path length of the reference light 42 (i.e., the reference arm) to nominally match the expected optical path length of the combined sample light 40 and signal light 44 (i.e., the sample arm), such that the signal light 44 and the reference light 42 reach the light combiner 58 at the same time. The path length adjustment mechanism 60 may include a beam splitter/combiner 64 and an adjustable mirror 66 that can be displaced relative to the beam splitter/combiner 64. The beam/splitter combiner 64 is configured for redirecting the reference light 42 at a ninety-degree angle towards the mirror 66, and redirecting the reference light 42 reflected back from the mirror 66 at a ninety-degree angle towards the light combiner 58. Thus, adjusting the distance between the mirror 66 and the beam splitter/combiner 64 will adjust the optical path length of the reference arm to match the optical path length of the sample arm.

The mirror assembly 62 is configured for confining the optical light paths in the interferometer 22 into a small form factor, and in the illustrated embodiment, includes a first tilted, completely reflective, mirror 62*a* configured for redirecting the sample light 40 at a ninety-degree angle towards the biological specimen 16, and a second tilted, completely reflective, mirror 62*b* configured for redirecting the signal light 44 (and coincidentally a portion of the background light 46) towards the light combiner 58.

Referring back to FIG. 1, the controller 24, which may, e.g., take the form of a central processing unit (CPU), is configured for implementing pulsed wave (PW) UOT by operating the acoustic assembly 20 to pulse the ultrasound 32 (in the illustrated embodiment, by sending on/off control signals to the signal generator 36), and operating the interferometer 22 to pulse the sample light 40 (in the illustrated embodiment, by sending on/off control signals to the drive circuit coupled to the light source 50) in synchrony with the (comparatively very slow) flight of the ultrasound 32, such that only the signal light 44 is frequency shifted (i.e., tagged) by the ultrasound 32. That is, a pulse of the sample light 40 will be delivered into the anatomical structure 16, such that it will pass through the target voxel 14 only as the ultrasound 32 passes through the target voxel 14. In this manner, no portion of the background light 46 will be tagged by the ultrasound 32. As a result, pulsed wave (PW) UOT improves the spatial resolution in the axial direction (or depth) compared to continuous wave (CW) UOT. Thus, PW UOT achieves axial confinement and three-dimensional (3D) spatial resolution, rather than merely two-dimensional (2D) spatial resolution as in the case with CW UOT.

The controller 24 is further configured for operating the interferometer 22 to sequentially modulate the interference light pattern 48 (in the illustrated embodiment, by sending on/off control signals to the optical phase shifter 54) to generate a plurality of different interference light patterns. As will be described in further detail below, the interferometer 22 will set different phases (and in the illustrated embodiment, four different phases equal to 0, $\pi/2$, $\pi$, and $3\pi/2$) between sequential pulses of the sample light 40 and the reference light 42 to facilitate quadrature detection of the signal light 44. As will be also described in further detail below, the controller 24 is further configured for synchronously operating the lock-in camera 28, such that the bin shifting of data detected by the lock-in camera 28 is performed in synchrony with the phase changes in the interferometer 22.

Figure 4:
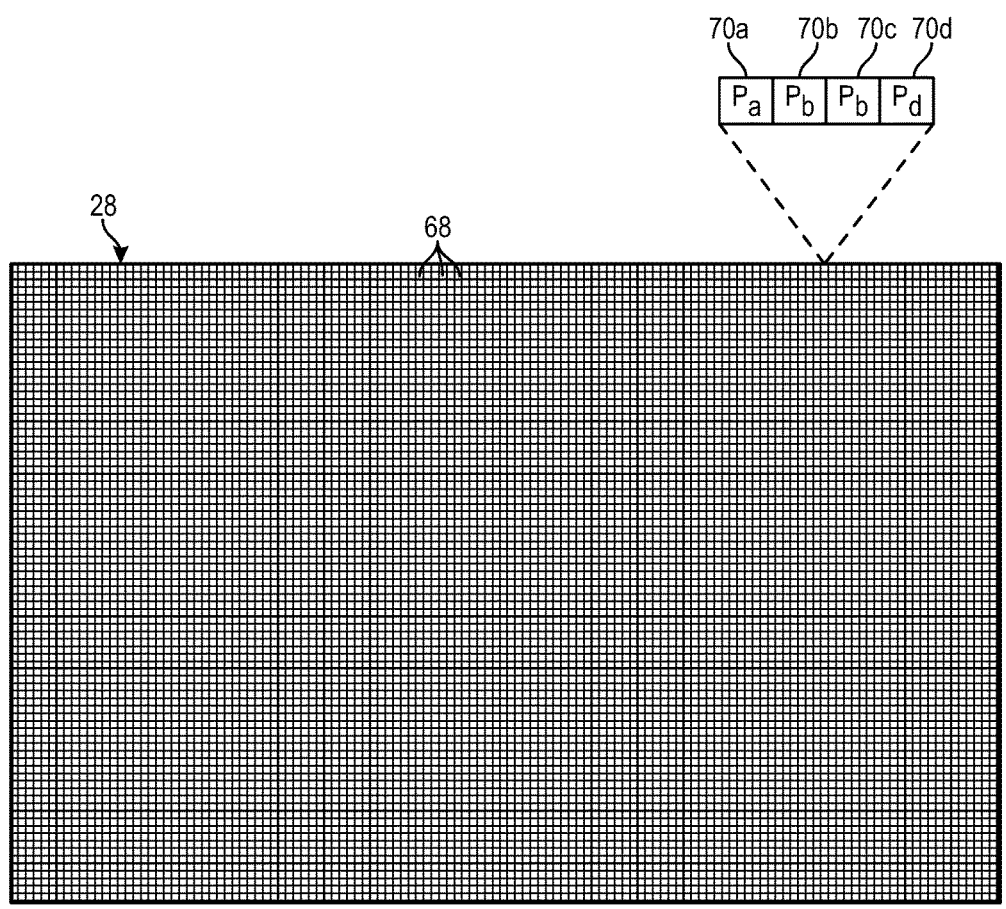
FIG. 4 is a schematic diagram of one embodiment of a detector array used in the UOT system of FIG. 1.

Referring further to FIG. 4, the lock-in camera 28 includes an array of detectors 68 (or "pixels") configured for simultaneously detecting spatial components of each of the different interference light patterns 48. In the case where the interference light pattern 48 is a speckle light pattern, the spatial components are speckle grains (approximately the size of a wavelength of the light) of the speckle light pattern. In general, lock-in cameras include a class of digital cameras in which multiple measurements of a light field are rapidly made at each pixel in a temporally precise fashion synchronized with an external trigger or oscillation and stored in multiple "bins" within each pixel, in contrast with conventional cameras, which store only one value per pixel that merely aggregate the incoming photo-electrons over the camera frame integration time. Lock-in cameras may also perform on-chip computations on the binned values. Thus, the key feature of lock-in cameras is their ability to rapidly capture and store multiple sequential samples of the light field, with sample-to-sample latencies shorter than readout times of conventional cameras. This feature enables them, for example, to sample a modulated light field at the same frequency as the modulation, such that subtraction across successive samples, or other operations, such as quadrature detection (discussed below) will extract the component of the light that is modulated at the modulation frequency, while subtracting off the unmodulated ("DC") background. Similarly, lock-in cameras can be used to make a series of such measurements or comparisons, locked to an external trigger signal (generated by the controller 24), rapidly in order to extract such modulated components from a rapidly changing light field arising from a dynamic, disordered biological specimen.

Thus, each detector 68 of the lock-in camera 28 respectively stores a plurality of values in a plurality of bins 70a-70d representative of the spatial component of the four interference light patterns 48, and in this case, four bins 70a-d (in general, 70) for storing four values from the respective four interference light patterns 48. The spatial component values stored in the bins 70 of a respective detector 68 may be, e.g., the intensity values of the respective spatial component of interference light patterns 48. For example, for any particular detector 68 (or pixel) corresponding to a particular spatial component (or speckle grain), four power values $P_a$-$P_d$ for the four interference patterns 48 will be respectively stored in the four bins 70a-70d. As will be described in further detail below, the spatial component power values $P_a$-$P_d$ detected by each detector 68 of the camera 28 for the four interference patterns 48 can be used to reconstruct the amplitude of the signal light 44, and thus, can be said to be representative of the physiologically-dependent optical parameters (e.g., optical absorption) of the target voxel 14. The lock-in camera 28 includes control inputs (not shown) for receiving control signals from the controller 24, such that the detection and binning of the data can be coordinated with the pulsing of the ultrasound 32 and sample light 40 described in further detail below.

Although only a single lock-in camera 28 is illustrated, it should be appreciated that multiple lock-in cameras 28 (e.g., in an array) or a lock-in camera in the form of multiple camera sensor chips on a common circuit board, can be used to increase the number of detectors 68 (i.e., pixels). Although not illustrated, the system 10 may include magnification optics and/or apertures to magnify the individual speckle grains, which may have a size on the order of the wavelength of the near-infrared or visible light used to acquire the data voxel, and hence on the order of hundreds of nanometers in size, to approximately the sizes of the detectors 68 of the lock-in camera 28. Thus, in the illustrated embodiment, the pixel sizes and pitches of the lock-in camera 28 are matched to the speckle grain sizes and pitches of the interference light pattern 48 via the appropriate magnification, although other embodiments are possible.

Figure 5:
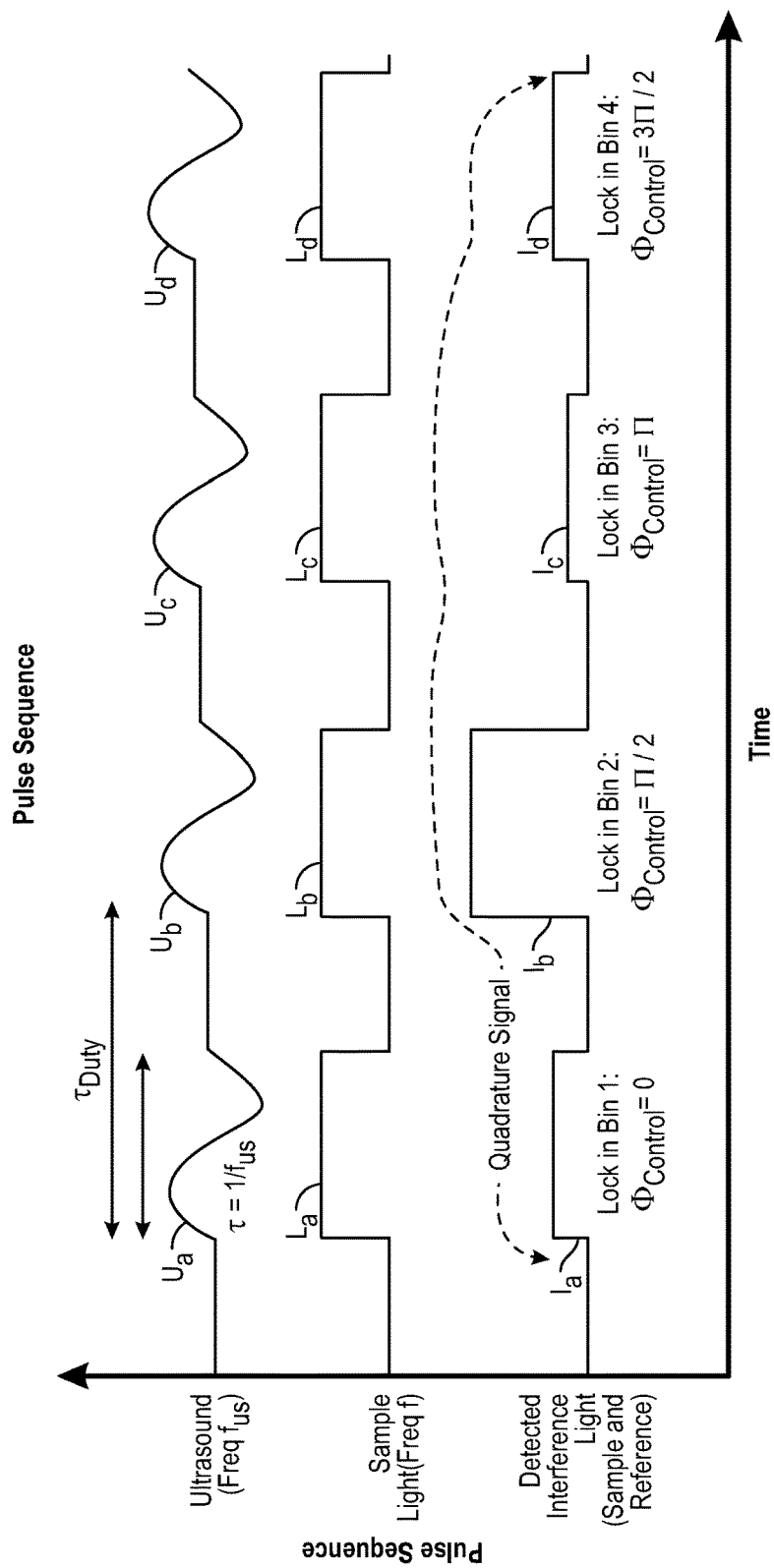
FIG. 5 is a timing diagram of one pulsing sequence used by the UOT system to detect a physiologically-dependent optical parameter in a target voxel within an anatomical structure.
Figure 6:
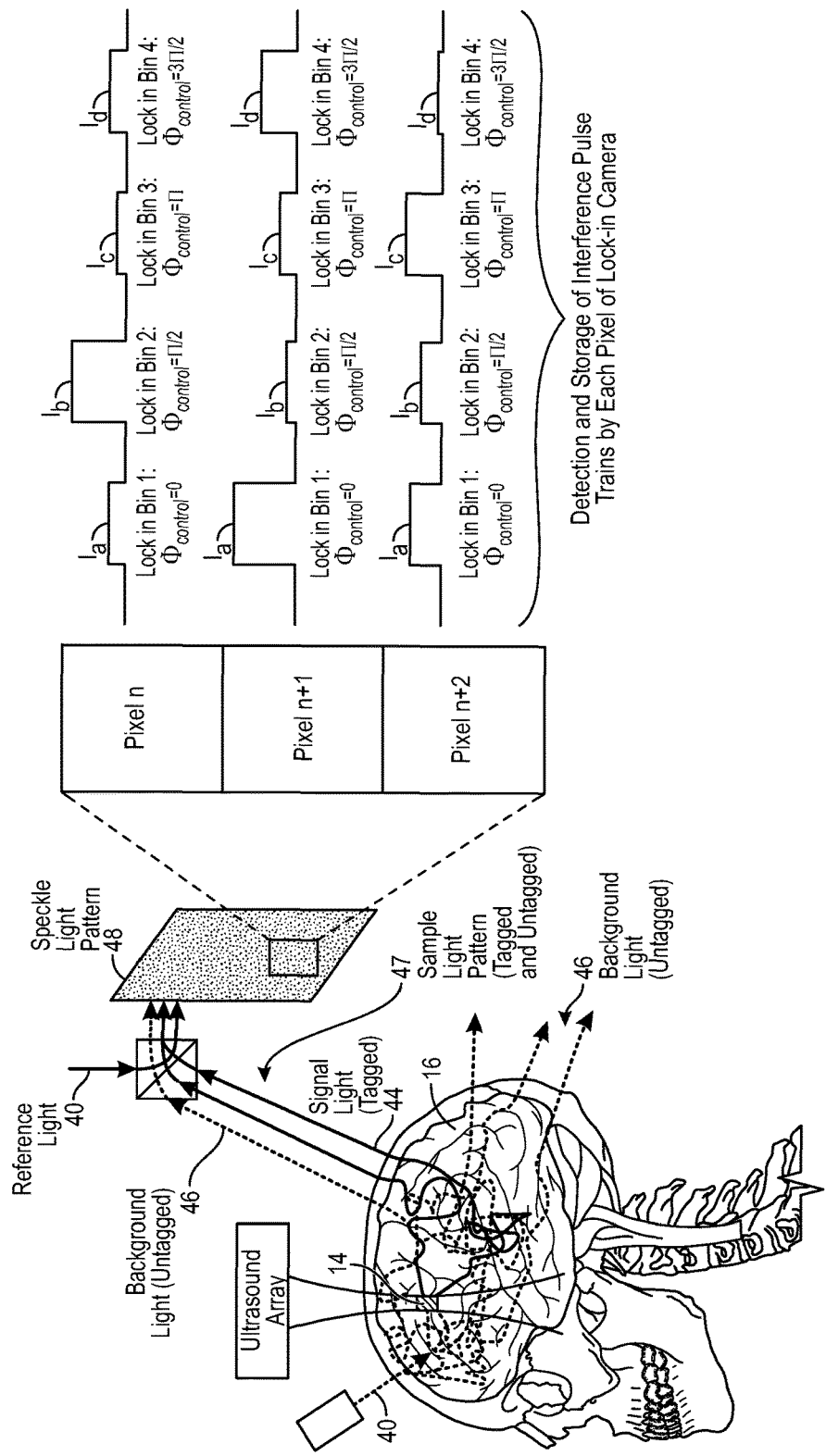
FIG. 6 is a schematic diagram of the UOT system of FIG. 1, particularly showing the generation of interference light patterns, the detection of spatial components in the, and binning of spatial component values.

Referring to FIGS. 5 and 6, one pulsing sequence that can be used in a PW UOT technique performed by the system 10 for generating four interference light patterns 48 and detecting and storing the spatial component power values for the interference light patterns 48 will be described.

During one acquisition of a single data voxel (i.e., acquisition of data characterizing the target voxel 14), an ultrasound pulse train consisting of four separate, but identical, ultrasound pulses $U_a$-$U_d$ are delivered into the target voxel 14. In this embodiment, the duration τ of each ultrasound pulse U is equal to only one full cycle of the ultrasound 32 to maximize the data acquisition speed, and thus, is equal to $1/f_{us}$, although in alternative embodiments, the duration τ may be several ultrasound cycles long (e.g., on the order of 1 microsecond or less than one microsecond). It should be noted that it is desirable to minimize the duration t of the ultrasound pulse U in order to minimize ultrasound focal confinement at the target voxel 14.

The duty cycle of the ultrasound pulses $U_a$-$U_d$ (i.e., the time that elapses between the beginning of one pulse U to the beginning of the next pulse U) is $\tau_{duty}$. The duty cycle $\tau_{duty}$ may be selected to allow each ultrasound pulse U to exit the anatomical structure 16 before the next measurement is taken, such that the ultrasound tagged signal light 44 is only present at high pressures at the three-dimensional location of the target voxel 14. The frame rate of the lock-in camera 28 should be selected to match the duty cycle $\tau_{duty}$ of the ultrasound pulse U, such that there exists one ultrasound pulse U per frame.

A light pulse train consisting of four sample light pulses $L_a$-$L_d$ is also delivered into the anatomical structure 16 in synchrony with the delivery of the four ultrasound pulses $U_a$-$U_d$, such that, as each ultrasound pulse U passes through the target voxel 14, the sample light pulse L likewise passes through the target voxel 14.

In this manner, only the signal light 44 (and none of the background light 46) is tagged with the ultrasound, as discussed above. In this particular embodiment, only one sample light pulse L is delivered for each ultrasound pulse U. Thus, there is a one-to-one correspondence between the sample light pulses $L_a$-$L_d$ and the ultrasound pulses $U_a$-$U_d$. Although each of the sample light pulses L is illustrated in FIG. 5 as having the same width as the width of the respective ultrasound pulses U for purposes of illustration, each sample light pulses L is, in practicality, at least slightly smaller than the respective ultrasound pulse U due to the latency period required for the respective ultrasound pulse to reach the target voxel 14. Alternatively, the duration of the sample light pulse L, the duration of the sample light pulse L can be much less than the duration of the ultrasound pulse U. In any event, the duration of the sample light pulse L preferably should be approximately matched to be an integer multiple of the frequency of the ultrasound frequency $f_{us}$, e.g., if the ultrasound frequency $f_{us}$ of 2 MHz, the duration of the sample light pulse L should be multiples of 0.5 microseconds. Although FIG. 5 illustrates only one ultrasound cycle per ultrasound pulse U, if the duration of the sample light pulse L is multiple integers of the frequency of the ultrasound frequency $f_{us}$, the number ultrasound cycles per ultrasound pulse U is preferably equal to the same multiple integer. This ensures that a full, balanced cycle of tagged light is generated. The energy of each sample light pulse L should be sufficiently high, e.g., on the order of 1 microsecond in duration (but can be as low as 10 nanoseconds in duration) and tens of micro-Joules per square centimeter.

For each of the four separate ultrasound pulses $U_a$-$U_d$ occurring during the acquisition of a single data voxel, the phase difference between the reference light 42 and the sample light 40 is set to a different setting, and in this case, to one of 0, π/2, π, and 3π/2. In the illustrated embodiment, the phase between the reference light 42 and the sample light 40 is sequentially set to 0, π/2, π, and 3π/2, although these phase settings can be performed in any order, as long as all four phase settings 0, π/2, π, and 3π/2 are used during the acquisition of a single data voxel.

The respective pulses of the sample light pattern 47 and reference light 42 are then combined into the interference light patterns 48, each having four corresponding interference pulses $I_a$-$I_d$ that can be detected by the lock-in camera 28. That is, for each interference pulse I, a detector 68 detects a spatial component of the respective interference pulse I (e.g., a speckle grain in the case where the interference light pattern 48 includes a speckle pattern) and stores the spatial component value (e.g., power) within a respective one of the bins 70.

That is, at phase φ=0, a given pixel n will detect and store the value of the respective spatial component of the interference pulse $I_a$ into bin 1 of the pixel n; at phase φ=π/2, the pixel n will detect and store the value of the respective spatial component of the interference pulse $I_b$ into bin 2 of the pixel n; at phase φ=π, the pixel n will detect and store the value of the respective spatial component of the interference pulse $I_c$ into bin 3 of the pixel n; and at phase φ=3π/2, the pixel n will detect and store the value of the respective spatial component of the interference pulse $I_d$ into bin 4 of the pixel n.

Similarly, at phase φ=0, the next pixel n+1 will detect and store the value of the respective spatial component of the interference pulse $I_a$ into bin 1 of the pixel n+1; at phase φ=π/2, the pixel n+1 will detect and store the value of the respective spatial component of the interference pulse $I_b$ into bin 2 of the pixel n+1; at phase φ=π, the pixel n+1 will detect and store the value of the respective spatial component of the interference pulse $I_c$ into bin 3 of the pixel n+1; and at phase φ=3π/2, the pixel n+1 will detect and store the value of the respective spatial component of the interference pulse $I_d$ into bin 4 of the pixel n+1.

Similarly, at phase φ=0, the next pixel n+2 will detect and store the value of the respective spatial component of the interference pulse $I_a$ into bin 1 of the pixel n+2; at phase φ=π/2, the pixel n+2 will detect and store the value of the respective spatial component of the interference pulse $I_b$ into bin 2 of the pixel n+2; at phase φ=π, the pixel n+2 will detect and store the value of the respective spatial component of the interference pulse into bin 3 of the pixel n+2; and at phase φ=3π/2, the pixel n+2 will detect and store the value of the respective spatial component of the interference pulse $I_d$ into bin 4 of the pixel n+2.

Thus, for each of an n number of pixels, four values will be respectively stored in the four bins 1-4. Significantly, in the case where the interference light pattern 48 includes a speckle light pattern, it is important that all four sample light pulses P be delivered by the interferometer 22 to the target voxel 14 and that all four interference pulses I be detected and recorded by the camera 28 within the characteristic speckle decorrelation time of the target voxel 14, which scales super-linearly with the depth into the anatomical structure 16 at which the target voxel 14 is located. For imaging deep inside a living biological tissue, such as through the human skull and into the human cerebral cortex, the speckle decorrelation time is expected to be on the order of microseconds to tens of microseconds. For imaging directly into living brain matter in the absence of skull, speckle decorrelation times have been measured to be on the order of ten milliseconds for 1-millimeter penetration or 1-millisecond for 3-millimeter penetration. Notably, the speckle decorrelation time impacts the depth scaling of lock-in camera based UOT in dynamic scattering media, such as biological tissue, namely the constraint that multiple phase-shifted measurements must be made within the speckle decorrelation time (see, e.g., Qureshi M M, Brake J., Jeon H J, Ruan H, Liu Y, Safi A M, Eom T J, Yang C., Chung E, "In Vivo Study of Optical Speckle Decorrelation Time Across Depths in the Mouse Brain," Biomedical Optics Express, Vol. 8, No. 11, pp. 4855-4864 (Nov. 1, 2017). Thus, it is important that the time window in which the set of quadrature measurements is short enough that the target voxel 14 does not have the time to de-correlate significantly. Otherwise, the signal-to-noise ratio is diminished.

Figure 7:
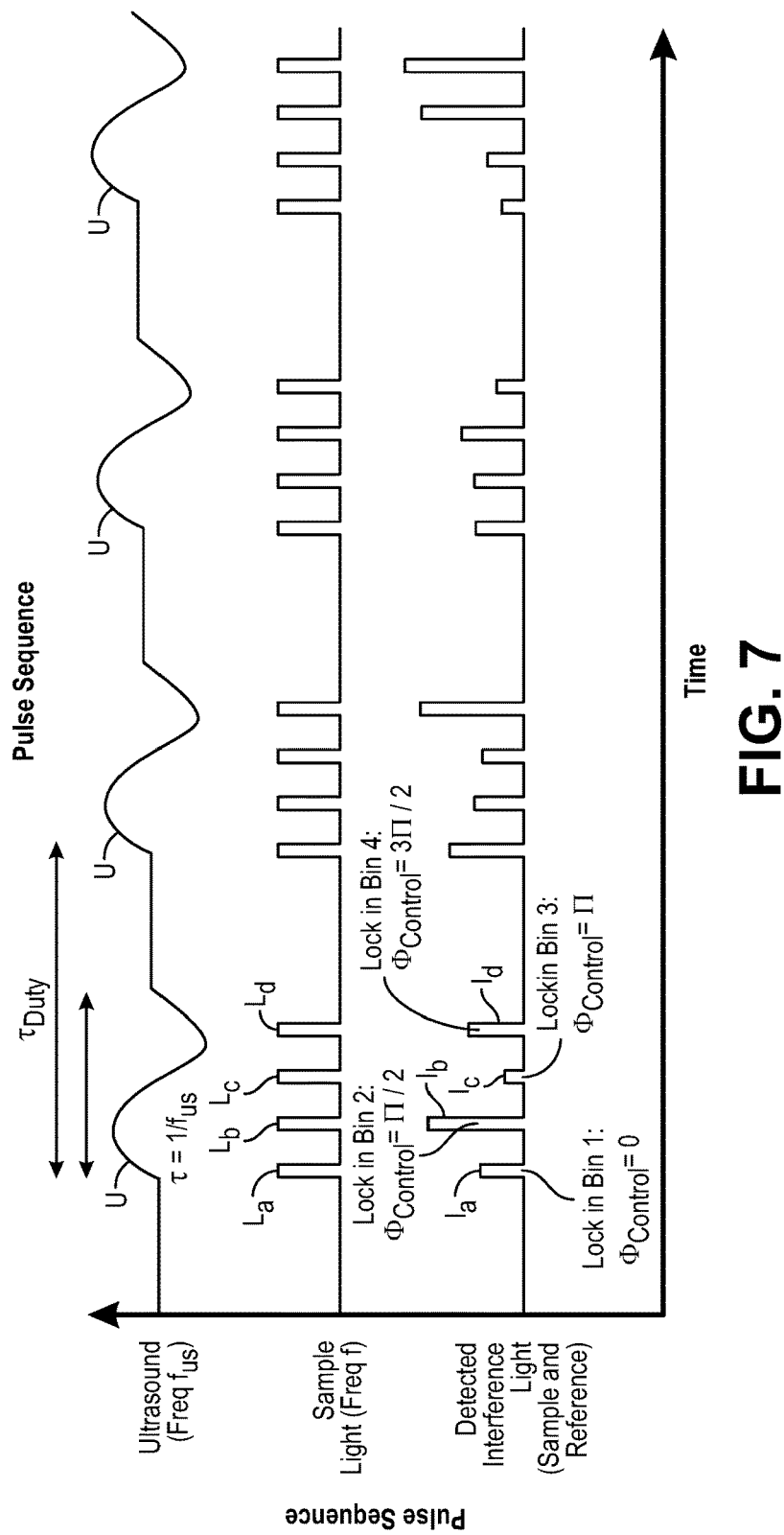
FIG. 7 is a timing diagram of another pulsing sequence used by the UOT system to detect a physiologically-dependent optical parameter in a target voxel within an anatomical structure.

Referring to FIG. 7, another particularly advantageous pulsing sequence that can be used in a PW UOT technique performed by the system 10 for generating four interference light patterns 48 and detecting and storing the spatial component power values for the interference light patterns 48 will be described. The pulsing sequence of FIG. 7 is identical to the pulsing sequence of FIG. 5, with the exception that multiple sample light pulses L, and in this embodiment, all four sample light pulses L, are delivered to the target voxel 14 for each ultrasound pulse U delivered to the target voxel 14, thereby accelerating the delivery of the sample light pulses P by the interferometer 22 to the target voxel 14, and the resultant generation, detection, and recording of all four interference pulses I by the camera 28. That is, because the four sample light pulses L are delivered for each ultrasound pulse U, the speed of the data voxel acquisition is increased by a factor of four.

In particular, during the acquisition of four consecutive data voxels (as opposed to only one in the pulsing sequence of FIG. 5), an ultrasound pulse train consisting of four separate, but identical, ultrasound pulses U are delivered into the target voxel 14. As with the case in the pulsing sequence of FIG. 5, the duration t of this ultrasound pulse U is equal to only one full cycle of the ultrasound 32 to maximize the data acquisition speed, and thus, is equal to $1/f_{us}$. The duration t of this ultrasound pulse U and the duty cycle $\tau_{duty}$ of the ultrasound train pulse of FIG. 7 can be identical to the respective duration t and duty cycle $\tau_{duty}$ of the ultrasound pulse train in the pulsing sequence of FIG. 7.

A light pulse train consisting of four sets of sample light pulses, with each set comprising four sample light pulses $L_a$-$L_d$, are also delivered into the anatomical structure 16 in synchrony with the delivery of the four ultrasound pulses U, such that as each ultrasound pulse U passes through the target voxel 14, the corresponding set of four sample light pulses $L_a$-$L_d$, likewise pass through the target voxel 14. Thus, only the signal light 44 (and none of the background light 46) is tagged with the ultrasound, as discussed above. Thus, four sample light pulses $L_a$-$L_d$ are delivered for each ultrasound pulse U. Thus, there is a four-to-one correspondence between the sample light pulses $L_a$-$L_d$ and ultrasound pulses U.

Thus, in the same manner described above with respect to the pulsing sequence illustrated in FIG. 5, for each ultrasound pulse U occurring during the acquisition of a single data voxel, the phase difference between the reference light 42 and the sample light 40 is set to a different setting, and in this case, to one of 0, π/2, π, and 3π/2, to generate four interference pulses $I_a$-$I_d$. The quick detection and storage scheme of the lock-in camera 28 enables acquisition of an entire data voxel within one cycle of the ultrasound 32, well within the speckle decorrelation time of the target voxel 14.

It can be appreciated that the use of the lock-in camera 28 provides for a high-speed and precisely timed detection method that can capture differences in a light field far faster than the frame rates of conventional cameras. In the illustrated embodiment, the lock-in camera 28 rapidly measures the four quadratures of the pulse sequences illustrated in FIGS. 5 and 7. The acquisition sequence can be precisely timed to external signals for integration with optimal ultrasound and light pulse sequences. The lock-in camera 28 also enables an efficient detection scheme compared to conventional pulsed UOT, since the pulsed UOT signals may be quickly detected with a high signal-to-noise ratio, while using the full bit depth of the analog-digital conversion available in the signal chain due to rejection of DC background by the lock-in camera 28. The lock-in camera 28 provides for a simplified detection scheme that is highly scalable to large numbers of pixels and high frame rates, enabling the maximization of signal capture in UOT, thereby improving spatial and temporal resolution.

It should be appreciated that in addition to the ability of the combination of the pulsed UOT with a lock-in camera to provide high axial spatial resolution and high sensitivity from the high-speed lock-in detection, such combination also provides the additional advantage of efficiently detecting the signal light associated with a specific time point on the ultrasound phase cycle (e.g., at the peaks of the ultrasound phase cycle). As such, the pulsed UOT/lock-in camera combination can accurately image tissue with a relatively small number of data measurements, and thus, a relatively short period of time, preferably within the speckle decorrelation time of the target voxel. In comparison, a continuous wave approach results in averaging light signal detection over a range of arbitrarily placed points on the ultrasound phase cycle, leading to a diminished overall detection sensitivity, requiring that, for sufficient sensitivity, data measurements be taken over a period time longer than the speckle decorrelation time of the target voxel. Thus, the use of pulsed UOT in combination with the lock-in camera allows deeper imaging into tissue.

Figure 8:
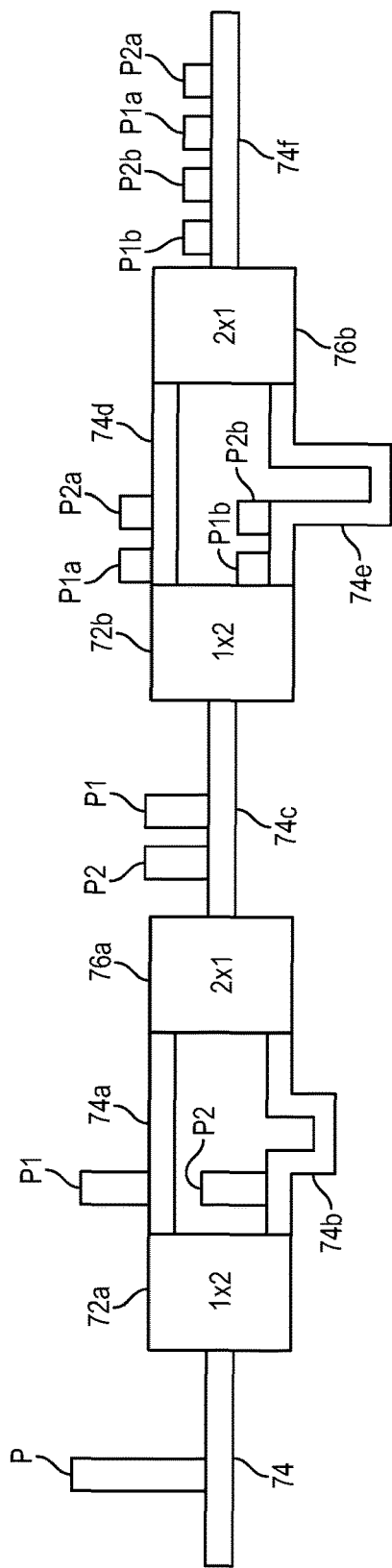
FIG. 8 is a plan diagram of one embodiment of an optical assembly used to split a single optical pulse into a train of identical optical pulses for use in the UOT system of FIG. 1.

The detection processes illustrated in FIGS. 5 and 7 require the ultrasound timing and intensity to be consistent. As such, the output of the acoustic assembly 20 may be periodically sampled to ensure that the system 10 does not suffer from ultrasound performance drift, for instance, as the transducer arrangement 34 heats. Furthermore, the detection processes illustrated in FIGS. 5 and 7 require that all of the light pulses used between phase changes in the quadrature measurements be equal in strength, or at least exhibit a known ratio that can be normalized out post-detection. In the case that the pulse-to-pulse variations in the light intensity emitted by the light source 50 are too large, the optical arrangement illustrated in FIG. 8 can be utilized to generate optical pulses that are identical in intensity and intensity-time profile, but temporally separated from each other.

In particular, this optical arrangement includes a first 1×2 fiber splitter 72a in which a single optical pulse P (generated by the light source 50) is input via an optical fiber 74 and split into two identical optical pulses P1, P2. Two optical fibers 74a, 74b of different optical lengths are connected to the respective outputs of the first 1×2 fiber splitter 72a, such that the two identical optical pulses P1, P2 respectively propagate within the two optical fibers 74a, 74b. The optical arrangement further includes a first 2×1 fiber coupler 76a into which the two identical optical pulses P1, P2 are input and combined, and output to a single optical fiber 74c. By making the lengths of the optical fibers 74a, 74b different from each other, the single optical pulse P input into the first 1×2 fiber splitter 72a is effectively split into two identical optical pulses that propagate through the single optical fiber 74c and are spaced out by a time difference determined by the optical path length difference between the two optical fibers 74a, 74b. This conveniently enables the creation of two optical pulses that track each other identically.

Another fiber coupler and pair of optical fibers can be added to create four identical optical pulses separated from each other in time. In particular, the optical arrangement further includes a second 1×2 fiber splitter 72b to which the single optical fiber 74c carrying the two identical and temporally spaced optical pulses P1, P2 is coupled. Thus, the two identical optical pulses P1, P2 are input into the second 1×2 fiber splitter 72b and split into four identical optical pulses P1a, P1b, P2a, P2b (i.e., the optical pulse P1 is split into optical pulses P1a, P1b, and the optical pulse P2 is split into optical pulses P2a, P2b). Two optical fibers 74d, 74e of different optical lengths are connected to the respective outputs of the second 1×2 fiber splitter 72b, such that the two sets of two identical optical pulses P1a, P1b and P2a, P2b respectively propagate within the two optical fibers 72d, 72e. The optical arrangement further includes a second 2×1 fiber coupler 76b into which the two sets of identical optical pulses P1a, P1b and P2a, P2b are input and combined, and output to a single optical fiber 74f. By making the lengths of the optical fibers 74d, 74e different from each other, the two optical pulses input into the second 1×2 fiber splitter 72b are effectively split into four identical optical pulses that propagate through the single optical fiber 74f and spaced out by a time difference determined by the optical path length difference between the two optical fibers 74d, 74e. This conveniently enables the creation of four optical pulses that track each other identically.

Referring back to FIG. 1, once the camera 28 acquires the data voxel by storing all spatial component values of each of the four interference pulses $I_a$-$I_d$ within the four bins 70 of each of the detectors 68, these data can be sent to the processor 30 (which can, e.g., take the form of a computer, field-programmable gate array or application specific integrated circuit), which is configured for determining a physiologically-dependent optical parameter (e.g., absorption) of the target voxel 14 based on the four values stored in the bins 70 of each detector 68. As briefly discussed above, the four spatial component values can be power values $P_a$-$P_d$, which can be used by the processor 30 to reconstruct the amplitude of the signal light 44, and thus, can be said to be representative of the physiologically-dependent optical parameters (e.g., optical absorption) of the target voxel 14.

The spatial component power values $P_a$-$P_d$ for all four interference light patterns $I_a$-$I_d$ can be used in accordance with known "quadrature detection" methods to reconstruct the amplitude of the signal light 44, which is proportional to the number of tagged photons emerging from the target voxel 14 (i.e., the number of photons in the signal light 44), and thus, can be used to measure optical absorption in the target voxel 14 (e.g., for the purpose of measuring spatially localized neural activity-correlated changes in the level of deoxygenated and/or oxygenated hemoglobin concentration or relative abundance in the brain, which appear as localized changes in the optical absorption of blood). In the illustrated embodiment, it should be understood that because of the diffusive scattering of light over large distances through the brain and skull, the interference light pattern 48 detected by the lock-in camera 28 takes the form of a random speckle pattern in which each localized speckle grain has a definite, but random phase offset in the interference light pattern 48 (i.e., a beat pattern) between the reference light 42 and the signal light 44. This results in the unknown random phases in the beat patterns measured by each detector 68 (or pixel) in the equations set forth below.

In particular, the power detected at a single detector 68 (or pixel) for each optical pulse at one of the four phases can be expressed as:

$$\text{Value}_{1,k} = P_{background} + P_{signal} + P_{reference} + 2(P_{signal} \times P_{reference})^{1/2} \times \cos(\varphi_{control} - \varphi_{unknown1, speckle\ k}) + 2(P_{signal} \times P_{background})^{1/2} \times \cos(2\pi \times f_{us} - \varphi_{unknown2, speckle\ k}) + 2(P_{reference} \times P_{background})^{1/2} \times \cos(2\pi \times f_{us} - \varphi_{unknown3, speckle\ k}),\quad [1]$$

where $P_{background}$ represents light at frequency f–$f_{us}$ that has not been tagged with the ultrasound 32; $P_{signal}$ represents light at frequency f that has been tagged with the ultrasound 32; $P_{reference}$ represents the reference light at frequency f; $\varphi_{control}$ is a control phase shift introduced into the reference light 42 for each detected interference pattern 48; $\varphi_{unknown1,\ speckle\ k}$, $\varphi_{unknown2,\ speckle\ k}$, and $\varphi_{unknown3,\ speckle\ k}$ are random phases at the kth speckle grain at the time of measurement, which originates via multiple scattering of coherent light inside the tissue.

The terms $P_{background}+P_{signal}+P_{reference}$ are constant across all four optical pulses with different control phase values $\varphi_{control}$. The terms $2(P_{signal} \times P_{background})^{1/2} \times \cos(2\pi \times f_{us} - \varphi_{unknown2}) + 2(P_{reference} \times P_{background})^{1/2} \times \cos(2\pi \times f_{us} - \varphi_{unknown3})$ oscillate at the frequency $f_{us}$, and are not detected by the lock-in camera 28 given appropriate light pulse duration and integration time, and thus, can be ignored. As such, equation [1] can be reduced to:

$$\text{Value}_k = P_{background} + P_{signal} + P_{reference} + 2(P_{signal} \times P_{reference})^{1/2} \times \cos(\varphi_{control} - \varphi_{unknown}), \quad [2]$$

which is analogous to:

$$A + B \times \cos(\varphi_{control} + \varphi_{unknown}), \quad [3]$$

where $\varphi_{control}$ can be respectively set to 0, $\pi/2$, $\pi$, and $3\pi/2$ to create four equations. Both the amplitude B and the unknown phase $\varphi_{unknown}$ can be extracted by solving the resulting four equations using the standard trigonometric identities.

Thus, the term magnitude of $P_{signal} \times P_{reference}$ can be extracted by shifting the control phase $\varphi_{control}$ successively on each of four successive pulses $\varphi_{control} = 0$, $\pi/2$, $\pi$, and $3\pi/2$. Even though $\varphi_{unknown}$ is an unknown and random phase, specific to each pixel, which results from the laser speckle pattern due to light scattering in the tissue, by measuring and storing each of these four measurements at different control phase values $\sigma_{control}$, the value of the interference term $2(P_{signal} \times P_{reference})^{1/2}$ may be extracted via the known principal of "quadrature detection." Because the power of the reference signal light $P_{reference}$ is known or independently measurable, the interference term $P_{signal} \times P_{reference})^{1/2}$ serves as a measurement of the power of the signal light $P_{signal}$. Thus, using a known scaling relationship, the power of the signal light $P_{signal}$ can be determined (either in the absolute sense or relative sense) from the extracted term interference term $2(P_{signal} \times P_{reference})^{1/2}$.

Because the speckle phases are random, according to the known principles of parallel speckle detection in UOT or in wavefront measurement from strongly scattering media, it is known that a single-pixel detector will not scale to high signal to noise ratios. In particular, the aggregate signal over a large single-pixel detector would scale as the square root of detector size, but so would shot noise in the background, and hence the signal to noise ratio performance of a large detector would not increase with detector size. In contrast, as described in the equations below, with lock-in detection at each detector (or pixel), the aggregate signal scales linearly with the number of pixels, while the aggregate background shot noise scales as the square root, and hence signal to noise performance increases as the square root of the number of pixels, giving a strong advantage for using large numbers of pixels.

It can be assumed that the amplitude of $P_{reference}$ is much greater than the amplitude of $P_{background}$, and the amplitude of $P_{signal}$ is naturally much less than the amplitude of $P_{reference}$, since the ultrasound tagged signal light 44 originates from a very small target voxel 14 within the tissue and the tagging efficiency (i.e., the number of tagged photons relative to a number of untagged photons scattered by the target voxel 14) within that target voxel 14 is a small fraction. Thus, only interference terms containing $P_{reference}$ are significant in the sum representing the intensity measured by each pixel (i.e., $P_{background} + P_{signal} + P_{reference} + 2(P_{signal} \times P_{reference})^{1/2} \times \cos(\varphi_{control} - \varphi_{unknown1}))$.

Therefore, the dominant signal source contributing to detection has the following number of photons impinging on one pixel:

$$\text{dominant signal} = (\varepsilon/hv) \times 2(P_{signal} \times P_{reference})^{1/2} \tau; \quad [4]$$

and the dominant noise source in the quadrature measurement of this amplitude is due to the shot noise in the reference light 42, and has the following number of photons impinging on each pixel:

$$\text{dominant noise} = ((\varepsilon/hv) \times P_{reference} \times \tau)^{1/2}; \quad [5]$$

where $\varepsilon$ is a detector efficiency scaling factor, P is the power for each of the ultrasound tagged photons, hv is the per-photon energy (with h as Plank's constant, and v as the frequency of the light), and t is the integrated pulse widths used in the measurement.

With a number of pixels N, the signal-to-noise ratio (SNR) scales with $N^{1/2}$, since the total shot noise grows as $N^{1/2}$, whereas the total signal grows as N, so that:

$$\text{SNR}_{N\ pixels} = (N \times (\varepsilon/hv) \times \tau \times P_{signal})^{1/2}, \quad [6]$$

which shows that the SNR improves with increasing number of pixels in the lock-in camera 28. Thus, the Poisson nature of photon shot noise statistics is being utilized to determine the fundamental signal to noise ratio.

It should be appreciated that although the UOT system 10 has been described as using a 4-bin quadrature detection scheme to reconstruct the amplitude of the signal light 44 from the interference light patterns 48, and therefore, utilizes four bins 70 (and four optical pulses) for each detector 68 (or pixel) of the lock-in camera 28 to store the intensity values of the respective four interference patterns 48 over the four different phases, the UOT system 10 may utilize less than four phases (e.g., three phases equal to 0, $2\pi/3$, and $4\pi/3$), or may even utilize two phases (e.g., 0 and $\pi$) to reconstruct the amplitude of the signal light 44 from the interference light patterns 48, and therefore utilizes three bins 70 (and three optical pulses) or only two bins 70 (and only two optical pulses) for each detector 68 (or pixel) to store the intensity values of the respective interference patterns 48 over the phases. It should further be appreciated that although the phases of the 4-bin quadrature scheme, as well as the three-bin and two-bin detection schemes, have been described as being equally spaced, the phases used in any of these detection schemes can be unequally spaced. For example, for the three-bin detection scheme, the phases can be selected to be 0, $\pi$, and $4\pi/3$, or for a two-bin detection scheme, the phases can be selected to be 0 and $4\pi/3$.

In the case of a two-bin detection scheme, rather than obtaining a quadrature amplitude from each pixel 68, the power of the signal light 44 can be computed as the absolute difference between the two intensity values stored in the two bins 70 for each pixel 68 and then averaged.

In particular, the power detected at a single detector 68 (or pixel) for each optical pulse at one of the two phases can computed by expanding equation [2] for two phases of 0 and 180 degrees, as follows:

$$\text{Value}_{1,k} = P_{background} + P_{signal} + P_{reference} + 2(P_{signal} \times P_{reference})^{1/2} \times \cos(0 - \varphi_{unknown}),\ \text{and} \quad [6]$$

$$\text{Value}_{2,k} = P_{background} + P_{signal} + P_{reference} + 2(P_{signal} \times P_{reference})^{1/2} \times \cos(\pi - \varphi_{unknown}), \quad [7]$$

where $Value_1$ is the intensity value in the first bin 70 of the respective pixel k, and $Value_2$ is the intensity value in the second bin 70 of the respective pixel k.

It is noted that the term $P_{background}+P_{signal}+P_{reference}$ in each of equations [6] and [7] represents the DC terms of the two interference light patterns, whereas the terms $2(P_{signal} \times P_{reference})^{1/2} \times \cos(\varphi_{control}-\varphi_{unknown})$ and $2(P_{signal} \times P_{reference})^{1/2} \times \cos(\varphi_{control}-\varphi_{unknown}+\pi)$ in the respective equations [6] and [7] represent the AC beat patterns of the interference light patterns 48, which differ in phase by 180 degrees, such that they sum to zero.

The terms $P_{background}+P_{signal}+P_{reference}$ are constant across the two phases, and thus, can be eliminated by taking the difference of the intensity values $Value_{1,k}$ and $Value_{2,k}$, leaving only the difference of the interference terms, as $2(P_{signal} \times P_{reference})^{1/2} \times \cos(\varphi_{control}-\varphi_{unknown})-2(P_{signal} \times P_{reference})^{1/2} \times \cos(\varphi_{control}-\varphi_{unknown}+\pi)$, which can be summed over all of the k pixels and then averaged in accordance with the following equation:

$$2(P_{signal} \times P_{reference})^{1/2} = (\Sigma k |Value_{1,k}-Value_{2,k}|)/N \text{ across all } k=1,2,\ldots N \text{ speckles or pixels,} \quad [8]$$

the average across all pixels of the absolute value of the difference across corresponding pixels. Based on known scaling relationship between the power of the reference light $P_{reference}$ and the power of the signal light $P_{signal}$ discussed above, the power of the $P_{signal}$ can be expressed as:

$$P_{signal} \propto (\Sigma k |Value_{1,k}-Value_{2,k}|)/N, \quad [9]$$

i.e., the average across all pixels of the absolute value of the difference across corresponding pixels.

It should be noted that sign-rectifying operations of the intensity value differences other than taking the absolute can be utilized to obtain the power of the signal light 44. For example, a squaring operation can be applied to the intensity value differences. Thus, the power of the signal light 44 can alternatively be computed as the square of the difference between the two intensity values stored in the two bins 70 for each pixel 68 and then averaged in accordance with the following equation:

$$P_{signal} \propto (\Sigma k (Value_{1,k}-Value_{2,k})^2)/N \text{ across all } k=1,2,\ldots N \text{ speckles or pixels.} \quad [10]$$

Thus, it can be appreciated that the intention of the two-bin measurement is to arrive at a precise estimate of power of the signal light $P_{signal}$ up to the aforementioned scaling relationship defined by the strength of the reference light $P_{reference}$, by removing the terms that are constant between the two measurements of the lock-in camera 28, and removing the unknown speckle-specific phases, and instead extracting only the amplitude of the cosine term. In the context of the UOT, just as with the quadrature detection scheme described above, the two-bin detection scheme serves as a measurement of light absorption at a single spatial voxel within the tissue.

However, the two-bin detection scheme represents a simplification that leads to only a small constant decrease factor in the signal to noise ratio. The dominant signal source contributing to detection has the following number of photons impinging on one pixel:

$$\text{dominant signal}=(\varepsilon/h\nu) \times B \times \tau/2 \times |\cos(0+\varphi)-\cos(\pi+\varphi)|_{average\ over\ \varphi\ in\ [0,2\pi]}; \quad [11]$$

and the dominant noise source in the two-bin measurement of this amplitude is due to the shot noise in the reference light 42, and has the following number of photons impinging on one pixel:

$$\text{Dominant Noise}=(\varepsilon t/H\nu)^{1/2} \times (2/\pi) B/A^{1/2}, \quad [12]$$

where A and B are constants in the equation $A+B(\cos \varphi)$, B is proportional to the number of tagged photons per detector 68, $\varepsilon$ is a detector efficiency scaling factor, $h\nu$ is the per-photon energy (with h as Plank's constant, and $\nu$ as the frequency of the light), and $\tau$ is the integrated pulse widths used in the measurement, and $\varphi$ is a random, pixel-specific speckle phase.

With a number of pixels N, the signal-to-noise ratio (SNR) scales with $N^{1/2}$, since the total shot noise grows as $N^{1/2}$, whereas the total signal grows as N, so that:

$$SNR_{N\ pixels}=(N \times (\varepsilon \tau/h\nu)^{1/2} \times (2/\pi) \times B/A^{1/2}, \quad [13]$$

which shows that, just as in the quadrature detection scheme, the SNR improves with increasing number of pixels in the lock-in camera 2828, and the Poisson nature of photon shot noise statistics is being utilized to determine the fundamental signal to noise ratio.

Notably, the use of a two-bin detection scheme, rather than the four-bin quadrature scheme, provides the advantage that only two optical pulses, as opposed to four optical pulses, needs to be generated, thereby shortening the time period needed to take a measurement of the target voxel 14, and thus, alleviating the speckle decorrelation time limitation.

Although the UOT system 10 has been described as computing the intensity values $Value_k$ of the speckle grains of each interference light pattern 48 in order to obtain the power of the light signal $P_{signal}$, it should be appreciated that the UOT system 10 may alternatively or optionally compute the random phases $\varphi_{unknown}$ of the kth speckle grains of each interference light pattern 48 in order to obtain the phase across the wavefront of the light signal.

For example, in an optional embodiment, a digital optical phase conjugation (DOPC) technique can be used to boost the sensitivity of the pulsed UOT detection. DOPC can be performed in the context of schemes that rely on time reversal based optical phase conjugation using "guidestars" localized in three dimensions, for instance, using schemes, such as Time Reversal of Ultrasound-Encoded Light (TRUE) (see, e.g., Xu X, Liu H., Wang L V, "Time-Reversed Ultrasonically Encoded Optical Focusing into Scattering Media," Nature Photonics, Vol. 5, No. 3, pp. 154-157 (Mar. 1, 2011); Wang Y M, Judkewitz B, DiMarzio C A, Yang C., "Deep-Tissue Focal Fluorescence Imaging with Digitally Time-Reversed Ultrasound-Encoded Light," Nature Communications, Vol. 3, Article 928 (Jun. 16, 2012); Horstmeyer R., Ruan H, Yang C, "Guidestar-Assisted Wavefront-Shaping Methods for Focusing Light into Biological Tissue," Nature Photonics, Vol. 9, No. 9, pp. 563-571 (Sep. 1, 2015).

These methods are used to focus light to a guide-star-defined point deep inside a scattering medium, by measuring the wavefront emanating from the guidestar and digitally time-reversing (e.g., phase conjugating) light in order to cause the light to "play back" its path through the scattering medium and come to focus at the guidestar position. In the context of UOT, the guidestar is the focal point of an ultrasound beam. In these methods, the phase of a tagged light field originating from a given three-dimensional guidestar voxel in the brain is measured using demodulation and quadrature detection, and then an approximate phase-conjugate, i.e., approximate time-reverse light field, possibly amplified in intensity, is "played back" to focus light to the three-dimensional guidestar location despite the effects of strong or even diffusive scattering in the tissue.

Figure 9B:
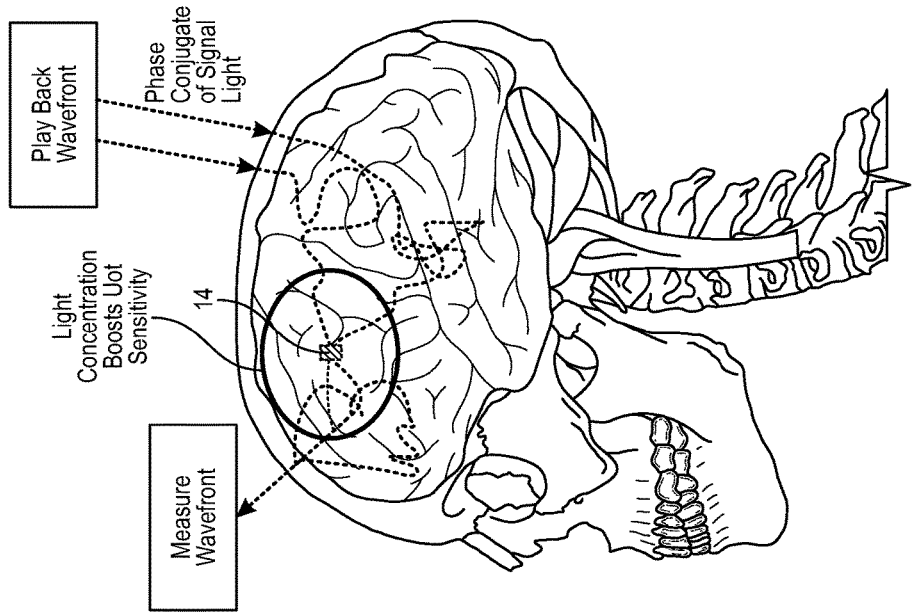
FIG. 9b is a schematic diagram of a modified UOT system of FIG. 1, particularly showing playback of a phase conjugate of the wavefront of signal light.
Figure 9A:
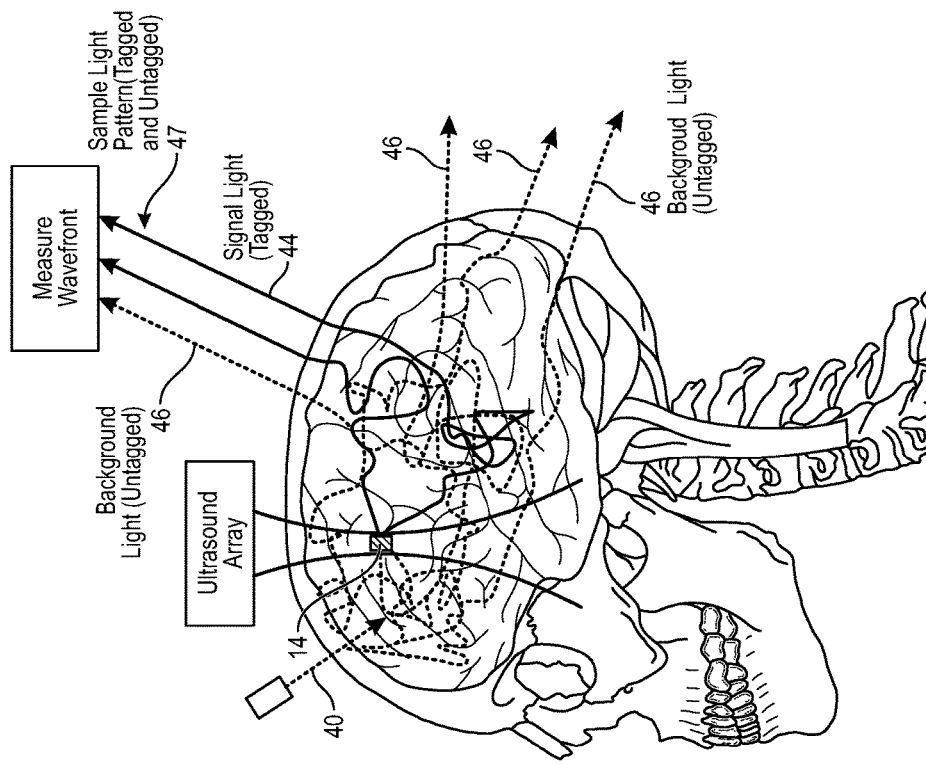
FIG. 9a is a schematic diagram of a modified UOT system of FIG. 1, particularly showing a detection of a wavefront of signal light.

In the context of the UOT system 10 described herein, the phase of the wavefront of the signal light 44 originating from the target voxel 14 (i.e., the guidestar) is measured using the pulsed UOT detection scheme described above, as illustrated in FIG. 9a, with the exception that, in addition to extracting the power of the wavefront of the $P_{signal}$, the unknown phase $\varphi_{unknown}$ of the wavefront of the signal light 44 is extracted using the known principles of quadrature detection. As illustrated in FIG. 9b, the wavefront of the signal light 44 is then amplified and retransmitted back in the opposite direction and focused onto the target voxel 14 (i.e., the guidestar), where it is tagged by the ultrasound 32 and may then be detected by the same or another lock-in camera so as to perform the process iteratively. The retransmission should be timed such that the light through the voxel is coincident in time with an ultrasound pulse passing through the voxel.

Figure 10A:
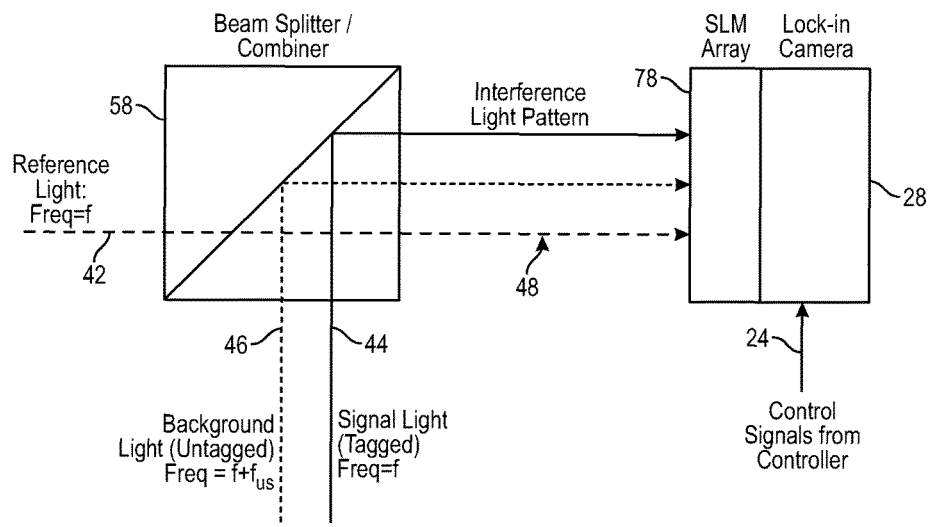
FIG. 10a is a block diagram of one embodiment of a phase conjugation array that can be incorporated into the UOT system of FIG. 1, particularly showing detection of the signal light.

Referring to FIG. 10a, the phase of the signal light 44 extracted in the pulsed UOT detection scheme may be used in conjunction with a spatial light modulator (SLM) array 78 that is co-registered (e.g., pixel-by-pixel) with the lock-in camera 28 to perform optical phase conjugation of the signal light 44 (see, e.g., Laforest T, Verdant A, Dupret A, Gigan S., Ramaz F, Tessier G, "Co-Integration of a Smart CMOS Image Sensor and a Spatial Light Modulator for Real-Time Optical Phase Modulation," Proc. Of SPIE-IS&T, Vol. 2014, 9022:90220N-1 (March 2014).

The SLM array 78 may include any of a number of different amplitude and/or phase modulator structures, such as liquid crystals, re-positionable microelectromechanical systems (MEMS) mirrors, ferroelectrics, digital micro-mirror device pixels, among others. In one embodiment, the SLM array 78 may be semi-transparent (e.g., a liquid crystal modulator backed by a partial reflector), and can be inserted into the light path between the entry of the reference light 42 and the lock-in camera 28. The SLM array 78 may be built directly on top of the lock-in camera 28 to create a phase conjugation array, with this arrangement being similar to the pulsed UOT detection scheme described above.

Figure 10B:
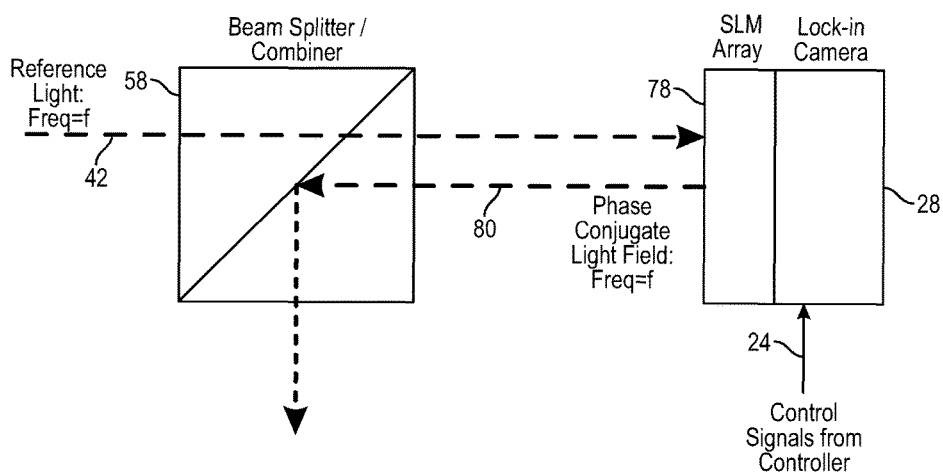
FIG. 10b is a block diagram of the phase conjugation array of FIG. 10a, particularly showing playback of a phase conjugation light field.

Referring to FIG. 10b, post-detection, each pixel 68 of the lock-in camera 28 will send the conjugate phase information to the SLM array 78 (conjugate phase information being the negative of the detected phase). Each pixel may have internal electronics (e.g., transistors) that compute and sends the desired phase adjustment as an electrical voltage to adjust the corresponding pixel phase or amplitude of the SLM array 78. In a phase-only optical phase conjugation scheme, each pixel of the phase conjugation array will simply "actuate" the conjugate phase, such that light reflected from the pixel will accrue the phase. Amplitude-only phase conjugation can alternatively be performed by reflecting or not reflecting the input light based on the conjugate phase information. In aggregate, the same reference light 42 used in the detection process (while blocking the sample light 40) or light precisely aligned with the reference light 42 will reflect off the phase conjugation array to create a phase conjugate light field 80 that will focus back to the target voxel 14.

The improvement in contrast of this return light 80 (i.e., the phase conjugate light field) to the target voxel 14 is given by: Contrast A=$\alpha$*((N−1)/M+1), wherein N is the number of input optical modes (or the number of photons if less than the number of input optical modes), which is approximately equal to the number of pixels on the phase conjugation array); M is the number of target optical modes in the target voxel 14, and a equals 1 when a full phase and amplitude conjugation is performed, and is some value smaller than 1 when a phase only, amplitude only, and/or coarse grain phase conjugation is performed. The term "coarse grain," in this context, means that the phase playback at each pixel can take only a finite number of possible values.

The phase conjugation process can be iterated many times, each time taking the light field, resulting from the last step, and phase conjugating that scattered light field. The contrast improvement can be expected to grow as (contrast A)$^K$, where K is the number of iterations. Thus, the number of photons traveling through the target voxel 14 can be exponentially amplified, thereby improving the effective modulation depth of the UOT (i.e., the fraction of the ultrasound tagged photons reaching the detector). The addition of phase conjugation to the pulsed UOT system 10 could be used to increase the number of collected tagged photons, increase modulation depth, or decrease ultrasound intensity or duty cycle requirements.

Besides detecting random phases $\varphi_{unknown}$ of the kth speckle grains of each interference light pattern 48 in order to obtain the phase across the wavefront of the light signal for purposes of performing DOPC, the UOT system 10 may detect random phases $\varphi_{unknown}$ of the kth speckle grains of each interference light pattern 48 for other purposes, such as detecting faster signals due to light scattering, as opposed to light absorption changes. For example, the phase of each kth speckle grain of signal light may be determined using quadrature detection (i.e., four bins) in accordance with the equation:

$$\varphi = \arctan(Value_{1,k} - Value_{3,k})/(Value_{2,k} - Value_{4,k}), \quad [14]$$

where $Value_{1,k}$ is the intensity of the kth speckle grain of the interference light pattern 46a at a phase of 0, $Value_{2,k}$ is the intensity of the kth speckle grain of the interference light pattern 46b at a phase of $\pi/2$, $Value_{3,k}$ is the intensity of the kth speckle grain of the interference light pattern 46c at a phase of $\pi$, and $Value_{4,k}$ is the intensity of the kth speckle grain of the interference light pattern 46d at a phase of $3\pi/2$.

Alternatively, the phase of each kth speckle grain of signal light may be determined using other phase estimation techniques. For example, a discretized phase of each kth speckle grain of signal light may be determined, e.g., in the range of $\pi/2$ to $3\pi/2$ versus $-\pi/2$ to $-3\pi/2$. In any event, the phases of the wavefront of the signal light can be repeated to determine temporal changes in the wavefront phases, and the magnitude of such temporal phase changes can be computed over the kth speckle grains of the signal light. In this manner, the UOT system 10 may be sensitive to changing optical phases in the target voxel 14 due to optical scatter changes, which are indicative of neural activity.

Performance estimates for the UOT system 10 described herein in the detection of a blood-oxygen-level dependent signal in the brain through the skull as a function of the number of pixels in the lock-in camera 28 used (in this case, 10 million pixels or higher) indicate that neural activity dependent changes in the blood-oxygen-level dependent signal could be detected at hundreds to thousands of voxels per 100 millisecond temporal sample. In this calculation, the use of a 2 MHz ultrasound, and thus a spatial resolution on the order of ½ millimeter, is assumed, exceeding the spatial resolution of traditional blood-oxygen-level dependent signal measurements, like functional MRI (fMRI), and vastly exceeding the many millimeter to multiple centimeter-scale spatial resolution of diffuse optical tomography, including time-gated forms of diffuse optical tomography. In this calculation, it is further assumed that millions of tagged photons must be collected from the target voxel 14 per temporal sample in order to measure naturally occurring blood-oxygen-level dependent signals functional changes in the human brain, which are on the order of small fractions of a percent, while overcoming shot noise fluctuations in the number of detected tagged photons.

In one embodiment, the processor 30 utilizes blood-oxygen-level dependent signals detected by the lock-in camera 28 to determine the neural activity in the brain; that is, blood-oxygen-level dependent signals provide a sense of the level of deoxygenated and/or oxygenated hemoglobin concentration or relative abundance in the target voxel 14 in the brain, and given the known coupling between cerebral hemodynamics and neuronal activity, the processor 30 can thereby determine the extent of neuronal activity in that target voxel 14. In another embodiment, the UOT system 10 detects blood-oxygen-level dependent signals over multiple wavelengths of the sample light, in which case, the processor 30 may determine and compare the optical absorption characteristics of the target voxel 14 of blood-oxygen-level dependent signals over the different wavelengths of sample light in order to determine the level of deoxygenated and/or oxygenated hemoglobin concentration or relative abundance present in the target voxel 14 according to known principles of functional infrared spectroscopy, for instance by solving two equations in two unknowns relating the measured absorption at two wavelengths to the level of deoxygenated and/or oxygenated hemoglobin concentration or relative abundance in the blood, or alternatively several equations in several unknowns representing absorption at several wavelengths in order to determine the concentrations of several molecular species in the target voxel 14.

Figure 11:
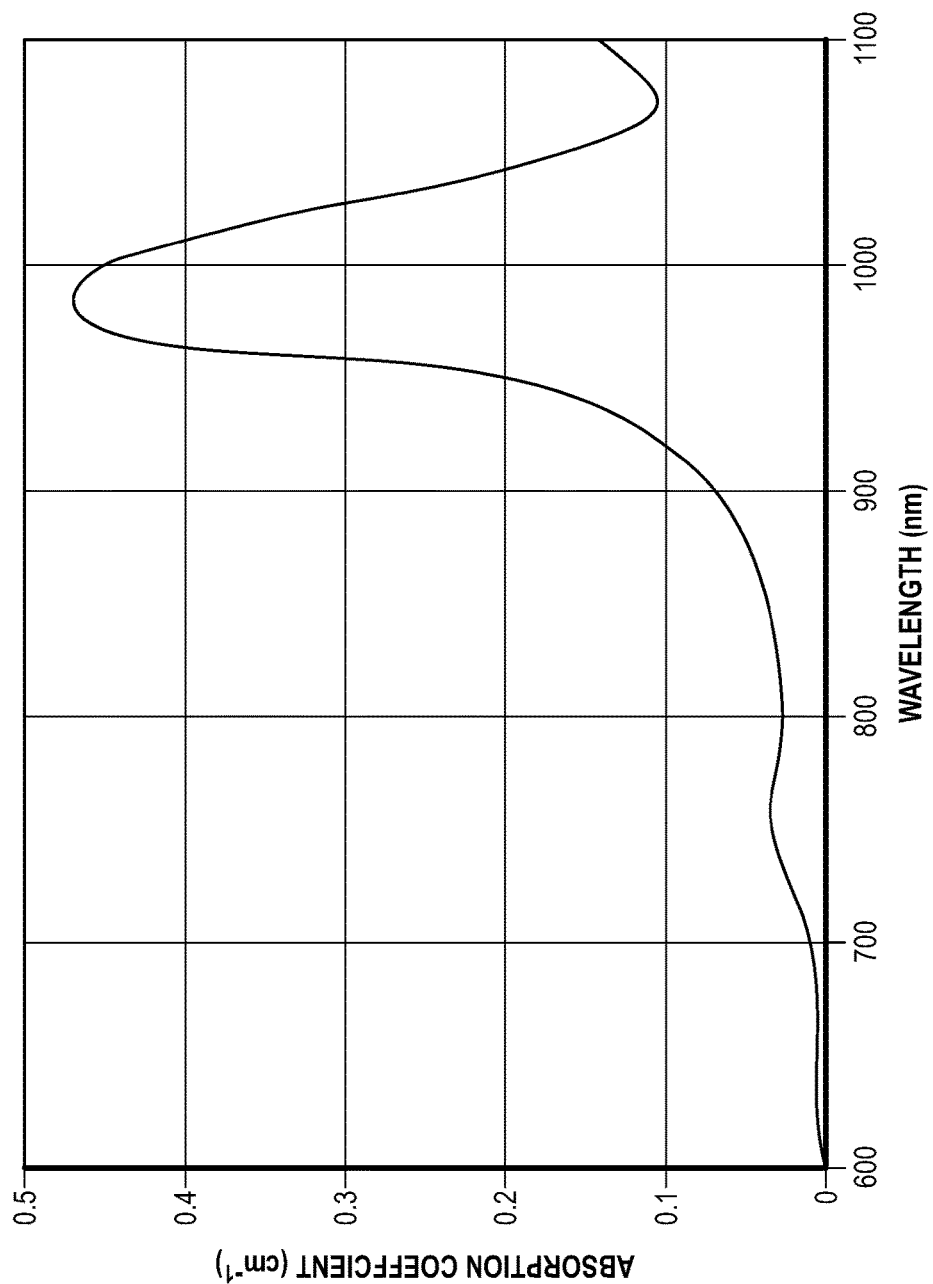
FIG. 11 is a plot of the absorption of light in water over the wavelength of light.

In one particularly advantageous embodiment, instead of detecting blood-oxygen-level dependent signals, the processor 30 may detect faster signals of neuronal activity, such as in the brain, to determine the extent of neuronal activity in the target voxel 14. Neuronal activity generates fast changes in optical properties, called "fast signals," which have a latency of about 10-100 milliseconds and are much faster than the metabolic (approximately 100-1000 milliseconds) and hemodynamic (hundreds of milliseconds to seconds) evoked responses (see Franceschini, M A and Boas, D A, "Noninvasive Measurement of Neuronal Activity with Near-Infrared Optical Imaging," Neuroimage, Vol. 21, No. 1, pp. 372-386 (January 2004)). Additionally, is believed that brain matter (e.g., neurons and the extracellular matrix around neurons) hydrates and dehydrates as neurons fire (due to ion transport in and out of the neurons), which could be measured via determining the absorption characteristics of water in the target voxel 14. In this case, it is preferred that the target voxel 14 be minimized as much as possible by selecting the appropriate ultrasound frequency (e.g., two to six times the size of a neuron, approximately 100 micrometers) in order to maximize sensitivity to highly localized changes in fast indicators of neural activity. As illustrated in FIG. 11, the optical absorption coefficient of water is relatively high for wavelengths of light in the range of 950 nm-1080 nm. Thus, for maximum sensitivity to changes in optical absorption of tissue due to changes in the level of water concentration or relative water concentration in the brain matter, it is preferred the wavelength of the sample light be in the range of 950 nm-1080 nm.

Regardless of the nature of the detected signal and physiologically-dependent optical parameter, the processor 30 may optionally use a computational model of light propagation in the tissue, and deconvolution or inverse problem optimization methods/algorithms, to improve the spatial resolution of the resulting measurement. Empirical measurements of a sample may be compared to those predicted by a model of the spatial layout of absorbers of the sample incorporating an effective point spread function of detection, such that the model may be improved to obtain an optimal match between the model predictions and the observed signals from the sample (see Powell S., Srridge S R, Leung T S, "Gradient-Based Quantitative Image Reconstruction in Ultrasound-Modulated Optical Tomography: First Harmonic Measurement Type in a Linearized Diffusion Formulation," IEEE Transactions on Medical Imaging, Vol. 35, No. 2, pp. 456-467 (February 2016).

Although the UOT system 10 has been described herein as acquiring only one measurement of the target voxel 14, it should be appreciated that the UOT system 10 may acquire multiple measurements of the target voxel 14 over time that yields a time trace indicative of time varying physiologically depending optical properties in the target voxel 14, such as time-varying optical absorption in the target voxel 14 due to functional changes in the brain. Optionally, two time traces of the target voxel 14 can be acquired, one time trace being generated with the ultrasound 32 turned on at regular intervals in the same manner described above, and another time trace generated with the ultrasound 32 turned off at regular intervals. For example, a measurement of the target voxel 14 may be acquired when the ultrasound 32 turned on to create a first data point on the first time trace; a measurement of the target voxel 14 may be acquired when the ultrasound 32 turned off to create a first data point on the second time trace; a measurement of the target voxel 14 may be acquired when the ultrasound 32 turned on to create a second data point on the first time trace; a measurement of the target voxel 14 may be acquired when the ultrasound 32 turned off to create a second data point on the second time trace; and so forth. The second time trace may provide a baseline null signal measurement trace, which is useful for tracking secondary variations distinct from the first time trace's signal variations due to the ultrasound 32.

Figure 12:
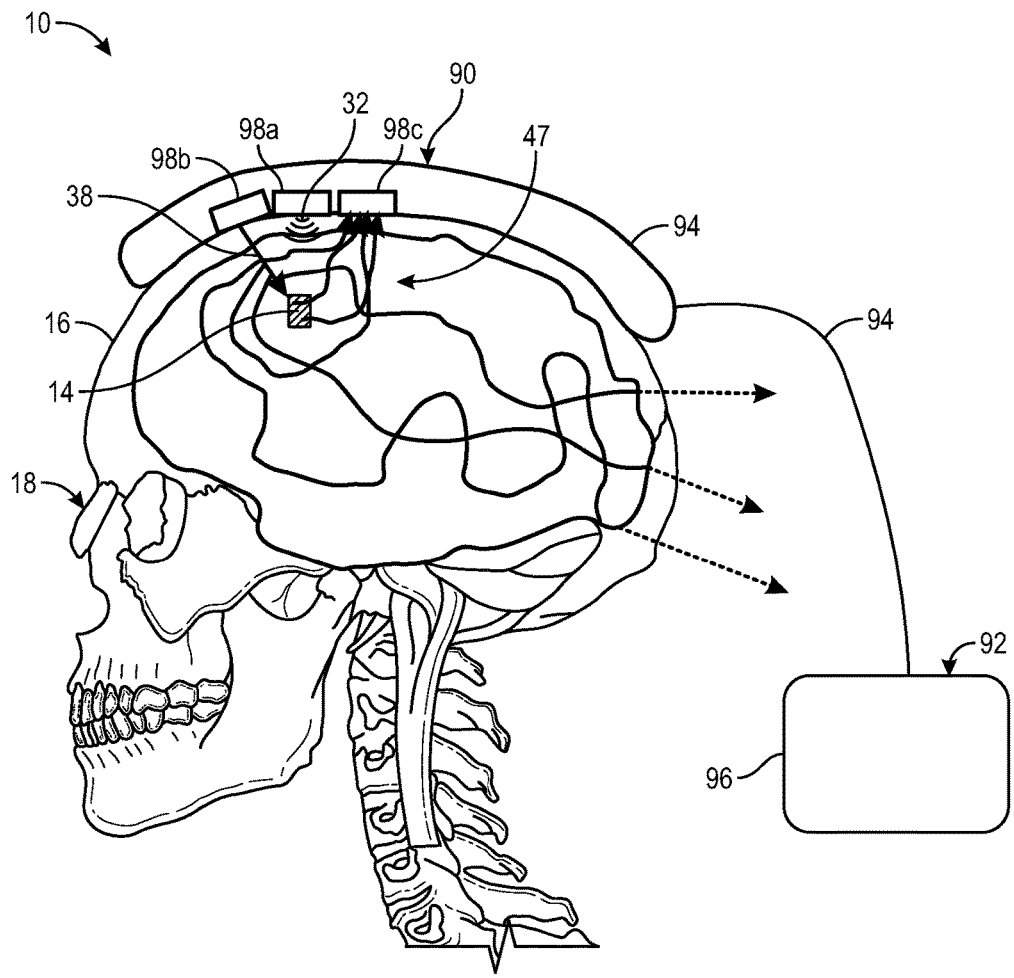
FIG. 12 is a plan view of wearable and unwearable units in which the UOT system of FIG. 1 may be embodied.

Referring now to FIG. 12, the physical implementation of the UOT system 10 will be described. As there shown, the UOT system 10 includes a wearable unit 90 that is configured for being applied to the patient 18, and in this case, worn on the head of the patient 18, and an auxiliary head-worn or not head-worn unit 92 coupled to the wearable unit 90 via a wired connection 94 (e.g., electrical wires). Alternatively, the UOT system 10 may use a non-wired connection (e.g., wireless radio frequency (RF) signals) for providing power to or communicating between components of the respective wearable unit 90 and auxiliary unit 92.

In the illustrated embodiment, the wearable unit 90 includes a support structure 94 that either contains or carries the transducer arrangement 34 of the acoustic assembly 20 (shown in FIG. 2), the interferometer 22, and the lock-in camera 28. The wearable unit 90 may also include an output port 98a from which the ultrasound 32 generated by the acoustic assembly 20 (shown in FIG. 1) is emitted, an output port 98b from which the sample light 40 generated by the interferometer 22 (shown in FIG. 1) is emitted, and an input port 98c into which the sample light pattern 47 comprising the tagged signal light and untagged background light are input into the interferometer 22. It should be appreciated that although the input port 98c is illustrated in close proximity to the input ports 98a, 98b, the proximity between the input port 98c and the output ports 98a, 98b may be any suitable distance. The support structure 94 may be shaped, e.g., have a banana, headband or hat shape, such that the ports 98 are in close contact with the outer skin of the body part, and in this case, the scalp of the head 16 of the patient 18. An index matching fluid maybe used to reduce reflection of the light generated by the light source 30 source 50 of the interferometer 22 from the outer skin, and an ultrasound transmitting adhesive or acoustic coupling material can be used to facilitate conduction of the ultrasound 32 into the body part. An adhesive or belt (not shown) can be used to secure the support structure 94 to the body part.

The auxiliary unit 92 includes a housing 96 that contains the controller 24 and the processor 30 (shown in FIG. 1). The auxiliary unit 92 may additionally include a power supply (which if head-worn, may take the form of a rechargeable or non-chargeable battery), a control panel with input/output functions, a display, and memory. The auxiliary unit 92 may further include the signal generator 36 of the acoustic assembly 20, as well as any drive circuitry used to operate the interferometer 22.

The interferometer 22 and lock-in camera 28 are preferably mechanically and electrically isolated from the acoustic assembly 20, such that the emission of the ultrasound 32 by the acoustic assembly 20, as well as the generation of RF and other electronic signals by the acoustic assembly 20 minimally affects the detection of the optical signals by the interferometer 22 and generation of data by the lock-in camera 28. The wearable unit 90 may include shielding (not shown) to prevent electrical interference and appropriate materials that attenuate the propagation of acoustic waves through the support structure 94.

Having described the arrangement of function of the UOT system 10, one method of operating the UOT system on a patient will now be described. In this method, ultrasound 32 is delivered into the target voxel 14 in the anatomical structure 16, and sample light 40 is delivered into the anatomical structure 16, wherein a portion 40a of the sample light 40 passing through the target voxel 14 is scattered by the anatomical structure 16 as the signal light 44, and another portion 40b of the sample light 40 not passing through the target voxel 14 is scattered by the anatomical structure 16 as background light 46 that combines with the signal light 44 to create the sample light pattern 47. As exemplified above, the anatomical structure 16 may be an intact head comprising the scalp, skull, and brain matter. Due to the high resolution of the UOT system 10, the target voxel 14 may be smaller than one $mm^3$.

The reference light 42 is combined with the sample light pattern 47 to generate an interference light pattern 48 (e.g., in a homodyne manner), and in this method, a speckle light pattern. The ultrasound 32 and sample light 40 are pulsed in synchrony, such that only the signal light 44 is shifted (i.e., tagged) by the ultrasound 32. That is, as described above, each pulse of the sample light 40 will pass through the target voxel 14 only as the ultrasound 32 passes through the target voxel 14, such that no portion of the background light 46 will be tagged by the ultrasound 32. The interference light pattern 48 is sequentially modulated to generate a plurality of different interference light patterns 48. The spatial components of any particular interference light pattern 48 can then be simultaneously detected, and a plurality of values can be stored in the respective bins 70 (either in bins 70a, in bins 70b, in bins 70c, or bins 70d) of the detectors 68. The values are representative of the spatial component for the respective interference light pattern 48. The physiologically-dependent optical parameter of the target voxel 14 is then determined based on the spatial component values stored in the bins 70. Due to the high speed of the lock-in camera 28, the spatial components for any particular interference light pattern 48 may be simultaneously detected and stored in the respective bins 70 very quickly. For example, in one embodiment, the spatial components for any particular interference light pattern 48 may be simultaneously detected, and the resulting spatial component values for all the interference light patterns 48 are stored in the respective bins 70 within 1 millisecond. In another embodiment, the spatial components for any particular interference light pattern 48 may be simultaneously detected, and the resulting spatial component values for all the interference light patterns 48 are stored in the respective bins 70 within 1 microsecond to 1 millisecond.

Although the UOT system 10 has been described as non-invasively imaging one target voxel 14 at a time, the UOT system 10 may be modified to image multiple target voxels 14 at a time. For example, in one particular embodiment, an acoustic assembly may simultaneously generate multiple foci in parallel (i.e., focuses the ultrasound on multiple target voxels at the same time), with each ultrasound focus being modulated at a different optical frequency (e.g., $f_1-f_{us}$, $f_2-f_{us}$, $f_3-f_{us}$, etc.), with separate frequency-shifted reference light (e.g., $f_1$, $f_2$, $f_3$, etc.) being used to interfere with the resulting signal light in a homodyne manner. Separate lock-in cameras may be utilized to detect the different interference patterns corresponding to the different target voxels.

Figure 13:
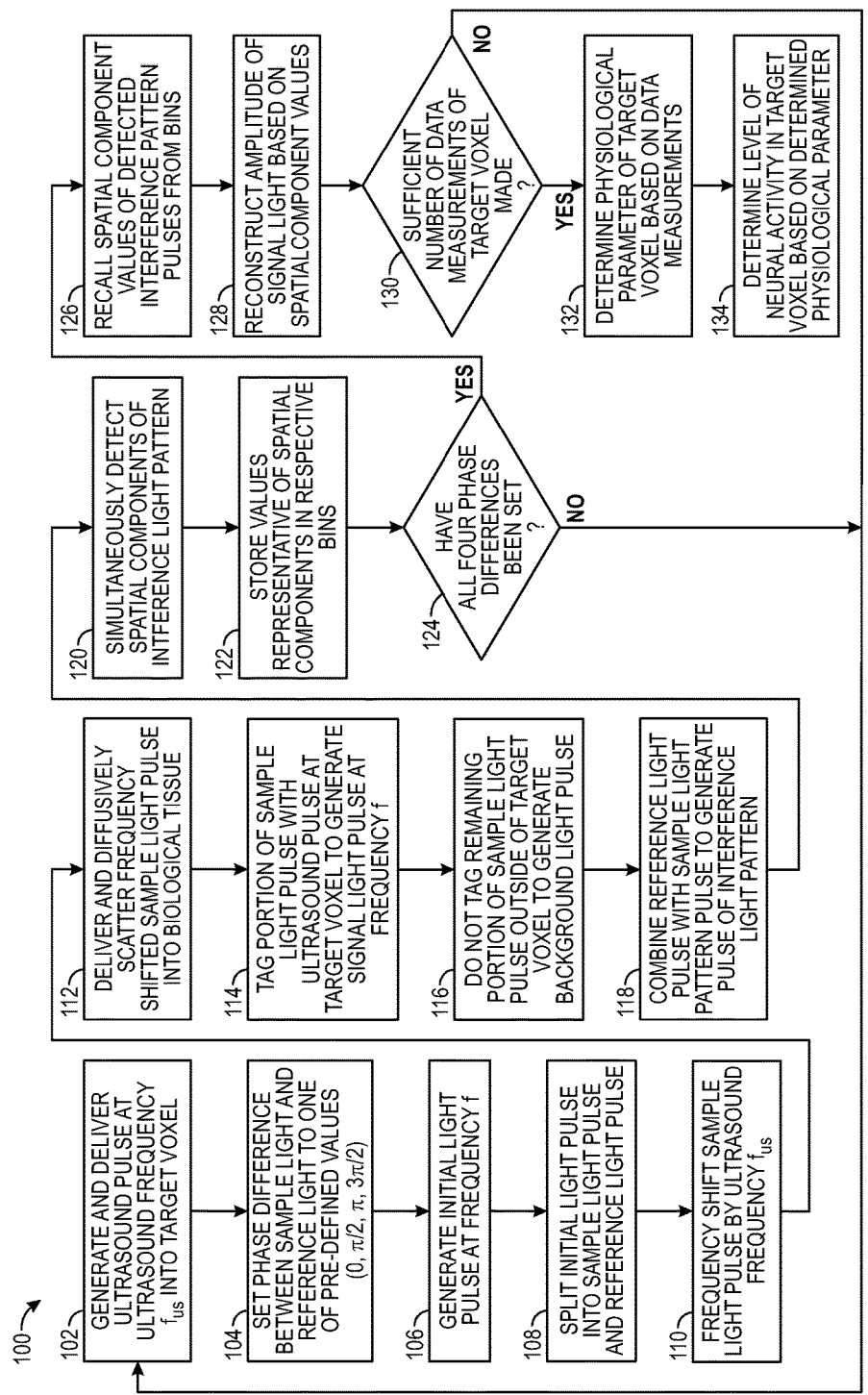
FIG. 13 is a flow diagram of one method used by the UOT system of FIG. 1 to non-invasively measure a physiologically-dependent optical parameter using the pulse sequence of FIG. 5.

Referring to FIG. 13, one particular method 100 performed by the UOT system 10 to non-invasively image the target voxel 14 in anatomical structure 16 will now be described. This particular method 100 implements the pulsing sequence of FIG. 5.

The controller 24 operates the acoustic assembly 20 to generate and deliver a pulse of ultrasound 32 having a frequency $f_{us}$ (initially, ultrasound pulse $U_a$ illustrated in FIG. 5) into the anatomical structure 16, e.g., by sending a control signal to the signal generator 36 to pulse an electrical signal on and off (step 102). The controller 24 sets the phase difference between the sample light 40 and the reference light 42 to one of the four pre-defined values (0, $\pi/2$, $\pi$, and $3\pi/2$) by sending a control signal to the phase shifter 54 of the interferometer 22 (step 104). This pre-defined phase difference value may be first set to 0. Next, the controller 24 operates the interferometer 22 to generate and emit a pulse of source light 38 having a frequency f, e.g., by sending a control signal to the drive circuit to pulse the light source 50 on and off (step 106). The interferometer 22 (e.g., via the beam splitter 52) splits the pulse of source light 38 into a pulse of sample light 40 (initially, the sample light pulse $L_a$ illustrated in FIG. 5) and a pulse of reference light 42 (step 108).

The wavelength (and thus, the frequency f) of the source light 38 may be selected based on the physiologically-dependent optical parameter to be ultimately determined. For example, if the physiologically-dependent optical parameter is the level of deoxygenated and/or oxygenated hemoglobin concentration or relative abundance, the wavelength of the source light 38 may be in the range of 605 nanometers to 950 nanometers, whereas if the physiologically-dependent optical parameter to be determined is a water absorption level (level of water concentration or relative water concentration), the wavelength of the source light 38 may be in the range of 950-1080 nanometers.

Next, prior to the pulse of sample light 40 entering the anatomical structure 16, the controller 24 operates the interferometer 22 to frequency shift the pulse of sample light 40 by the ultrasound frequency $f_{us}$, e.g., by sending a control signal to the frequency shifter 56, resulting in the pulse of sample light 40 having a frequency $f-f_{us}$ (step 110). It should be appreciated that, although this frequency shifting technique implements the frequency shifting technique illustrated in FIG. 3a, other frequency shifting techniques can be utilized, such as those illustrated in FIGS. 3b-3d. The frequency-shifted pulse of sample light 40 is then delivered into and diffusively scattered within the anatomical structure 16 (step 112). As the pulse of frequency shifted sample light 40 scatters diffusively through the anatomical structure 16, a portion will pass through the target voxel 14 and be frequency shifted (i.e., tagged) back to its original frequency f by the pulse of ultrasound 32 passing through the target voxel 14, resulting in a pulse of scattered signal light 44 having the same frequency f (step 114); and the remaining portion will not pass through the target voxel 14, and thus will not be frequency shifted by the pulse of ultrasound 32, resulting in a pulse of scattered background light 46 having a frequency $f-f_{us}$ (the same frequency as the frequency shifted sample light 40 prior to entering the anatomical structure 16) that combines with the pulse of signal light 44 to create a pulse of a sample light pattern 47 (step 116).

Next, the interferometer 22 then combines (e.g., via the light combiner 58) the pulse of reference light 42 with the pulse of the sample light pattern 47 to generate a pulse of an interference light pattern 48 (initially, the interference light pattern pulse $I_a$ illustrated in FIG. 5) (step 118). Then, under control of the controller 24, all of the detectors 68 (FIG. 4) of the lock-in camera 28 simultaneously detect respective spatial components of the interference light pattern 48 (i.e., speckle grains in the case where the interference light pattern includes a speckle light pattern) (step 120), and values (e.g., power values) representative of the spatial components of the interference light pattern 48 are stored in bins 70 (initially, the first bins 70a of the corresponding detectors 68) (step 122).

At this point, only one quadrature measurement has been taken. If the interferometer 22 has not been set to all four of the phases (step 124), the controller 24 then repeats steps 102-122 to take the next quadrature measurement. That is, the next pulse of ultrasound 32 (e.g., ultrasound pulse $U_b$ illustrated in FIG. 5) is generated and emitted into the anatomical structure 16 (step 102); the phase difference between the sample light 40 and the reference light 42 is set to the next pre-defined value (e.g., $\pi/2$) (step 104); the next pulse of source light 38 is generated (step 106) and split into the next pulse of sample light 40 (e.g., sample light pulse $L_b$ illustrated in FIG. 5) and a pulse of reference light 42 (step 108); the next pulse of sample light 40 is frequency shifted by the ultrasound frequency $f_{us}$ (step 110); the frequency shifted pulse of sample light 40 is delivered and diffusively scattered within the anatomical structure 16 (step 112); a portion of the scattered pulse of sample light 40 passing through the target voxel 14 is frequency shifted (tagged) by the pulse of ultrasound 32 passing through the target voxel 14, thereby generating the next pulse of scattered signal light 44 (step 114); the remaining portion of the scattered pulse of sample light 40 not passing through the target voxel 14 is not frequency shifted (not tagged) by the pulse of ultrasound 32 passing through the target voxel 14, thereby generating the next pulse of scattered background light 46 (step 116); the next pulses of reference light 42 and sample light pattern 47 are combined into the pulse of the next interference light pattern 48 (e.g., the interference light pattern pulse $I_b$ illustrated in FIG. 5) (step 118); the spatial components of the next pulse of the interference light pattern 48 are detected (step 120); and the resulting spatial component values are stored in the bins 70 (e.g., the second bins 70b of the corresponding detectors 68) (step 122).

Thus, it can be appreciated that steps 102-122 will be repeated to take the remaining quadrature measurements to generate and detect the pulses of the remaining interference light patterns (e.g., the third and fourth interference light pattern pulses $I_c$, $I_d$ illustrated in FIG. 5) for the remaining phase settings (e.g., $\pi$ and $3\pi/2$) and ultimate storage of the spatial component values in the bins 70 (e.g., the third and fourth bins 70c, 70d of the corresponding detectors 68).

After all four quadrature measurements have been taken, the controller 24 recalls the spatial component values of the detected interference light pattern pulses 48 from the bins 70 of the lock-in camera 28 and transfers these values to the processor 30 (step 126). The processor 30 reconstructs the amplitude of the signal light 44 from the four interference light patterns 48 based on these spatial component values (e.g., by using the quadrature equation [2]) (step 128). Steps 102-128 can be iterated to repeatedly acquire data measurements of the target voxel 14, and if a sufficient number of data measurements have been acquired (step 130), the processor 30 may then determine the physiologically-dependent optical parameter (e.g., level of deoxygenated and/or oxygenated hemoglobin concentration or relative abundance or level of water concentration or relative water concentration) of the target voxel 14 based on the data measurements (step 132). In the case where the target voxel 14 is brain matter, the processor 30 may further determine the level of neural activity within the target voxel 14 based on the determined physiologically-dependent optical parameter (step 134).

For example, if the physiologically-dependent optical parameter is the level of deoxygenated and/or oxygenated hemoglobin concentration or relative abundance, and if the amplitude of the signal light 44 is relatively low (or high), indicating high absorption of light by blood in the target voxel 14, it can be assumed that there is a relatively high (or low) hemodynamic response (depending on the light wavelength used) through the target voxel 14, and thus, a substantial amount of neural activity in the target voxel 14. In contrast, if the amplitude of the signal light 44 is relatively high (or low), indicating low absorption of light by blood in the target voxel 14, it can be assumed that there is a relatively low hemodynamic response (depending on the wavelength) through the target voxel 14, and thus, comparatively little neural activity in the target voxel 14.

If the physiologically-dependent optical parameter is the level of water concentration or relative water concentration, and if the amplitude of the signal light 44 greatly varies over a short period of time, indicating a fast signal of neural activity in the brain tissue, it can be assumed that there is a substantial amount of neural activity in the target voxel 14. In contrast, if the amplitude of the signal light 44 varies very little over a short period of time, indicating that there is no fast signal of neural activity in the brain matter, it can be assumed that there is very little or no neural activity in the target voxel 14.

Figure 14:
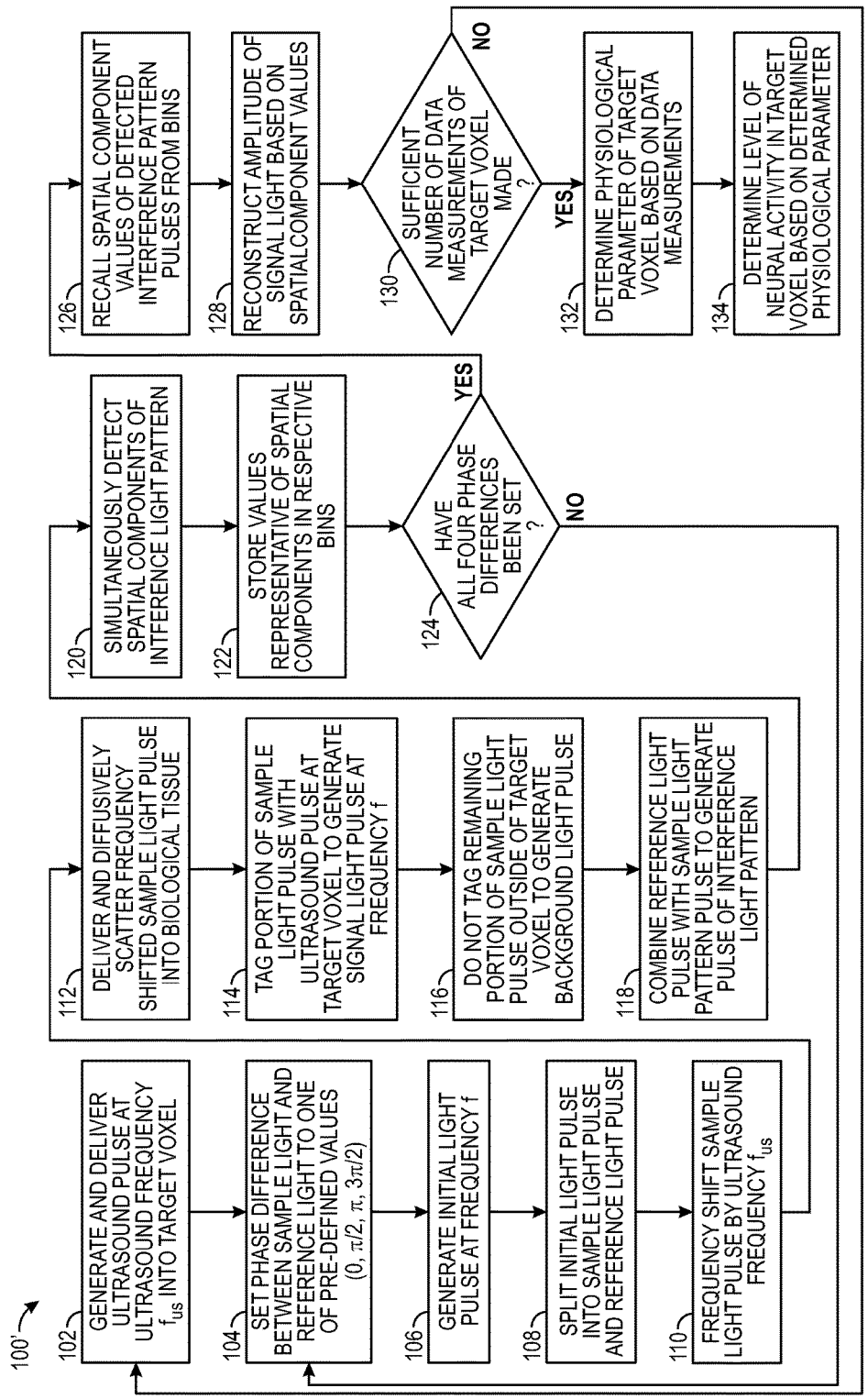
FIG. 14 is a flow diagram of another method used by the UOT system of FIG. 1 to non-invasively measure a physiologically-dependent optical parameter using the pulse sequence of FIG. 7.

Referring to FIG. 14, another particular method 100' performed by the UOT system 10 to non-invasively image the target voxel 14 in the anatomical structure 16 will now be described. This particular method 100' implements the pulsing sequence of FIG. 7.

The method 100' is similar to the method 100 illustrated in FIG. 13, with the exception that, instead of a one-to-one correspondence between the sample light pulse and the ultrasound pulse, multiple sample pulses (in this case, four) are delivered to the biological tissue for every ultrasound pulse delivered to the biological tissue. Thus, after a quadrature measurement, the process returns to step 104 (instead of step 102) to take the next quadrature measurement.

That is, during the delivery of current pulse of ultrasound 32 (e.g., ultrasound pulse U illustrated in FIG. 5), the phase difference between the sample light 40 and the reference light 42 is set to the next pre-defined value (e.g., π/2) (step 104); the next pulse of source light 38 is generated (step 106) and split into the next pulse of sample light 40 (e.g., sample light pulse $L_b$ illustrated in FIG. 5) and a pulse of reference light 42 (step 108); the next pulse of sample light 40 is frequency shifted by the ultrasound frequency $f_{us}$ (step 110); the frequency shifted pulse of sample light 40 is delivered and diffusively scattered within the anatomical structure 16 (step 112); a portion of the scattered pulse of sample light 40 passing through the target voxel 14 is frequency shifted (tagged) by the pulse of ultrasound 32 passing through the target voxel 14, thereby generating the next pulse of scattered signal light 44 (step 114); the remaining portion of the scattered pulse of sample light 40 not passing through the target voxel 14 is not frequency shifted (not tagged) by the pulse of ultrasound 32 passing through the target voxel 14, thereby generating the next pulse of scattered background light 46 that combines with the pulse of signal light 44 to create a pulse of the sample light pattern 47 (step 116); the next pulses of reference light 42 and sample light pattern 47 are combined into the pulse of the next interference light pattern 48 (e.g., the interference light pattern pulse $I_b$ illustrated in FIG. 5) (step 118); the spatial components of the next pulse of the interference light pattern 48 are detected (step 120); and the resulting spatial component values are stored in the bins 70 (e.g., the second bins 70 of the corresponding detectors 68) (step 122).

After all four quadrature measurements have been taken at steps 102-124, as in the manner described above with respect to the method 100 of FIG. 13, the spatial component values of the detected interference light pattern pulses 48 are recalled from the bins 70 of the lock-in camera 28 (step 126); and the amplitude of the signal light 44 is reconstructed from the four interference light patterns 48 based on these spatial component values (step 128). Steps 102-128 can be iterated to repeatedly acquire data measurements of the target voxel 14, and if a sufficient number of data measurements have been acquired (step 130), the physiologically-dependent optical parameter (e.g., the level of deoxygenated and/or oxygenated hemoglobin concentration or relative abundance or level of water concentration or relative water concentration) of the target voxel 14 is determined based on the data measurements (step 132), and the level of neural activity within the target voxel 14 is determined based on the determined physiologically-dependent optical parameter (step 134).

Figure 15:
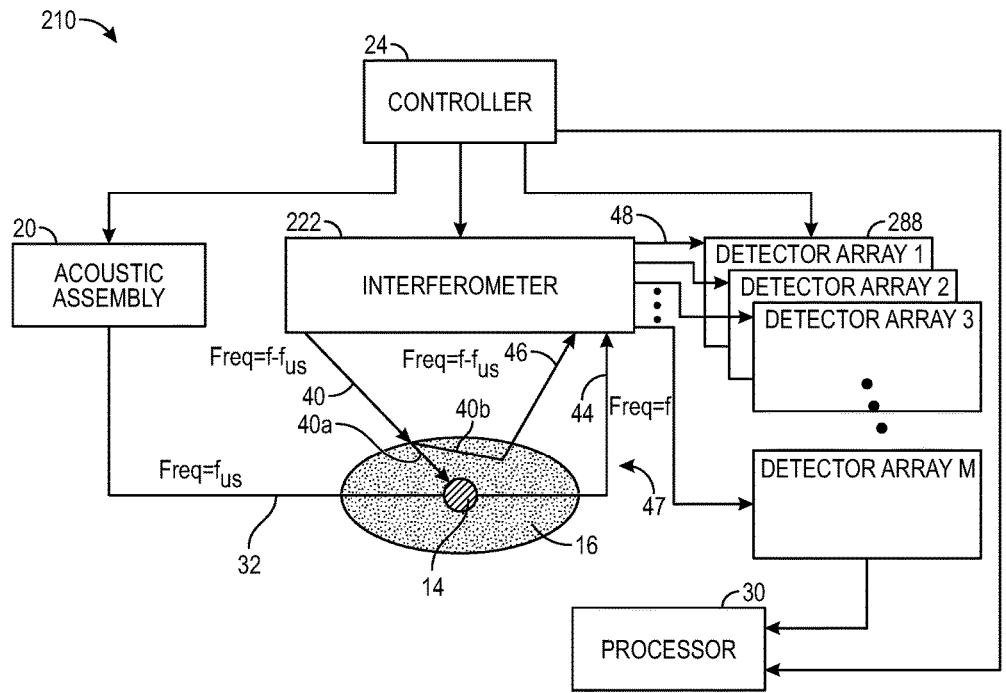
FIG. 15 is a block diagram of an ultrasound modulating optical tomography (UOT) system constructed in accordance with another embodiment of the present inventions.

Referring now to FIG. 15, a UOT system 210 constructed in accordance with another embodiment of the present inventions will be described. The UOT system 210 is similar to the UOT system 10 illustrated in FIG. 1 in that it is designed to non-invasively measure a physiologically-dependent optical parameter (which may be the same types of parameters discussed above with respect to the UOT system 10) of a target voxel 14 in an anatomical structure 16. As with the UOT system 10, in a practical implementation, the UOT system 210 will acquire data from multiple target voxels 14 spatially separated from each other within a volume of interest (not shown). For purposes of brevity, the UOT system 210 will be described as acquiring one data voxel (i.e., data representative of a physiologically-dependent optical parameter of the target voxel 14), although it should be understood that the UOT system 210 may be capable of acquiring more than one data voxel from the volume of interest of the anatomical structure 16. The UOT system 210 differs from the UOT system 10 in that, instead of sequentially performing an M number of measurements of the target voxel 14, the UOT system 210 concurrently performs an M number of measurements of the target voxel 14.

To this end, the UOT system 210 comprises an interferometer 222 that, unlike the interferometer 22 of the UOT system 10 (which sequentially generates an M number of interference patterns 48 via phase modulation), concurrently generates an M number of interference patterns 48 via phase modulation. The UOT system 210 further comprises an M number of optical detector (or pixel) arrays 228 (e.g., using multiple cameras or dedicated spatial regions of a single camera) that, unlike the lock-in camera 28 of the UOT system 10 (which detects the interference light patterns 48 using a single array of detectors in the form of a lock-in camera 28 (in each of several successive bins associated with each detector (or pixel)), are optically registered with each other to concurrently detect the interference light patterns 48 over the M number of phases.

Figure 16:
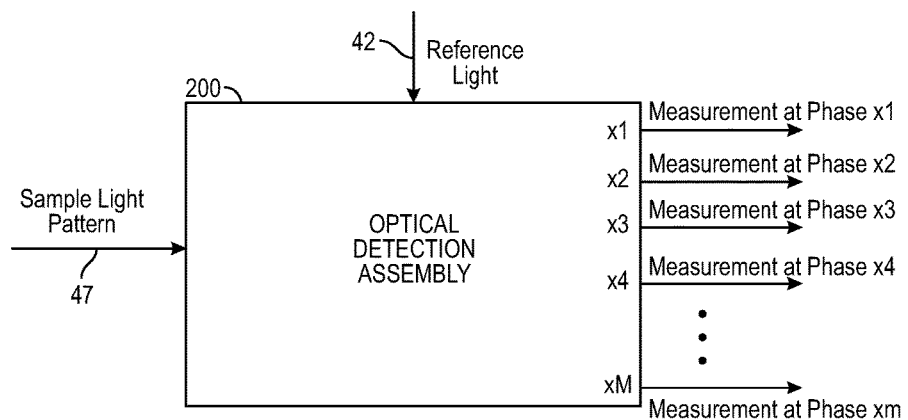
FIG. 16 is a block diagram of a generic optical detection assembly that can be incorporated into the UOT system of FIG. 15.

Referring to FIG. 16, the optical detection portion of the interferometer 222 that concurrently generates the M number of interference patterns 48, as well as the M number of optical detector arrays 228, may be topologically combined into an optical detection assembly 200, various specific embodiments of which will be described in further detail below. Such optical detection assembly 200 (including the specific embodiments thereof described below) is configured for receiving the sample light pattern 47 and reference light 44, and outputting an M number of phase shifted measurements. In some embodiments described, the optical detection assembly 200 may optionally comprise on-board processing that computes and outputs one or more values (representative of the desired physiologically-dependent optical parameter) from the M number of measurements.

Although the specific embodiments of the optical detection assembly 200 described below utilize a two-measurement detection scheme (M=2) or a four-measurement detection scheme (M=4), the optical detection assembly 200 illustrated in FIG. 16 can be generalized to provide any combinations of phase differences between the outputted measurements by simply introducing the appropriate phase lags to the measurements. Thus, the optical detection assembly 200 can be viewed as a "black box" that receives the sample light pattern 47 and reference light 40 as inputs, and outputting an M number of measurements over different phases. While lock-in cameras may be scaled to have more bins (e.g., twice as many), doing so implies changes to the electronic/very large scale integration (VLSI) design of lock-in camera pixels, which may detrimentally impact fill factor, speed of operation, bin saturation level, number of pixels, custom silicon chip design and fabrication, and so forth, specific embodiments of the generalized optical detection assembly 200 can be designed with arbitrarily large numbers of output ports (M is arbitrary) and high pixel counts, simply by introducing, e.g., more beam splitters, reference shifts, and camera alignments, as will be shown in further detail below.

Figure 17:
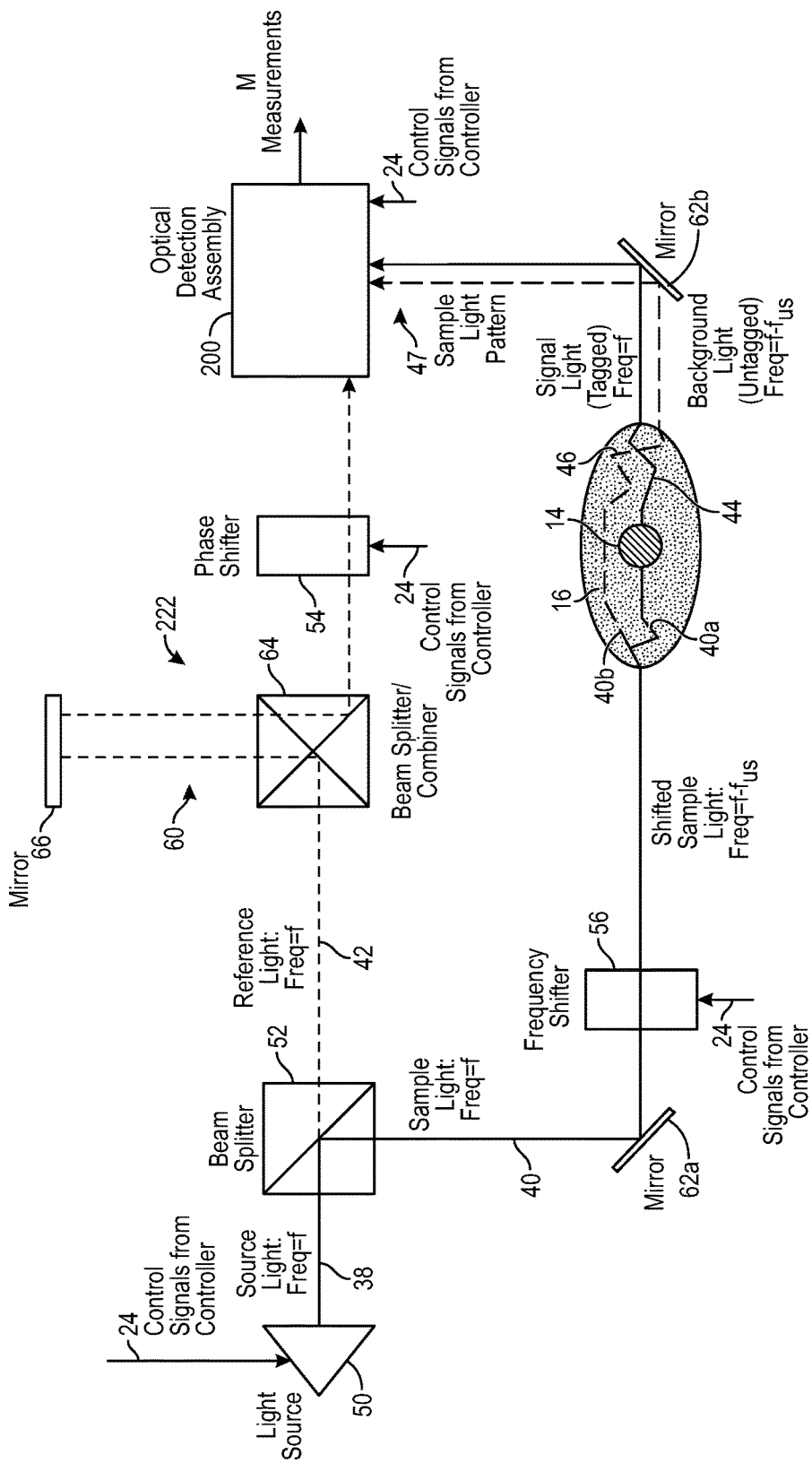
FIG. 17 is a block diagram of one embodiment of an interferometer used in the UOT system of FIG. 15.

Referring to FIG. 17, it can be seen that the interferometer 222 of the UOT system 210 is identical to the interferometer 22 of the UOT system 10 illustrated in FIG. 3a, with the exception that the detection portion of the interferometer, along with cameras, are subsumed into an optical detection assembly 200. Of course, the interferometer 222 of the UOT system 210 can alternatively be identical to the interferometers 22 of the UOT system illustrated in FIGS. 3b-3d. In essence, the light combiner 58, as well as the lock-in camera 28, are replaced with the optical detection assembly 200 illustrated in FIG. 16. Although optical detection assemblies 200 are described herein in the context of a UOT system 210 that combines the signal light 44 and reference light 42 in a homodyne manner, it should be appreciated that optical detection assemblies 200 described herein may be alternatively used in the context of other systems that combine the signal light 44 and reference light 42 in a heterodyne manner.

Although the UOT system 210 is described herein as non-invasively imaging one target voxel 14 at a time, the UOT system 10 may be modified to image multiple target voxels 14 at a time. For example, in one particular embodiment, an acoustic assembly may simultaneously generate multiple foci in parallel (i.e., focuses the ultrasound on multiple target voxels at the same time), with each ultrasound focus being modulated at a different optical frequency (e.g., $f_1-f_{us}$, $f_2-f_{us}$, $f_3-f_{us}$, etc.), with separate frequency-shifted reference light (e.g., $f_1$, $f_2$, $f_3$, etc.) being used to interfere with the resulting signal light in a homodyne manner. This enables parallelization of the UOT detection. Separate optical detection assemblies 200, each having an M number of detector arrays, may be utilized to detect the different interference patterns corresponding to the different target voxels.

By using the optical detection assembly 200 in applications such as in UOT, lock-in detection can be made essentially instantaneous, limited only by the achievable pulse durations of the sample light (e.g., in the context of UOT, a 1 microsecond optical pulse width when used in conjunction with a 1 MHz ultrasound frequency, or a 0.5 microsecond optical pulse width used when used in conjunction with a 2 MHz ultrasound frequency), which would correspond, for instance via the operative speckle decorrelation times, to imaging depths into tissue of many centimeters.

Thus, the following embodiments of optical detection assemblies 200 can overcome the problem of short speckle de-correlation times for imaging at great depths inside dynamic, strongly scattering biological tissues, enabling UOT and other related methods to address the problem of in vivo deep-tissue imaging, e.g., through many millimeters of human skull followed by many millimeters of brain tissue. Not only can these optical detection assemblies 200 be used to detect blood-oxygen-level dependent signals, flow response, or other physiological dependent optical parameters indicative of localized changes in neural activity in the human brain, it is contemplated that these optical detection assemblies 200 can be used to detect changes faster than hemodynamic responses through the human skull. These optical detection assemblies 200 can also be used with non-endogenous contrast agents, such as protein-based calcium or voltage indicators that optically report neuronal activity (see Broussard G J, Liang R, Tian L, "Monitoring Activity in Neural Circuits with Genetically Encoded Indicators," Frontiers in Molecular Neuroscience, Vol. 7 (2014).

Furthermore, the following embodiments of detection assemblies 200 can be used with conventional cameras with high pixel counts, effectively turning any conventional camera into a lock-in camera, and thus, dramatically expanding the achievable scale of lock-in detection of optical wavefronts. For application to UOT, this means that many more optical speckle grains can be sampled, thereby increasing signal-to-noise ratio. For example, conventional cameras with 10 or 100 or more megapixels can be utilized for lock-in detection in the following embodiments of the UOT system, potentially increasing the scale of lock-in detection of optical wavefronts by a factor of approximately 1000 over the current state of art (e.g., as represented by the Heliotis HeliCam C3 lock-in camera with less than 100,000 pixels).

Thus, the following embodiments of optical detection assemblies 200 are sufficiently sensitive to be useful for through-human-skull functional neuroimaging by enabling high-pixel count based lock-in detection and demodulation of the scattered optical wavefront emanating from a subject's head, and doing so even in the presence of the fast speckle decorrelations characteristic of deep tissue imaging. For example, a UOT system 210 that uses a 1-megapixel conventional camera with a 7 KHz frame rate, 1 ultrasound pulse per frame, and a 1 microsecond optical pulse duration, may have an imaging depth of approximately 10 centimeters in living brain tissue—enough for whole brain coverage in a human. This suggests that the UOT system 210 could access the entire human brain, given sufficient detector sensitivity, for which the achievable signal-to-noise ratio scales with the square root of the number of camera pixels used and with the square root of the number of temporal averages taken per voxel.

Although the optical detection assemblies 200 are described and illustrated herein in the context of the UOT system 210, the optical detection assemblies 200 described herein can be used in any optical detection system (including pulsed or continuous UOT) where it is desirable to takes multiple measurements of a target voxel 14 simultaneously or in quick succession. For example, in the context of quasi-ballistic/snake photon Optical Coherent Tomography ("snake photon OCT"), which path-length encodes the signal light scattered by the target voxel 14, in contrast to UOT, which frequency encodes the signal light scattered by the target voxel 14, the optical detection assemblies 200 described herein can be used to simultaneously detect interference light patterns output by the interferometers of snake photon OCT systems.

For example, instead of frequency encoding the signal light 44 with ultrasound 32, snake photon OCT systems may average the detected intensity values of interference patterns on a pixel-by-pixel basis to compute an estimate of the magnitude of the signal light within a user-defined path-length range that approximates straight travel paths in tissue (i.e., quasi-ballistic photons that have experienced some degree of scattering but have a path length that is within a light source coherence length from the path length of the reference optical path), as well as the detection of photons that have a straight travel path in tissue (i.e., ballistic photons that have a path length that matches the path length of the reference optical path). Further detail discussing snake photon OCT systems are set forth in U.S. Provisional Patent Application Ser. No. 62/599,510, entitled "Systems and Methods for Quasi-Ballistic Photon Optical Coherence Tomography in Diffusive Scattering Media Using a Lock-In Camera Detector", filed Dec. 15, 2017, which is expressly incorporated herein by reference; and U.S. patent application Ser. No. 15/853,538, entitled "Systems And Methods for Quasi-Ballistic Photon Optical Coherence Tomography in Diffusive Scattering Media Using a Lock-In Camera Detector", filed Dec. 22, 2017, which is also expressly incorporated herein by reference.

Figure 18:
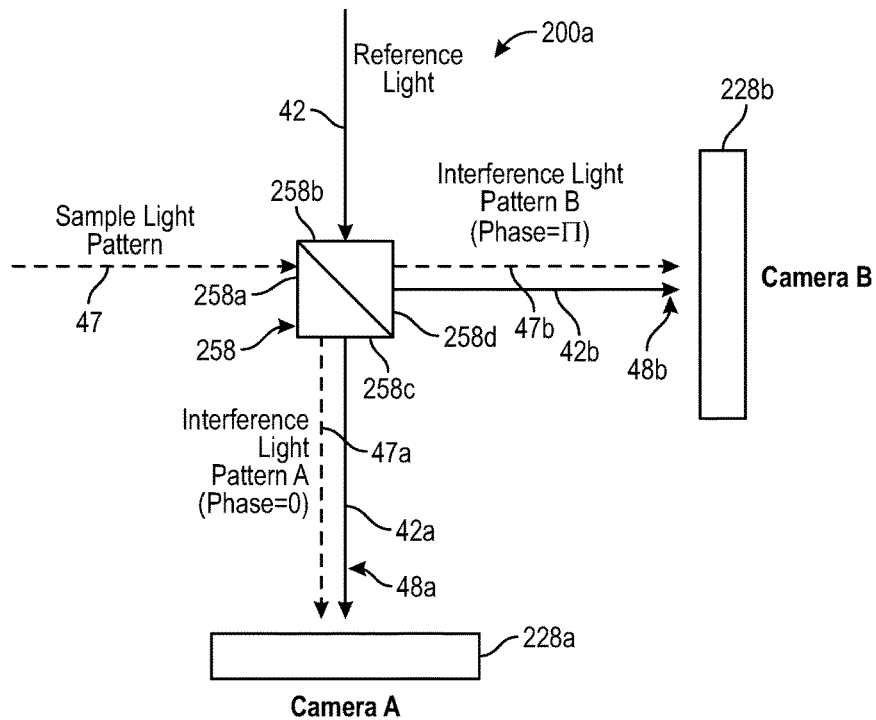
FIG. 18 is a block diagram of one specific embodiment of the optical detection assembly of FIG. 16.

Referring to FIG. 18, one specific embodiment of an optical detection assembly 200a is capable of making two separate measurements of the target voxel 14 (shown in FIG. 17) simultaneously or in short succession by measuring the interference between the sample light field 47 and reference light 42 at two separate phases differing from each other by an angular phase of $\pi$.

To this end, the optical detection assembly 200a comprises a single beam splitter/combiner 258 (which replaces the light combiner 58 of the interferometer 22 illustrated in FIGS. 3a-3d). The beam splitter/combiner 258 is configured for splitting the reference light 42 respectively into reference light 42 having an M number of different phases relative to the sample light pattern 47 (and in this case, reference light 42a, 42b respectively having two different phases of 0 and π), splitting the sample light pattern 47 respectively into sample light pattern portions 47a, 47b, and concurrently combining the sample light pattern portions 47a, 47b and the reference light 42a, 42b to respectively generate an M number of interference light patterns 48 (in this case, two interference light patterns 48a ("Interference Light Pattern A"), 48b ("Interference Light Pattern B")).

That is, the sample light pattern 47 enters an input port 258a of the beam splitter/combiner 258, where it is split into a reflected sample pattern portion 47a and a transmitted sample light pattern portion 47b, and the reference light 42 enters another input port 258b of the beam splitter/combiner 258, where it is split into a transmitted reference light 42a and a reflected reference light 42b. In a simultaneous manner, the reflected sample light pattern portion 47a interferes with the transmitted reference light 42a to generate the interference light pattern 48a, and the transmitted sample light pattern portion 47b interferes with the reflected reference light 42b to generate the interference light pattern 48b.

Due to power conservation, a four-port network, such as the beam splitter/combiner 258, requires the total power entering the input ports 258a, 258b to be equal to the total power exiting the output ports 258c, 258d, and thus, the transmitted reference light 42a will have a nominal phase of 0, and the reflected reference light 42b will have a phase of π. That is, as will be described in further detail below, since the combined power of the DC terms of the interference light patterns 48a, 48b exiting the respective output ports 258a, 258b of the beam splitter/combiner 258 will be equal to the combined power of combined DC power of the sample light pattern 47 and reference light 42 respectively entering the input ports 258a, 258b of the beam splitter/combiner 258, the interfering AC beat pattern terms of the respective interference light patterns 48a, 48b will need to differ in phase by 180 degrees such that they sum to zero.

Although a lock-in camera with two "bins" can be used to detect the two interference light patterns 48a, 48b, in such a scenario, the interference light patterns 48a, 48b would have to be detected sequentially, with the resulting values stored in the two bins in rapid succession, preferably with the total time to acquire the two measurements being shorter than the speckle de-correlation time of the target voxel 14, which will fall into the microsecond range or below if the target voxel 14 is multiple centimeters deep within the anatomical structure 16 (shown in FIG. 17).

However, instead of using a conventional lock-in camera, the optical detection assembly 200a comprises an M number of arrays of detectors (or pixels) 228 (in this case, two arrays of detectors in the form of cameras 228a ("Camera A"), 228b ("Camera B") respectively disposed at two output ports 258c, 258d of the beam splitter/combiner 258 for concurrently detecting the respective two interference light patterns 48a, 48b, and generating M pluralities of values representative of intensities of the spatial components ("speckle grains") of the respective M number of interference light patterns (in this case, two pluralities of values representative of spatial components of the interference light patterns 48a, 48b). Thus, the sample light field 47 and reference light 42 combine to project an interference light pattern 48a onto the camera 228a, and likewise to project an interference light pattern 48b onto the camera 228b, but with respect to a different phase of the reference light 42. In the illustrated embodiment, the planes of the cameras 228a, 228b are perpendicular to each other, such that they face the respective output ports 258c, 258d of the beam splitter/combiner 258. The cameras 228a, 228b may be conventional in nature (e.g., readily available conventional charge-coupled device (CCD) cameras).

Figure 19:
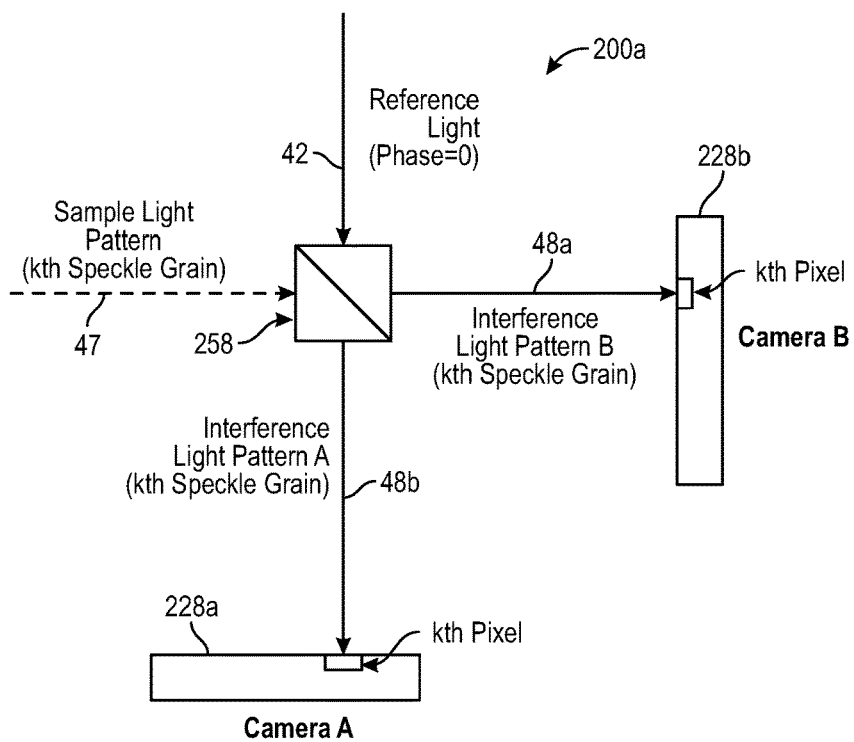
FIG. 19 is a block diagram of the optical detection assembly of FIG. 18, particularly showing the generation and detection of a kth speckle grain of an interference pattern.

Although the cameras 228a, 228b are separate and distinct, the cameras 228a, 228b are optically aligned with each other, such that any given pixels on the cameras 228a, 228b have a known one-to-one correspondence with each other. That is, as illustrated in FIG. 19, a spatial component of the sample light pattern 47 (i.e., the kth speckle grain of the speckle light field) interferes with the reference light 42a with no phase shift (i.e., 0) (shown in FIG. 18) to generate a kth speckle grain of the interference light pattern 48a that is detected by kth pixel of the camera 228a, and the same kth speckle grain of the sample light pattern 47 interferes with the reference light 42b with a phase shift (i.e., π) (shown in FIG. 18) to generate a corresponding kth speckle grain of the interference light pattern 48b that is detected by the corresponding kth pixel of the camera 228b. Since the kth pixel of the camera 228a has a known correspondence via optical alignment with the kth pixel of the camera 228b, the pair of intensity values detected by the kth pixels of the cameras 228a, 228b serve as the analog to the pair of intensity values that would normally be stored by the kth pixel in the two bins of a lock-in camera. It should be appreciated that although FIG. 19 illustrates one speckle grain "k," an equivalent process for measuring the speckle grain k takes place for all speckles grains in parallel in the manner of imaging an entire speckle light field.

At each corresponding pair of kth pixels, the optical power received by the respective cameras 228a, 228b is equal to the summation of the power of the reference light 42 ($P_{reference}A$ and $P_{reference}B$) input into the beam splitter/combiner 258, the sample light pattern 47 ($P_{sample}A$ and $P_{sample}B$) input into the beam splitter/combiner 258, and an interference term between the reference light 42 and sample light pattern 47 ($P_{interfere}A$ and $P_{interfere}B$). By the power conservation, the interference terms $P_{interfere}A$ and $P_{interfere}B$ are 180 degrees out of phase for cameras 228a, 228b.

It follows that, in the context of pulsed UOT, the power detected at a kth pixel for the first camera 228a can be expressed as:

$$\text{Value}_{1,k} = P_{background} + P_{signal} + P_{reference} + 2(P_{signal} \times P_{reference})^{1/2} \times \cos(\varphi_{unknown1,\ speckle\ k}) + 2(P_{signal} \times P_{background})^{1/2} \times \cos(2\pi \times f_{us} - \varphi_{unknown2,\ speckle\ k} + \pi) + 2(P_{reference} \times P_{background})^{1/2} \times \cos(2\pi \times f_{us} - \varphi_{unknown3,\ speckle\ k}),  \quad [15]$$

and likewise, the power detected at the corresponding kth pixel of the second camera 228b can be expressed as:

$$\text{Value}_{2,k} = P_{background} + P_{signal} + P_{reference} + 2(P_{signal} \times P_{reference})^{1/2} \times \cos(\varphi_{unknown1,\ speckle\ k} + \pi) + 2(P_{signal} \times P_{background})^{1/2} \times \cos(2\pi \times f_{us} - \varphi_{unknown2,\ speckle\ k} + \pi) + 2(P_{reference} \times P_{background})^{1/2} \times \cos(2\pi \times f_{us} - \varphi_{unknown3,\ speckle\ k} + \pi); \quad [16]$$

where $P_{background}$ represents light at frequency $f+f_{us}$ that has not been tagged with the ultrasound 32; $P_{signal}$ represents light at frequency f that has been tagged with the ultrasound 32; $P_{reference}$ represents the reference light at frequency f; and $\varphi_{unknown1,\ speckle\ k}$, $\varphi_{unknown2,\ speckle\ k}$, and $\varphi_{unknown3,\ speckle\ k}$ are random phases at the kth speckle grain at the time of measurement, which originates via multiple scattering of coherent light inside the tissue.

The terms $2(P_{signal} \times P_{background})^{1/2} \times \cos(2\pi \times f_{us} - \varphi_{unknown2}) + 2(P_{reference} \times P_{background})^{1/2} \times \cos(2\pi \times f_{us} - \varphi_{unknown3})$ oscillate at the frequency $f_{us}$, and are not detected by the cameras 228a, 228b given appropriate light pulse duration and integration time, and thus, can be ignored. As such, equations [15] and [16] can be respectively reduced to:

$$\text{Value}_{1,k} = P_{background} + P_{signal} + P_{reference} + 2(P_{signal} \times P_{reference})^{1/2} \times \cos(\varphi_{unknown}); \text{ and} \quad [17]$$

$$\text{Value}_{2,k} = P_{background} + P_{signal} + P_{reference} + 2(P_{signal} \times P_{reference})^{1/2} \times \cos(\varphi_{unknown} + \pi). \quad [18]$$

It is noted that the term $P_{background} + P_{signal} + P_{reference}$ in each of equations [17] and [18] represents the DC terms of the interference light patterns 48a, 48b, whereas the terms $2(P_{signal} \times P_{reference})^{1/2} \times \cos(\varphi_{unknown})$ and $2(P_{signal} \times P_{reference})^{1/2} \times \cos(\varphi_{unknown} + \pi)$ in the respective equations [17] and [18] represent the AC beat patterns of the interference light patterns 48a, 48b.

The terms $P_{background} + P_{signal} + P_{reference}$ are constant across the two cameras 228a, 228b, and thus, can be eliminated by taking the difference of the intensity values $\text{Value}_{1,k}$ and $\text{Value}_{2,k}$, leaving only the difference of the interference terms, as $2(P_{signal} \times P_{reference})^{1/2} \times \cos(\varphi_{unknown}) - 2(P_{signal} \times P_{reference})^{1/2} \times \cos(\varphi_{unknown} + \pi)$, which can be summed over all of the k pixels and then averaged in accordance with the following equation:

$$2(P_{signal} \times P_{reference})^{1/2} = (\Sigma k |\text{Value}_{1,k} - \text{Value}_{2,k}|)/N \text{ across all } k = 1, 2, \ldots N \text{ speckles or pixels}, \quad [19]$$

i.e., the average across all pixels of the absolute value of the difference across corresponding pixels. Based on known scaling relationship between the power of the reference light $P_{reference}$ and the power of the signal light $P_{signal}$ discussed above, the power of the $P_{signal}$ can be expressed as:

$$P_{signal} \propto (\Sigma k |\text{Value}_{1,k} - \text{Value}_{2,k}|)/N, \quad [20]$$

i.e., the average across all pixels of the absolute value of the difference across corresponding pixels.

It should be noted that other sign-rectifying operations of the intensity value differences besides taking the absolute can be utilized to obtain the power of the signal light 44. For example, a squaring operation can be applied to the intensity value differences. Thus, the power of the signal light 44 can alternatively be computed as the square of the difference between the two intensity values stored in the two bins 70 for each pixel 68 and then averaged in accordance with the following equation:

$$P_{signal} \propto ((\text{Value}_{1,k} - \text{Value}_{2,k})^2)/N \text{ across all } k = 1, 2, \ldots N \text{ speckles or pixels}. \quad [21]$$

Thus, it can be appreciated that the intention of the two-bin measurement is to arrive at a precise estimate of power of the signal light $P_{signal}$ up to the aforementioned scaling relationship defined by the strength of the reference light $P_{reference}$, by removing the terms that are constant between the two measurements of the cameras 228a, 228b, removing the unknown speckle-specific phases, and extracting only the amplitude of the cosine term. As with the two-bin detection scheme described above with respect to the UOT system 10, with an N number of pixels, the signal-to-noise ratio (SNR) scales with $N^{1/2}$ in accordance with equation [13] set forth above.

In the context of the UOT, just as with the detection schemes described above, this detection scheme serves as a measurement of a physiologically-dependent optical parameter at the target voxel 14.

It should be noted that if the split ratio of the beam splitter/combiner 258 is not 50/50, the interference terms would still be 180 degrees out of phase, i.e., $P_{interfere}A = -P_{interfere}B$ by the power conservation. In the case where the power of the reference light 42 is ramped up to achieve shot noise limited detection, then $P_{reference}A$ and $P_{reference}B$ are the dominant constant terms, which would no longer be equal across the cameras 128a, 128b, i.e., $P_{reference}A$ will not be equal to $P_{reference}B$. The subtraction process represented by equations [20] or [21] can then be modified to use a scaled subtraction to zero out the constant offset during subtraction. This scaling ratio can be determined a priori. The resulting difference will still be a quantifiable measure of the interference term, and hence, in the context of UOT, of the UOT tagged photon signal strength.

Figure 20:
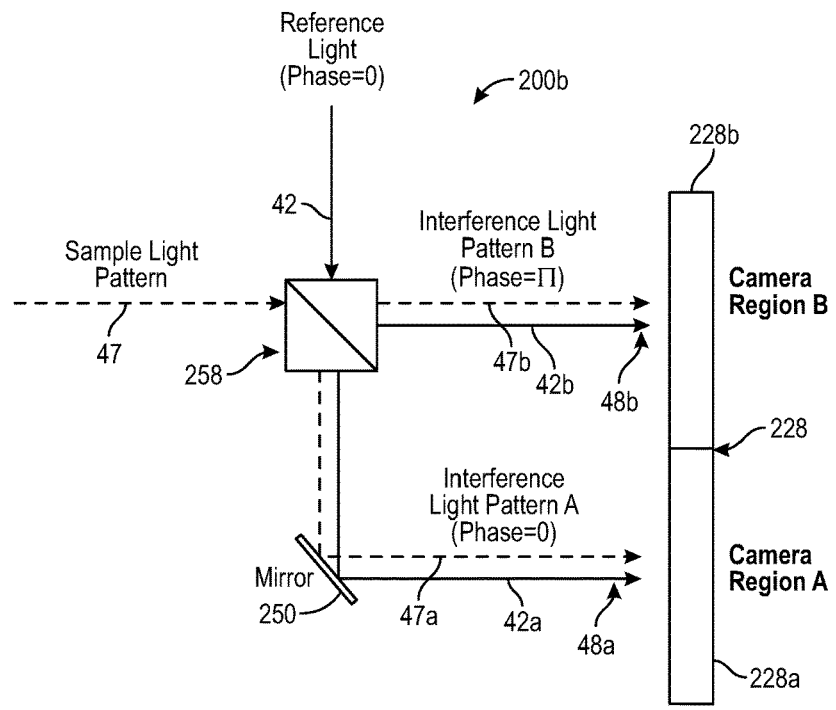
FIG. 20 is a block diagram of another specific embodiment of the optical detection assembly of FIG. 16.

Although the optical detection assembly 200a has been described and illustrated as comprising detector arrays that take the form of separate cameras 228a, 228b (in effect, the detector arrays are mechanically disposed on separate camera microchips), an optical detection assembly 200b can comprise detection arrays that take the form of a single camera 228 (in effect, the detector arrays are mechanically disposed on a single camera microchip), as illustrated in FIG. 20.

As with the optical detection assembly 200a, the beam splitter/combiner 258 of the optical detection assembly 200b is configured for splitting the reference light 42 respectively into reference light 42 having an M number of different phases relative to the sample light pattern 47 (and in this case, reference light 42a, 42b respectively having two different phases of 0 and $\pi$), splitting the sample light pattern 47 respectively into sample light pattern portions 47a, 47b, and concurrently combining the sample light pattern portions 47a, 47b and the reference light 42a, 42b to respectively generate an M number of interference light patterns 48 (in this case, two interference light patterns 48a ("Interference Light Pattern A"), 48b ("Interference Light Pattern B")).

However, instead of respectively projecting the interference light patterns 48a, 48b onto two cameras, the beam splitter/combiner 258 of the optical detection assembly 200b projects the interference light patterns 48a, 48b from its respective output ports onto two separate spatial regions 228a, 228b of the same camera 228. To this end, the optical detection assembly 200b comprises an angled mirror 250 configured for directing the interference light pattern 48a from the beam splitter/combiner 258 towards the same plane to which the interference light pattern 48b is directed, i.e., towards the single camera 248.

Figure 21:
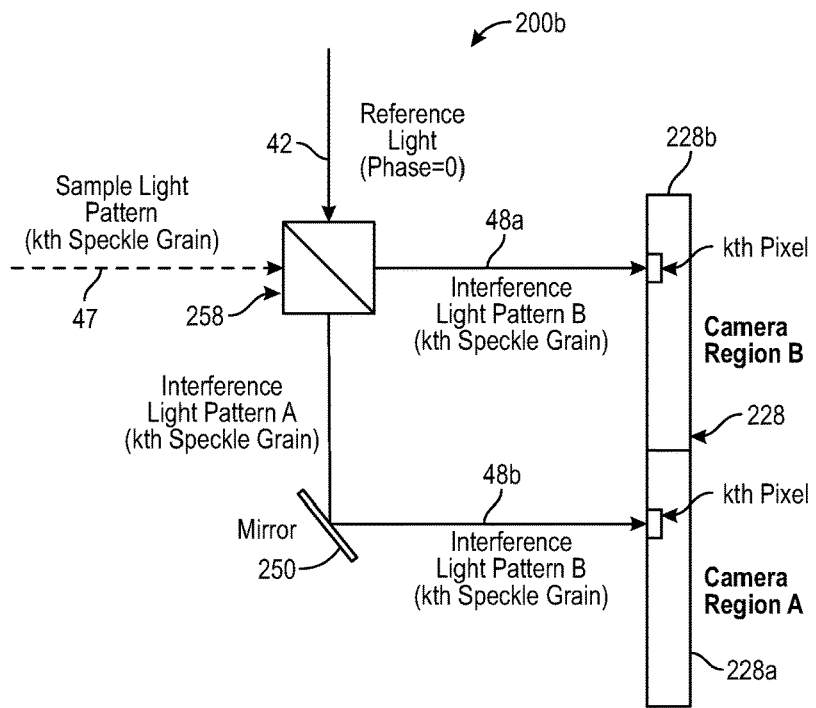
FIG. 21 is a block diagram of the optical detection assembly of FIG. 20, particularly showing the generation and detection of a kth speckle grain of an interference pattern.

In the same manner as the cameras 228a, 228b are optically aligned with each other in the optical detection assembly 200a, the spatial regions 228a, 228b of the single camera 228 of the optical detection assembly 200b are optically aligned with each other, such that any given pixels on the spatial regions 228a, 228b have a known one-to-one correspondence with each other. That is, as illustrated in FIG. 21, the kth speckle grain of the sample light pattern 47 interferes with the reference light 42a with no phase shift (i.e., 0 phase) to generate a kth speckle grain of the interference light pattern 48a that is detected by the kth pixel of the spatial region 228a of the camera 228, and the same kth speckle grain of the sample light pattern 47 interferes with the reference light 42b with a phase shift (i.e., $\pi$) to generate a corresponding kth speckle grain of the interference light pattern 48b that is detected by the kth pixel of the spatial region 228b of the camera 228.

An estimate of the power of the signal light $P_{signal}$ can be determined in accordance with equations [20] or [21], where Value$_{1,k}$ is the power detected at a kth pixel for the first region 228a of the camera 228, and Value$_{2,k}$ is the power detected at a kth pixel for the second region 228b of the camera 228.

Although the optical detection assembly 200a has been described and illustrated as being capable of making two separate measurements of the target voxel 14 (shown in FIG. 17) simultaneously or in short succession by measuring the interference between the sample light field 47 and reference light 42 at two separate phases of the reference light 42, an optical detection assembly 200 may be capable of making more than two separate measurements of the target voxel 14 (shown in FIG. 17) simultaneously or in short succession by measuring the interference between the sample light field 47 and reference light 42 at more than two separate phases of the reference light 42.

Figure 22:
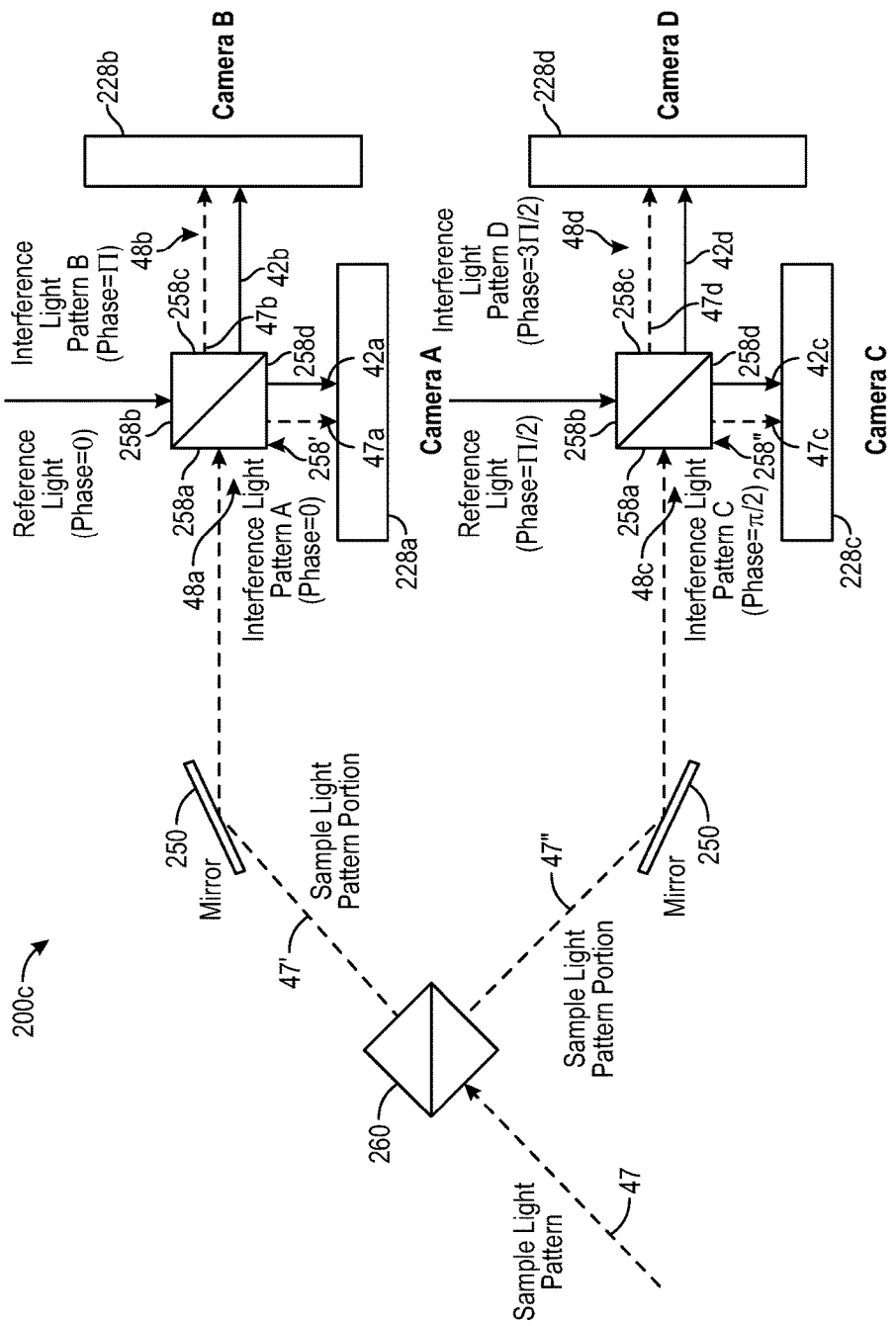
FIG. 22 is a block diagram of still another specific embodiment of the optical detection assembly of FIG. 16.

For example, one embodiment of an optical detection assembly 200c is capable of making four separate measurements of the target voxel 14 simultaneously or in short succession by measuring the interference between the sample light field 47 and reference light 42 at four separate phases (e.g., 0, π/2, π, and 3π/2) of the reference light 42, as illustrated in FIG. 22.

To this end, the optical detection assembly 200c comprises at least one beam splitter 260 configured for splitting the sample light pattern 47 into a plurality of sample light pattern portions, and in this case, a single beam splitter 260 that splits the sample light pattern 47 into first and second sample light pattern portions 47', 47".

The optical detection assembly 200c further comprises a first beam splitter/combiner 258' configured for splitting the reference light 42 (having a nominal phase of 0) respectively into a first two of the four different phases relative to the sample light pattern 47 (and in this case, reference light 42a, 42b respectively having two different phases of 0 and π), splitting the first sample light pattern portion 47' respectively into sample light pattern portions 42a, 42b, and concurrently combining the sample light pattern portions 47a, 47b and reference light 42a, 42b to respectively generate the first two of the four interference light patterns 48a ("Interference Light Pattern A"), 48b ("Interference Light Pattern B").

That is, the first sample light pattern portion 47' enters an input port 258a of the first beam splitter/combiner 258', where it is split into a reflected sample pattern portion 47a and a transmitted sample light pattern portion 47b, and the reference light 42 (having a phase of 0) enters another input port 258b of the first beam splitter/combiner 258', where it is split into a transmitted reference light 42a having a phase of 0 and a reflected reference light 42b having a shifted phase of π. In a simultaneous manner, the reflected sample light pattern portion 47a interferes with the transmitted reference light 42a to generate the interference light pattern 48a, and the transmitted sample light pattern portion 47b interferes with the reflected reference light 42b to generate the interference light pattern 48a.

The optical detection assembly 200c further comprises a second beam splitter/combiner 258" configured for splitting the reference light 42 (having a nominal phase of π/2) respectively into a second two of the four different phases relative to the sample light pattern 47 (and in this case, reference light 42c, 42d respectively having two different phases of π/2 and 3π/2), splitting the second sample light pattern portion 47" respectively into sample light pattern portions 42c, 42d, and concurrently combining the sample light pattern portions 47c, 47d and the reference light 42c, 42d to respectively generate the second two of the four interference light patterns 48c ("Interference Light Pattern C"), 48d ("Interference Light Pattern D").

That is, the second sample light pattern portion 47" enters an input port 258a of the second beam splitter/combiner 258", where it is split into a reflected sample pattern portion 47c and a transmitted sample light pattern portion 47d, and the reference light 42 (having a phase of π/2) enters another input port 258b of the second beam splitter/combiner 258", where it is split into a transmitted reference light 42c having a phase of π/2 and a reflected reference light 42d having a shifted phase of 3π/2. In a simultaneous manner, the reflected sample light pattern portion 47c interferes with the transmitted reference light 42c to generate the interference light pattern 48c, and the transmitted sample light pattern portion 47d interferes with the reflected reference light 42d to generate the interference light pattern 48d.

The optical detection assembly 200c further comprises a pair of angled mirrors 250 configured for respectively redirected the sample light pattern portion 47', 47" to the respective first and second beam splitter/combiners 258', 258".

Notably, as discussed above, the reference light 42 that enters the first beam splitter/combiner 258' has a nominal phase shift of 0, and the reference light 42 that enters the second beam splitter/combiner 258" has a nominal phase shift of π/2 (in order to get the full quadrature of phases), which can be accomplished by splitting the reference light 42 into two lines, and phase shifting one of the lines relative to the other line by π/2. The optical detection assembly 200c comprises a pair of angled mirrors 250a, 250b for respectively directing the first and second sample light patterns 47a, 47b towards the input ports 258a of the first and second beam splitter/combiners 258', 258".

Although a lock-in camera with four "bins" can be used to detect the four interference light patterns 48a-48d, in such a scenario, the interference light patterns 48a-48d would have to be detected sequentially, with the resulting values stored in the four bins in rapid succession, preferably with the total time to acquire the four measurements being shorter than the speckle de-correlation time of the target voxel 14, which, as briefly discussed above, will fall below a microsecond if the target voxel 14 is multiple centimeters deep within the anatomical structure 16 (shown in FIG. 16).

However, instead of using a conventional lock-in camera, the optical detection assembly 200c comprises four arrays of detectors (or pixels) 228 (in this case, four arrays of detectors in the form of cameras 228a ("Camera A"), 228b ("Camera B"), 228c ("Camera C"), and 228d ("Camera D"), respectively disposed at the output ports 258c, 258d of the first and second beam splitter/combiners 258', 258" for concurrently detecting the respective four interference light patterns 48a-48d, and generating four pluralities of values representative of intensities of the spatial components of the respective four interference light patterns 48a-48d. Thus, the sample light field 47 and reference light 42 combine to project an interference light pattern 48a onto the camera 228a, project an interference light pattern 48b onto the camera 228b, project an interference light pattern 48c onto the camera 228c, and project an interference light pattern 48d onto the camera 228d, all with respect to different phases of the reference light 42. In the illustrated embodiment, the planes of the cameras 228a, 228b are perpendicular to each other, such that they face the respective output ports 258c, 258d of the first beam splitter/combiner 258', and the planes of the cameras 228c, 228d are perpendicular to each other, such that they face the respective output ports 258c, 258d of the second beam splitter/combiner 258".

It should be appreciated that as the number of measurements increases (e.g., from two to four) using a lock-in camera, the total time to acquire the measurements increases in a commensurate manner, whereas as the number of measurements increases (e.g., from two to four) using the optical detection assemblies 200 described herein, the total time to acquire the measurements remains essentially the same.

Figure 23:
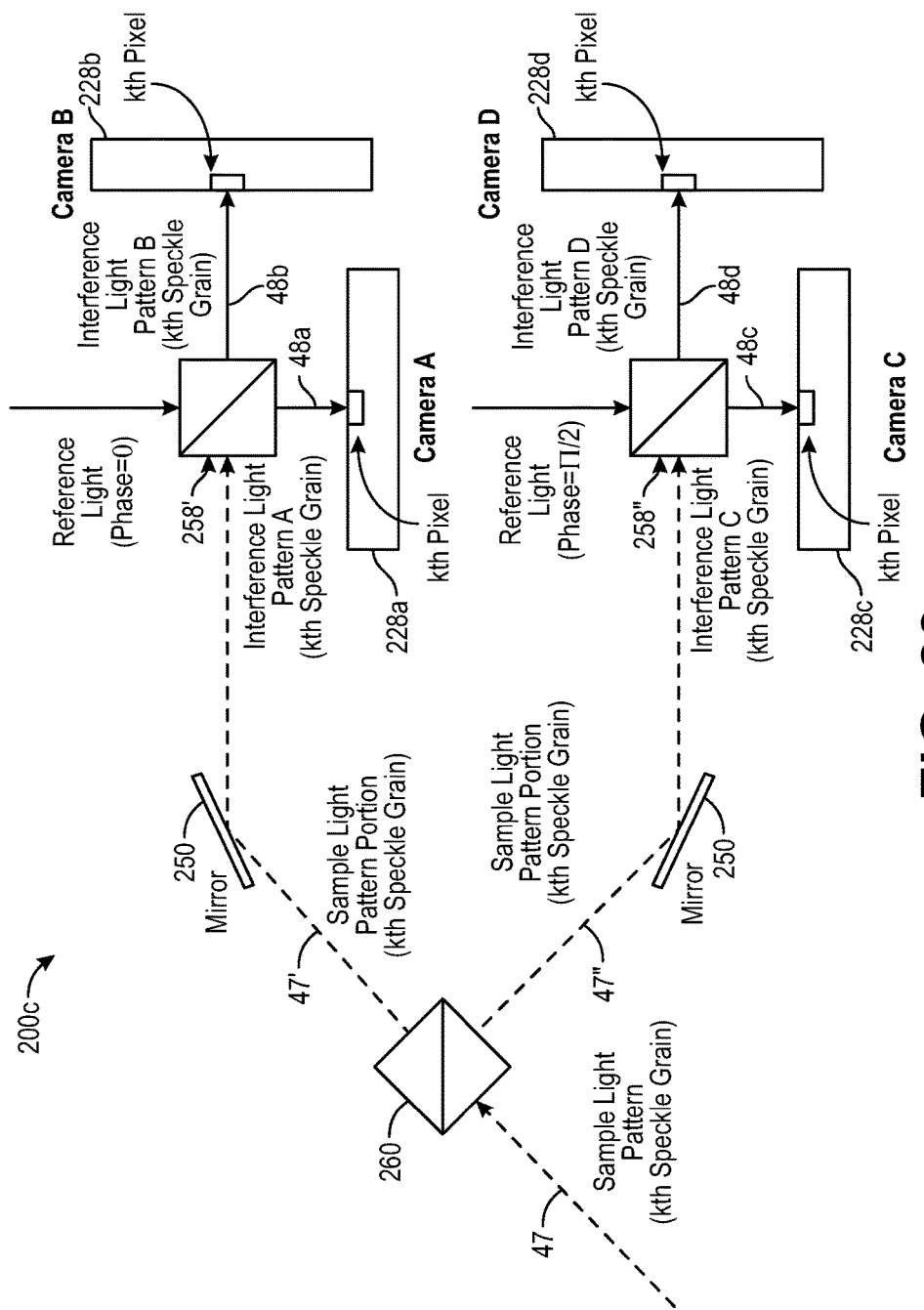
FIG. 23 is a block diagram of the optical detection assembly of FIG. 22, particularly showing the generation and detection of a kth speckle grain of an interference pattern.

In the same manner as the cameras 228a, 228b are optically aligned with each other in the optical detection assembly 200a, the cameras 228a-228d of the optical detection assembly 200c are similarly optically aligned with each other, such that any given pixels of the cameras 228a-228d have a known one-to-one correspondence with each other. That is, as illustrated in FIG. 23, the kth speckle grain of the sample light pattern 47 (after it is split into the first sample light pattern portion 47a) interferes with the reference light 42a with a phase of 0 to generate a kth speckle grain of the interference light pattern 48a that is detected by the kth pixel of the camera 228a; the same kth speckle grain of the sample light pattern 47 (after it is split into the first sample light pattern portion 47a) interferes with the reference light 42b with a phase of π to generate a kth speckle grain of the interference light pattern 48b that is detected by the kth pixel of the camera 228b; the same kth speckle grain of the sample light pattern 47 (after it is split into the second sample light pattern portion 47b) interferes with the reference light 42c with a phase of π/2 to generate a kth speckle grain of the interference light pattern 48c that is detected by the kth pixel of the camera 228c; and the same kth speckle grain of the sample light pattern 47 (after it is split into the second sample light pattern portion 47d) interferes with the reference light 42d with a phase of 3π/2 to generate a kth speckle grain of the interference light pattern 48d that is detected by the kth pixel of the camera 228d.

Since each kth pixel of the cameras 228a-228d have known correspondences via optical alignment, the quadruplet of intensity values detected by the kth pixels of the cameras 228a-228d serve as the analog to the four intensity values that would normally be stored by the kth pixel in the four bins of a lock-in camera.

At each corresponding quadruplet of kth pixels, the optical power received by the respective cameras 228a, 228b is equal to the summation of the power of the reference light 42a ($P_{reference}$A and $P_{reference}$B) input into the first beam splitter 258', the sample light pattern 47 ($P_{sample}$A and $P_{sample}$B) input into the first beam splitter 258', and an interference term between the reference light 42 and sample light pattern 47 ($P_{interfere}$A and $P_{interfere}$B); and the optical power received by the respective cameras 228c, 228d is equal to the summation of the power of the reference light 42b ($P_{reference}$C and $P_{reference}$D) input into the second beam splitter 258", the sample light pattern 47 ($P_{sample}$C and $P_{sample}$D) input into the second beam splitter 258", and an interference term between the reference light 42 and sample light pattern 47 ($P_{interfere}$C and $P_{interfere}$D). By the power conservation, the interference terms $P_{interfere}$A and $P_{interfere}$B are 180 degrees out of phase for cameras 228a, 228b, and the interference terms $P_{interfere}$C and $P_{interfere}$D are 180 degrees out of phase for cameras 228c, 228d.

It follows that, in the context of pulsed UOT, the power detected at a kth pixel for the first camera 228a can be expressed as:

$$\text{Value}_{1,k} = P_{background} + P_{signal} + P_{reference} + 2(P_{signal} \times P_{reference})^{1/2} \times \cos(\varphi_{unknown1,\,speckle\,k}) + 2(P_{signal} \times P_{background})^{1/2} \times \cos(2\pi \times f_{us} - \varphi_{unknown2,\,speckle\,k}) + 2(P_{reference} \times P_{background})^{1/2} \times \cos(2\pi \times f_{us} - \varphi_{unknown3,\,speckle\,k}); \quad [22]$$

the power detected at the corresponding kth pixel of the second camera 228b can be expressed as:

$$\text{Value}_{2,k} = P_{background} + P_{signal} + P_{reference} + 2(P_{signal} \times P_{reference})^{1/2} \times \cos(\varphi_{unknown1,\,speckle\,k} + \pi) + 2(P_{signal} \times P_{background})^{1/2} \times \cos(2\pi \times f_{us} - \varphi_{unknown2,\,speckle\,k} + \pi) + 2(P_{reference} \times P_{background})^{1/2} \times \cos(2\pi \times f_{us} - \varphi_{unknown3,\,speckle\,k} + \pi); \quad [23]$$

the power detected at the corresponding kth pixel of the second camera 228b can be expressed as:

$$\text{Value}_{3,k} = P_{background} + P_{signal} + P_{reference} + 2(P_{signal} \times P_{reference})^{1/2} \times \cos(\varphi_{unknown1,\,speckle\,k} + \pi/2) + 2(P_{signal} \times P_{background})^{1/2} \times \cos(2\pi \times f_{us} - \varphi_{unknown2,\,speckle\,k} + \pi/2) + 2(P_{reference} \times P_{background})^{1/2} \cos(2\pi \times f_{us} - \varphi_{unknown3,\,speckle\,k} + \pi/2); \text{ and} \quad [24]$$

the power detected at the corresponding kth pixel of the second camera 228d can be expressed as:

$$\text{Value}_{4,k} = P_{background} + P_{signal} + P_{reference} + 2(P_{signal} \times P_{reference})^{1/2} \times \cos(\varphi_{unknown1,\,speckle\,k} + 3\pi/2) + 2(P_{signal} \times P_{background})^{1/2} \times \cos(2\pi \times f_{us} - \varphi_{unknown2,\,speckle\,k} + 3\pi/2) + 2(P_{reference} \times P_{background})^{1/2} \times \cos(2\pi \times f_{us} - \varphi_{unknown3,\,speckle\,k} + 3\pi/2), \quad [25]$$

where $P_{background}$ represents light at frequency $f + f_{us}$ that has not been tagged with the ultrasound 32; $P_{signal}$ represents light at frequency f that has been tagged with the ultrasound 32; $P_{reference}$ represents the reference light at frequency f; $\varphi_{control}$ is the phase shift introduced into the reference light 42; and $\varphi_{unknown1,\,speckle\,k}$, $\varphi_{unknown2,\,speckle\,k}$, and $\varphi_{unknown3,\,speckle\,k}$ are random phases at the kth speckle grain at the time of measurement, which originates via multiple scattering of coherent light inside the tissue.

The terms $2(P_{signal} \times P_{background})^{1/2} \times \cos(2\pi \times f_{us} - \varphi_{unknown2}) + 2(P_{reference} \times P_{background})^{1/2} \times \cos(2\pi \times f_{us} - \varphi_{unknown3})$ oscillate at the frequency $f_{us}$, and are not detected by the cameras 228a, 228b, and thus, can be ignored. As such, equations [22]-[25] can be respectively reduced to:

$$\text{Value}_{1,k} = P_{background} + P_{signal} + P_{reference} + 2(P_{signal} \times P_{reference})^{1/2} \times \cos(\varphi_{unknown}); \quad [26]$$

$$\text{Value}_{2,k} = P_{background} + P_{signal} + P_{reference} + 2(P_{signal} \times P_{reference})^{1/2} \times \cos(\varphi_{unknown} + \pi); \quad [27]$$

$$\text{Value}_{3,k} = P_{background} + P_{signal} + P_{reference} + 2(P_{signal} \times P_{reference})^{1/2} \times \cos(\varphi_{unknown} + \pi/2); \quad [28]$$

and $$\text{Value}_{4,k} = P_{background} + P_{signal} + P_{reference} + 2(P_{signal} \times P_{reference})^{1/2} \times \cos(\varphi_{unknown} + 3\pi/2). \quad [29]$$

These equations can be expressed as $A + B \times \cos(\varphi_{unknown})$. Both the amplitude B (i.e., the interference term $2(P_{signal} \times P_{reference})^{1/2}$) and the unknown phase $\varphi_{unknown}$ can be extracted by solving the resulting four equations using the standard trigonometric identities, and determining power of the signal light $P_{signal}$ can be determined (either in the absolute sense or relative sense) from the extracted term interference term $2(P_{signal} \times P_{reference})^{1/2}$ using a known scaling relationship with the known or independently measurable power of the reference light $P_{reference}$.

As with the four-bin detection scheme described above with respect to the UOT system 10, with an N number of pixels, the signal-to-noise ratio (SNR) scales with $N^{1/2}$ in accordance with equation [6] set forth above.

Figure 24:
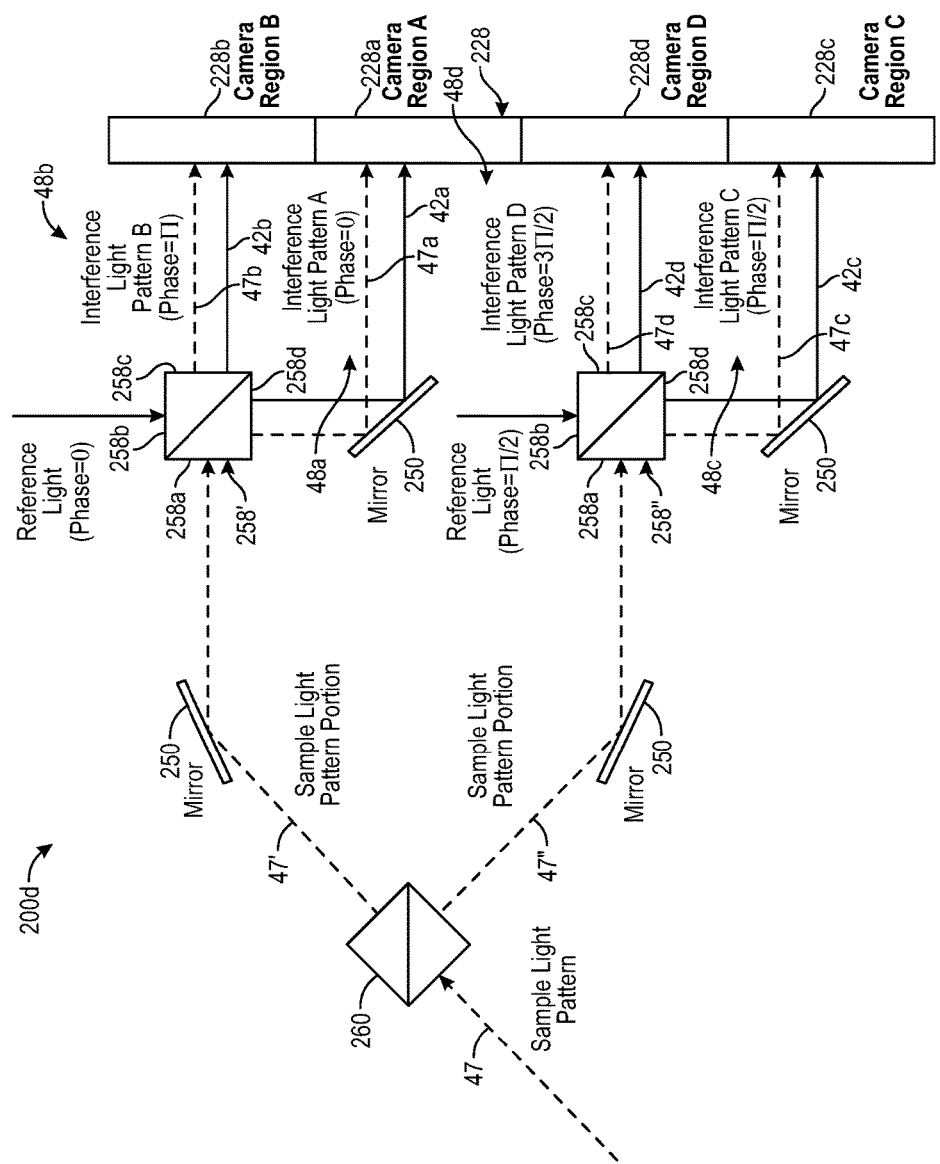
FIG. 24 is a block diagram of yet another specific embodiment of the optical detection assembly of FIG. 16.

Although the optical detection assembly 200c has been described and illustrated as comprising detector arrays that take the form of separate cameras 228a-228d (in effect, the detector arrays are mechanically disposed on four separate camera microchips), an optical detection assembly 200d can comprise detection arrays that take the form of a single camera 228 (in effect, the four detector arrays are mechanically disposed on a single camera microchip), as illustrated in FIG. 24.

As with the optical detection assembly 200c, the beam splitter 260 of the optical detection assembly 200d splits the sample light pattern 47 into first and second sample light pattern portions 47', 47", and the first and second beam splitter/combiners 258', 258" of the optical detection assembly 200d split reference light 42 respectively into reference light 42 having an M number of different phase relative to the sample light pattern 47 (and in this case, reference light 42a-42d respectively having four different phases of 0, π, π/2, and 3π/2), and concurrently combining the sample light pattern portions 47a-47d and the reference light 42a-42d to respectively generate an M number of interference light patterns 48 (in this case, four interference light patterns 48a ("Interference Light Pattern A"), 48b ("Interference Light Pattern B"), 48c ("Interference Light Pattern C"), 48d ("Interference Light Pattern D").

However, instead of respectively projecting the interference light patterns 48-48d onto four cameras, the beam splitter/combiners 258', 258" of the optical detection assembly 200d project the interference light patterns 48a-48d from their respective output ports onto four separate spatial regions 228a-228d of the same camera 228. To this end, the optical detection assembly 200d comprises two more angled mirrors 250 configured for respectively directing the interference light pattern 48a, 48c from the first output ports 258c of the first and second beam splitter/combiners 258', 258" toward the same plane to which the interference light patterns 48b, 48d are directed, i.e., towards the single camera 228.

Figure 25:
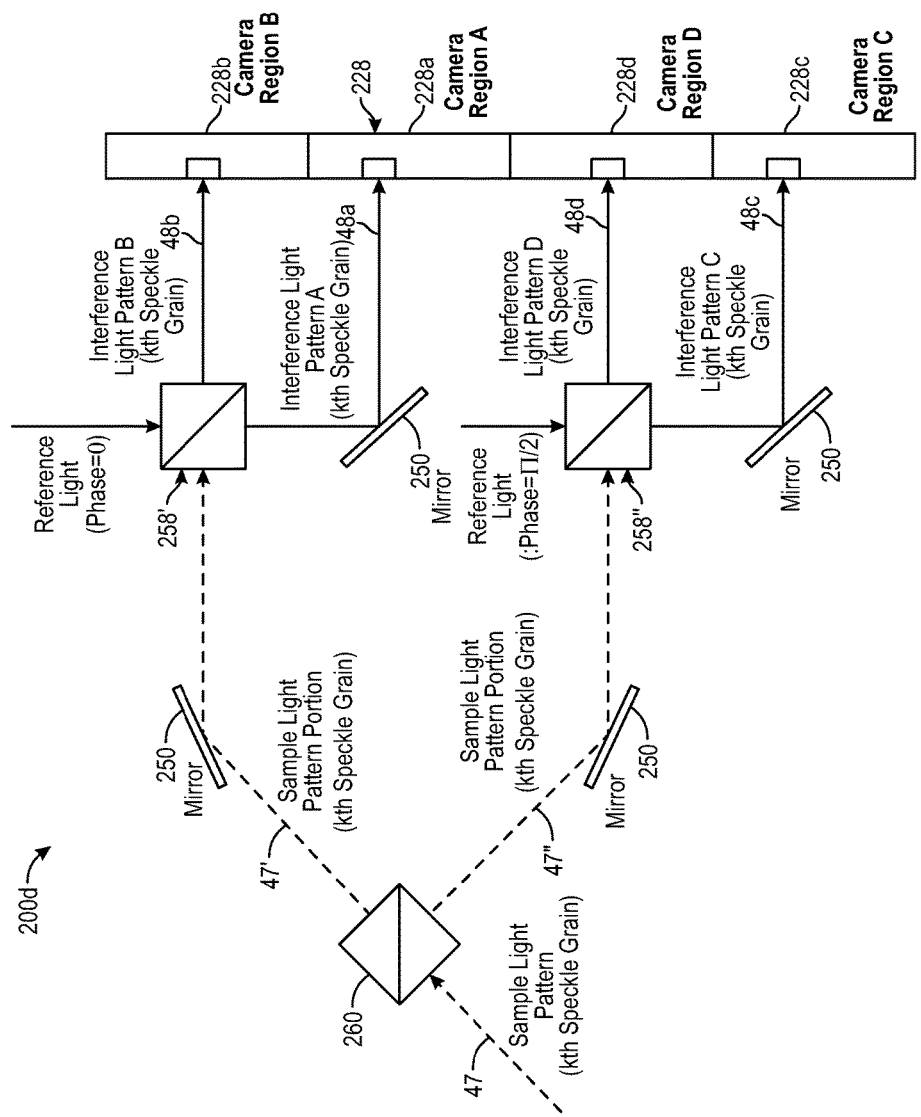
FIG. 25 is a block diagram of the optical detection assembly of FIG. 24, particularly showing the generation and detection of a kth speckle grain of an interference pattern.

In the same manner as the cameras 228a-228d are optically aligned with each other in the optical detection assembly 200c, the spatial regions 228a-228d of the single camera 228 of the optical detection assembly 200d are optically aligned with each other, such that any given pixels on the spatial regions 228a-228d have a known one-to-one correspondence with each other. That is, as illustrated in FIG. 25, the kth speckle grain of the sample light pattern portion 47 (after being split into the first sample light pattern portion 47a) interferes with the reference light 42a with no phase shift (i.e., 0 phase) to generate a kth speckle grain of the interference light pattern 48a that is detected by the spatial region 228a of the camera 228; the same kth speckle grain of the sample light pattern 47 (after being split into the first sample light pattern portion 47a) interferes with the reference light 42b with a phase shift (i.e., π) to generate a corresponding kth speckle grain of the interference light pattern 48b that is detected by the kth pixel of the spatial region 228b of the camera 228; the same kth speckle grain of the sample light pattern 47 (after being split into the second sample light pattern portion 47b) interferes with the reference light 42c with a phase shift (i.e., π/2) to generate a corresponding kth speckle grain of the interference light pattern 48c that is detected by kth pixel of the spatial region 228c of the camera 228; and the same kth speckle grain of the sample light pattern 47 (after being split into the second sample light pattern portion 47b) interferes with the reference light 42d with a phase shift (i.e., 3π/2) to generate a corresponding kth speckle grain of the interference light pattern 48d that is detected by the kth pixel of the spatial region 228d of the camera 228.

The power of the signal light $P_{signal}$ can be determined in accordance with equations [26]-[29], where $Value_{1,k}$ is the power detected at a kth pixel for the first region 228a of the camera 228, $Value_{2,k}$ is the power detected at a kth pixel for the second region 228b of the camera 228; $Value_{3,k}$ is the power detected at a kth pixel for the second region 228c of the camera 228; and $Value_{4,k}$ is the power detected at a kth pixel for the fourth region 228d of the camera 228.

Thus, it can be appreciated that the optical detection assemblies 200a-200d can be used in place of a conventional lock-in camera for UOT (or DOPC or snake photon OCT). In essence, the optical detection assemblies 200a-200d serve as drop-in replacements for conventional lock-in cameras. Instead of using two or more optical pulses that are interferometrically phase stepped and captured in separate lock-in camera bins to perform a single "ultrasound tagged photon" quantification in UOT, the optical detection assemblies 200a-200d use a single optical pulse and a single camera frame for the same purpose. An arithmetic function (e.g., the absolute differencing and summation operations described above with respect to the optical detection assemblies 200a and 200b) can be performed on the arrays of values respectively detected by the arrays of pixels by a processor (e.g., the same processor used to determine the physiologically-dependent optical parameter of the target voxel or a separate circuit board, such as, e.g., an application specific circuit board (ASIC) or a field-programmable field array (FPGA) customized to perform the processing). Alternatively, as will be described in further detail below, processing circuitry for performing the arithmetic function can be mechanically integrated into the camera microchip itself.

As discussed above, it is important that detector arrays be aligned pixel-by-pixel, whether the detector arrays are on separate cameras or spatial regions of a single camera. This can be accomplished, for instance, using image correlation methods and automated feedback find the optimal alignment configuration of the system. For example, a small bead may be imaged on each of the detector arrays (cameras or regions of the camera), pixels that the bead appears on can be recorded, and this information can be stored in a look-up table to establish pixel-to-pixel correspondences. Alternatively, spatial light modulators (SLMs) may be used to project patterns onto each detector array, and pixels corresponding to defined parts of each pattern on each detector array may be stored in a look-up table to establish pixel-to-pixel correspondences. The cameras and any mirrors may be physically re-positioned during these calibration processes, e.g., using piezo-positioners or micro-electro-mechanical systems (MEMs) to physically establish a desired correspondence relationship between the pixels.

Although the UOT system 210 has been described as computing the intensity values $Value_k$ of the speckle grains of each interference light pattern 48 in order to obtain the power of the light signal $P_{signal}$, it should be appreciated that the UOT system 10 may alternatively or optionally compute the random phases $\varphi_{unknown}$ of the kth speckle grains of each interference light pattern 48 in order to obtain the phase across the wavefront of the light signal, e.g., for purposes of performing DOPC as described above, or for detecting optical phases in the target voxel 14 due to optical scatter changes by determining temporal changes in the wavefront phases of the signal light in accordance with equation [14] discussed above, wherein instead of using four bins of a lock-in camera, four pixels of optically registered detector arrays (i.e., four different cameras or four different spatial regions of a single camera).

Figure 26:
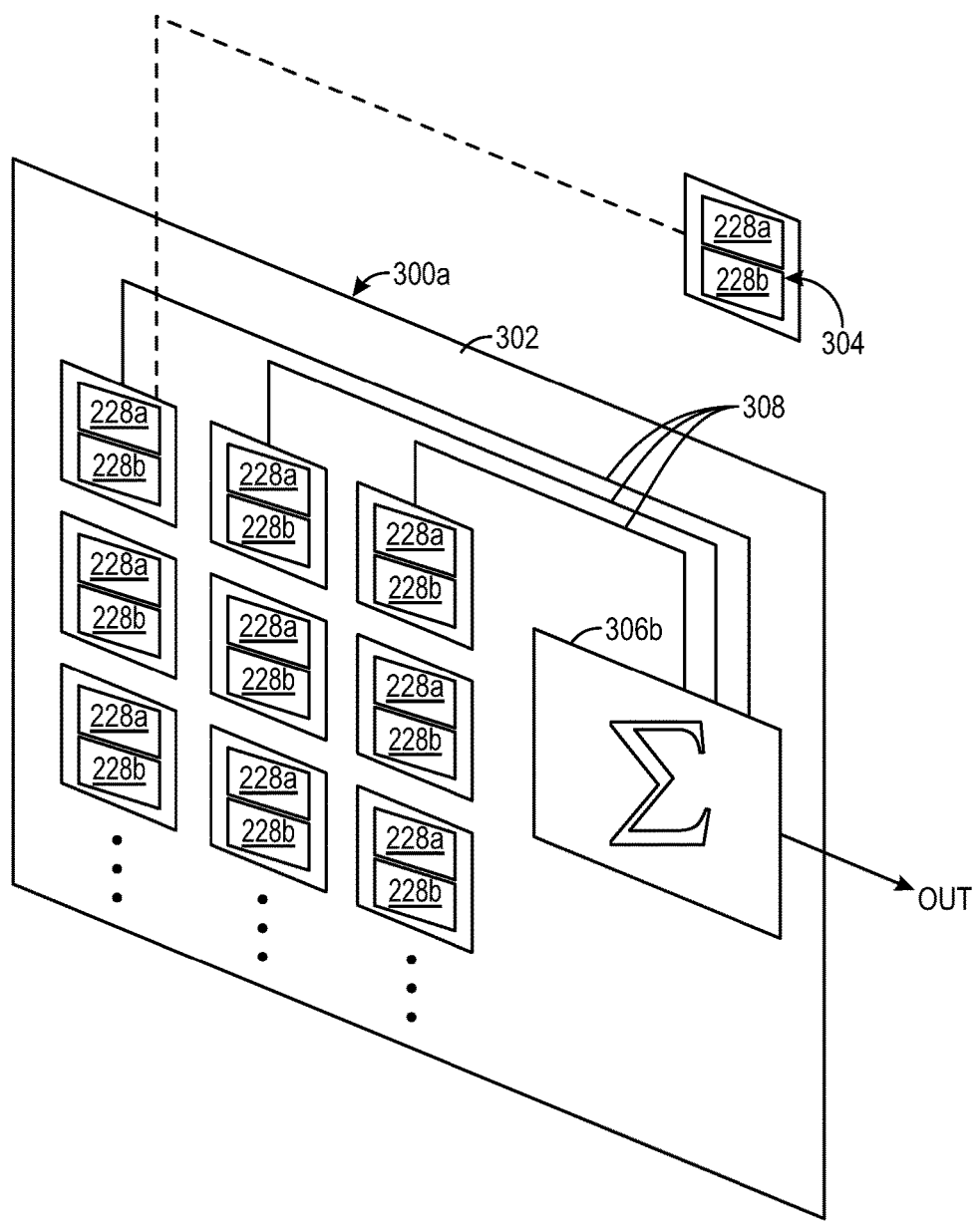
FIG. 26 is a perspective view of one embodiment of a camera microchip that can be used in an optical detection assembly.
Figure 27:
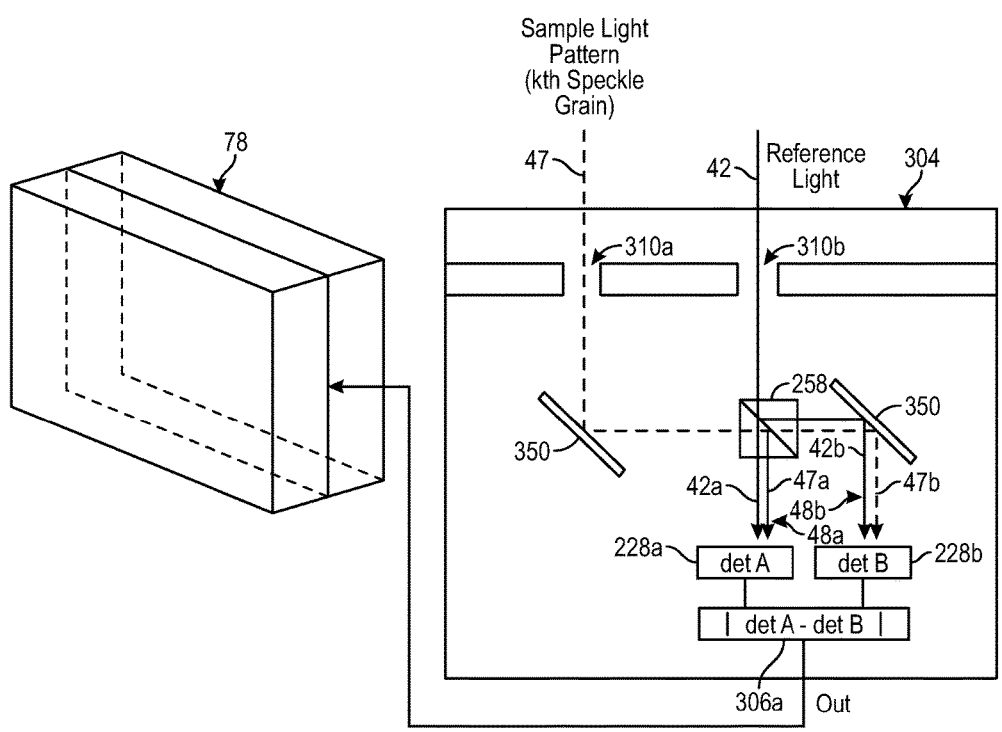
FIG. 27 is a block diagram of a pixel of the camera microchip of FIG. 26.

Referring now to FIG. 26, one embodiment of a camera microchip 300a that can be incorporated into an optical detection assembly comprises a substrate 302 and an array of N pixels 304, each of which contains miniaturized, integrated micro-optics, such that light splitting and combining function and interference pattern detection functions are performed at the pixel-level, as illustrated in FIG. 27, as described in further detail below. The camera microchip 300a essentially is a custom opto-electronic camera that performs interferometry at a pixel level.

To this end, the camera microchip 300a comprises an M number of optically registered detector arrays 228 mechanically integrated within the substrate 302 (and in this case, two detector arrays 228a, 228b). In the illustrated embodiment, the two detector arrays 228a, 228b are interlaced with each other, such that corresponding detectors of the arrays 228a, 228b are arranged as closely spaced side-by-side detector pairs (i.e., each detector pair comprises two corresponding detectors 228a, 228b), each of which represents a pixel 304 of the camera microchip 300a. Thus, the camera microchip 300a comprises an array of pixels 304, each comprising two corresponding detectors 228a, 228b. In the same manner described above with respect to the optical detection assembly 200d, the detector array 228a is configured for detecting an N number of spatial components of the interference light pattern 46a (one spatial component per pixel 304), and outputting a respective N number of intensity values for the respective spatial components (one intensity value "det A" shown in FIG. 27); and the detector array 228b is configured for detecting an N number of spatial components of the interference light pattern 46b (one spatial component per pixel 304), and outputting a respective N number of intensity values for the respective spatial components (one intensity value "det B" shown in FIG. 27).

The camera 300a further comprises processing circuitry 306 integrated within the substrate 302 for performing the arithmetic function on the respective intensity values respectively output by pixels containing corresponding detectors of the respective detector arrays 228a, 228b, and in this case, computing the sum of the absolute differences between the corresponding kth intensity values of each pixel. In the illustrated embodiment, local processing circuitry 306a (shown in FIG. 27) is distributed amongst the pixels 302, such that the absolute difference of corresponding intensity values (|det A-det B|) is computed locally at each respective pixel 302, and processing centralized circuitry 306b is remote from the detector arrays 228a, 228b for computing the sum of these absolute differences, and outputting a single value representative of the $P_{signal}$ in equations [20] or [21]. Any averaging of the absolute difference summing function, if necessary, can be conveniently and quickly performed off-chip as a single computation having one input value and one output value. The outputs of the local processing circuitry 306a are coupled to respective inputs of the remote processing circuitry 306b via a respective N number of electrically conductive traces 308. Thus, the remote processing circuitry 306b comprises an N number of inputs, and one output for one value (i.e., $P_{signal}$).

It should be noted that by localizing a portion of the processing circuitry with the individual pixels, the number of electrically conductive traces 308 is minimized. However, the absolute difference summing function can be alternatively performed in the remote processing circuitry 306b, in which case, an increased number of electrically conductive traces 308 would be required to connect the outputs of the individual detectors to the processing circuitry 306b.

The camera microchip 300a further comprises an array of beam splitter/combiners 258, an array of sample input ports 310a, and an array of reference input ports 310b integrated within the substrate 302, such that, as illustrated in FIG. 27, each pixel 302 has a dedicated splitter/combiner 258, a dedicated sample input port 310a, a dedicated reference input port 310b, and a dedicated pair of corresponding detectors 228a, 228b (one from the detector array 228a, and the other from the detector array 228b).

The array of sample input ports 310a is configured for respectively receiving the sample light pattern 47, and the array of reference input ports 310b is configured for receiving the reference light 42. In the same manner described above with respect to the optical detection assembly 200a, the array of beam splitter/combiners 258 is configured for splitting the reference light 42 into reference light 42a, 42b respectively having two different phases of 0 and $\pi$, splitting the spatial component of the sample light pattern 47 respectively into the sample light pattern portions 47a, 47b, and concurrently combining the sample light portions 47a, 47b and the reference light 42a, 42b to respectively generate two interference light patterns 48a, 48b. However, in this case, the camera microchip 300a locally performs this entire process on a pixel-by-pixel basis.

Thus, for each pixel, a spatial component of the sample light pattern 47 enters the sample input port 310a, where it is split by the beam splitter/combiner 258 into a reflected spatial component of a sample pattern portion 47a and a transmitted spatial component of a sample light pattern portion 47b, and the reference light 42 enters the reference input port 310b, where it is split by the beam splitter/combiner 258 into transmitted reference light 42a and reflected reference light 42b. In a simultaneous manner, the reflected spatial component of the sample light pattern portion 47a interferes with the transmitted reference light 42a to generate a respective spatial component of the interference light pattern 48a, and the transmitted spatial component of the sample light pattern portion 47b interferes with the reflected reference light 42b to generate a respective spatial component of the interference light pattern 48a.

In the illustrated embodiment, the beam splitter/combiner 258 is in the direct linear path of the sample input port 310a, but laterally offset from the direct linear path of the reference input port 310b. In this case, the camera microchip 300 comprises an angled mirror 250 configured for redirecting the reference light 47 from the reference input port 310b towards the beam splitter/combiner 258. Alternatively, if the beam splitter/combiner 258 is in the direct linear path of the reference input port 310b, but laterally offset from the direct linear path of the sample input port 310a, the angled mirror 350 can instead be configured for redirecting the spatial component of the sample light pattern 47 from the sample input port 310a towards the beam splitter/combiner 258.

For each pixel, the detectors 228a, 228b are configured for concurrently detecting the respective spatial components of the two interference light patterns 48a, 48b, and generating two values representative of intensities of the two respective spatial components of the interference light patterns 48a, 48b. Thus, the sample light field 47 and reference light 42 combine to project the respective spatial component of the interference light pattern 48a onto the detector 228a, and likewise to project the respective spatial component of the interference light pattern 48b onto the detector 228b, but with respect to a different phase of the reference light 42.

As with the optical detection assembly 200a described above, the detectors 228a, 228b are optically aligned with each other, such that they have a known one-to-one correspondence with each other for that pixel. That is, a spatial component ("speckle k," indicating the kth speckle grain of the speckle light field) of the sample light pattern 47 interferes with the reference light 42a with no phase shift (i.e., 0) to generate a kth speckle grain of the interference light pattern 48a that is detected by the detector 228a, and the same kth speckle grain of the sample light pattern 47 interferes with the reference light 42b with a phase shift (i.e., π) to generate a corresponding kth speckle grain of the interference light pattern 48b that is detected by the detector 228b. Thus, since the detectors 228a, 228b, in effect, are positioned below the same pixel and hence the same speckle grain, the pair of intensity values outputted by the detectors 228a, 228b serve as the analog to the pair of intensity values that would normally be stored by the kth pixel in the two bins of a lock-in camera. It should be appreciated that although FIG. 27 illustrates one speckle "k," an equivalent process for measuring the speckle k takes place for all speckles k in parallel in the manner of imaging an entire speckle light field. It should be appreciated that auto-alignment mechanisms are not necessary to optically align the detectors 228a, 228b, since they are integrated within one pixel.

However, it is important that the spatial components of the sample light pattern 47 be respectively optically aligned with the sample input ports 310a, and that the reference light 40 only enter the reference input ports 310b. To this end, and with reference to FIG. 28, the camera microchip 300 of FIGS. 26 and 27 can be incorporated into an optical detection assembly 200e that additionally comprises a first grate 262a configured for transforming the sample light pattern 47 into an array of sample light pattern beamlets 47' (corresponding to the spatial components), a first lens 264a configured for focusing the array of reference beamlets 47' into the array of reference input ports 310a, a second grate 262b configured for transforming the reference light 42 into an array of reference light beamlets 42', and a second lens 264b configured for focusing the array of reference light beamlets 42' into the array of reference input ports 310b. The optical detection assembly 200e may further comprise a light combiner 266 that transmits the focused sample light pattern beamlets 42' from the first lens 264a into the sample input ports 310a on the camera microchip 300, and that reflects the focused reference light pattern beamlets 47' from the second lens 264b into the reference input ports 310b on the camera microchip 300a, or alternatively, vice versa.

Thus, the optical detection assembly 200e ensures that the kth speckle grain of the sample light pattern 47 enters the sample input port 310a of the kth pixel 302, while avoiding the reference input port 310b, and likewise, ensures that the reference light 42 enters the reference input ports 310a while avoiding the sample input ports 310a.

Figure 28:
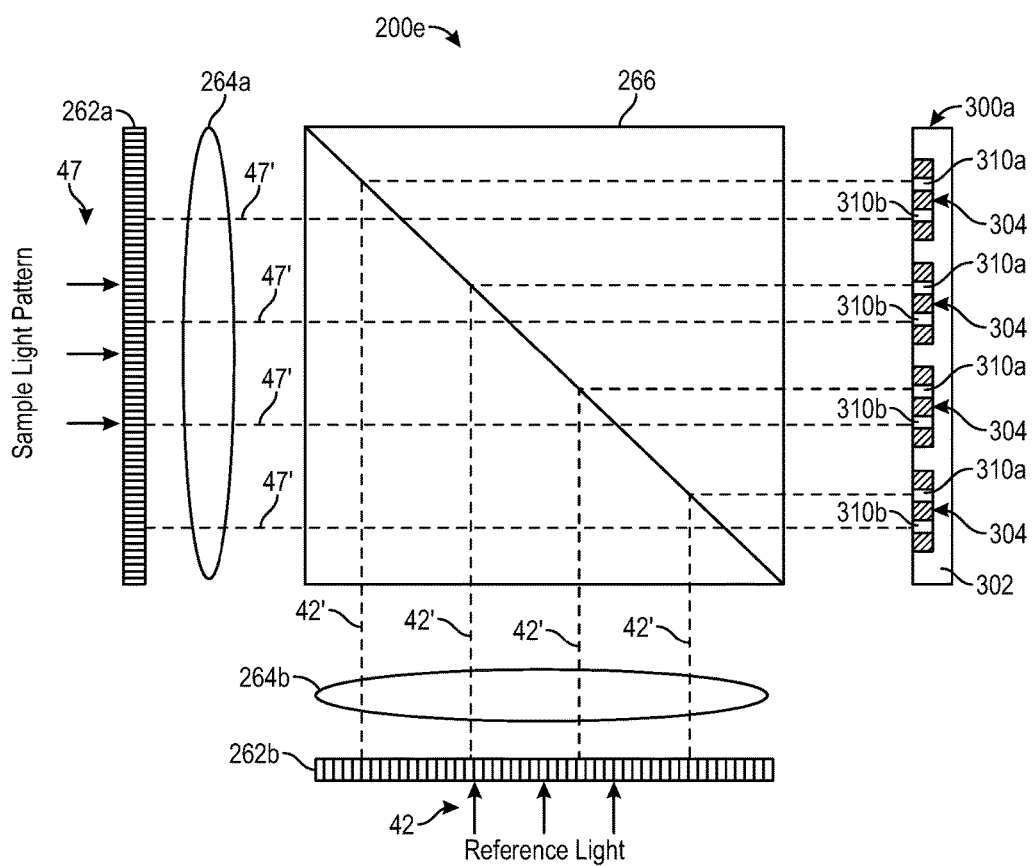
FIG. 28 is a block diagram of an optical detection assembly that uses the camera microchip of FIG. 26.

Referring now to FIG. 28, another embodiment of a camera microchip 300b that can be incorporated into an optical detection assembly for performing DOPC will be described. The camera microchip 300b is similar to the camera microchip 300a described above, except that it has an integrated camera-spatial-light-modulator architecture that performs phase conjugation using an SLM array 78 to perform optical phase conjugation of the signal light 44 in a digital optical phase conjugation (DOPC) technique in the same manner described above with respect to FIGS. 9a-9b and 10a-10b, i.e., to boost the sensitivity of the pulsed UOT detection by extracting the phase of the signal light 44 in the pulsed UOT detection scheme, computing the phase conjugate of the wavefront of the signal light 44, and feeding it back through an SLM array 78 to achieve enhanced light focusing at the target voxel 14. The pixels 302 of the camera microchip 300b are co-registered (e.g., pixel-by-pixel) with the SLM array 78, i.e., in direct alignment with the pixels of the SLM array 78, such that the outputs of the local processing circuitry 306a are coupled to respective inputs of the pixels of the SLM array 78. The SLM array 78 may be built directly on top of the detector array 228 or detector arrays 228 to create a phase conjugation array.

Furthermore, the remote processing circuitry 306b is not required, and therefore not included within the camera microchip 300b, for summing the absolute difference values output by the array of pixels 302. Instead, like the camera microchip 300a, the camera microchip 300b only includes local processing circuitry 306a is distributed amongst the pixels, such that the absolute difference of corresponding intensity values is computed locally at each respective pixel 302.

Notably, the increased processing speed enabled by the local data processing architecture of the camera microchip 300b lends itself well to DOPC detection, which additionally requires phase conjugation computation that would otherwise be slowed if data transfer and off-chip computation were required. Thus, phase conjugation can be performed directly on-chip without the need to shuttle information off-chip or to perform off-chip computation, thereby enabling extremely rapid phase conjugation. Because the camera microchip 300b can perform phase conjugation very rapidly, must faster than the speckle decorrelation time, even for imaging many centimeters inside a dynamic, strongly scattering biological specimen, such as the human brain, it would enable scattering correction methods, such as DOPC, to be performed for focusing light many centimeters inside such dynamic medium, effectively overcoming the limit on DOPC depth currently posed by speckle decorrelation.

Figure 29A:
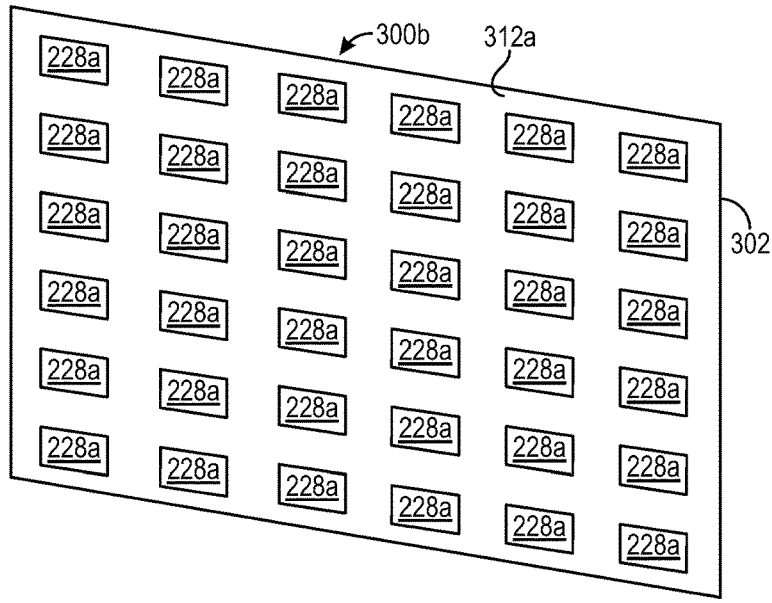
FIGS. 29a and 29b are perspective views of another embodiment of a camera microchip that can be used in an optical detection assembly.
Figure 29B:
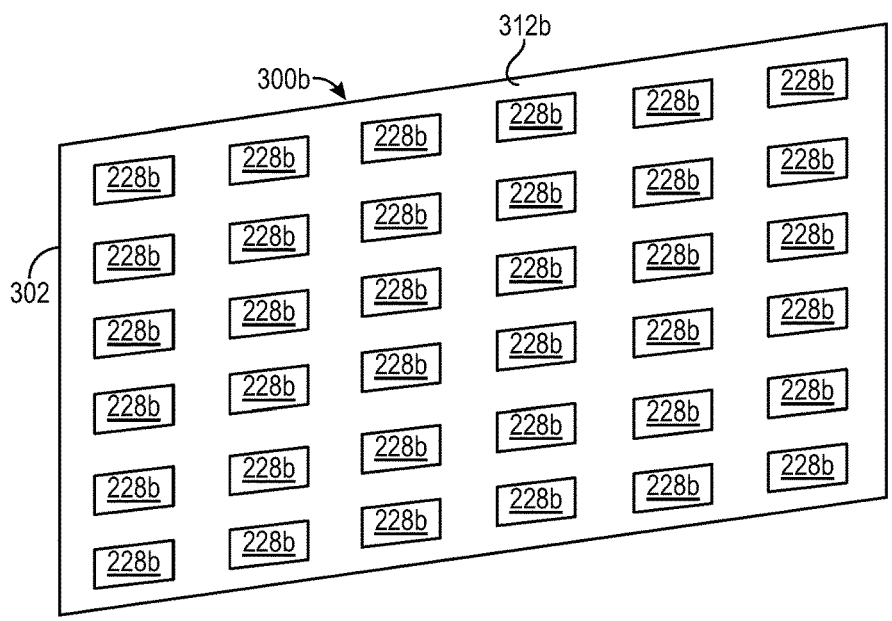
Figure 30:
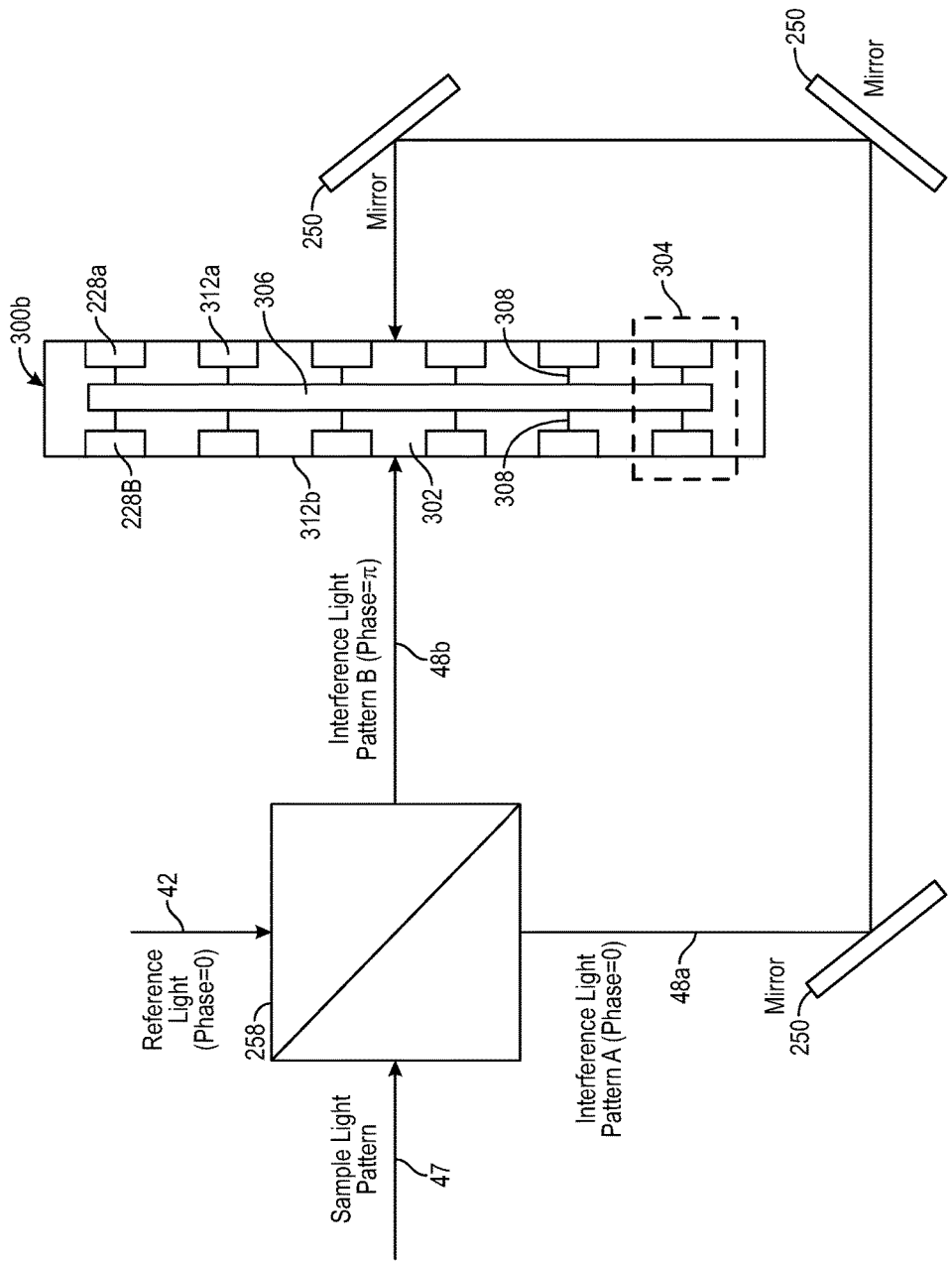
FIG. 30 is a side view of the camera microchip of FIGS. 29a and 29b.

Referring now to FIGS. 29a, 29b, and 30, another embodiment of a camera microchip 300b that provides a simplified design that does not require miniaturized, integrated micro-optics that perform the light splitting and combining functions at the pixel-level, but rather is designed to be used with a single off-chip beam splitter/combiner 258 as part of an optical detection assembly 200f.

Like the camera microchip 300a, the camera microchip 300b comprises a substrate 302 and two optically registered detector arrays 228a, 228b mechanically integrated within the substrate 302 to form detector pairs, each of which comprises two corresponding detectors 228a, 228b to form a pixel 304. However, unlike the camera microchip 300a, the detector arrays 228a, 228b are not interlaced with each other, but rather are respectively disposed on opposite sides 312a, 312b of the substrate 302 to form detector pairs, each of which comprises two corresponding detectors 228a, 228b to form the pixel 304. Thus, the camera microchip 300b comprises an N number of pixels 304, each comprising two corresponding detectors 228a, 228b.

In the same manner described above with respect to the optical detection assembly 200d, the detector array 228a is configured for detecting an N number of spatial components of the interference light pattern 46a, and outputting a respective N number of intensity values for the respective spatial components, and the detector array 228b is configured for detecting an N number of spatial components of the interference light pattern 46b, and outputting a respective N number of intensity values for the respective spatial components.

However, in this case, the interference light patterns 48a, 48b are projected onto the detector arrays 228a, 228b on opposite sides of the substrate 302. As with the optical detection assembly 200a, the beam splitter/combiner 258 is configured for splitting the reference light 42 respectively into reference light 42a, 42b respectively having two different phases of 0 and π, splitting the sample light pattern 47 respectively into sample light pattern portions 47a, 47b, and concurrently combining the sample light pattern portions 47a, 47b and the reference light 42a, 42b to respectively generate two interference light patterns 48a, 48b.

The beam splitter/combiner 258 projects the interference light pattern 48a directly onto the detector array 228a on one side of the substrate 302 of the camera microchip 300b. The optical detection assembly 200f comprises angled mirrors 250 configured for redirecting the interference light pattern 48a from the beam splitter/combiner 258 towards the detector array 228a on the opposite side 312a of the substrate 302 of the camera microchip 300b.

As best shown in FIG. 30, like the camera microchip 300a, the camera microchip 300b further comprises processing circuitry 306 integrated within the substrate 302 for performing the arithmetic function on the respective intensity values respectively output by pixels containing corresponding detectors of the respective detector arrays 228a, 228b, and in this case, computing the sum of the absolute differences between the corresponding kth intensity values of each pixel and outputting a single value representative of $P_{signal}$ in equations [20] or [21]. The outputs of the local processing circuitry 306a are coupled to respective inputs of the remote processing circuitry 306b via a respective N number of electrically conductive traces 308. Thus, the remote processing circuitry 306b comprises an N number of inputs, and one output for one value (i.e., $P_{signal}$). As can be appreciated the processing circuitry 306 can be conveniently located between the respective detector arrays 228a, 228b, thereby providing an efficient and simplistic means of routing signals from the detector arrays 228a, 228b to the processing circuitry 306. Moreover, any average of the absolute value of the difference or other computation can be performed through the processing circuitry 306 (which may be implemented by local analog and/or mixed-signal circuitry) in the space between the two detector arrays 228a, 228b, minimizing the amount of long-range signal routing and the power consumption associated with analog to digital conversion and other operations, and thus making the system more space and power efficient as it scales to high pixel counts.

Figure 31:
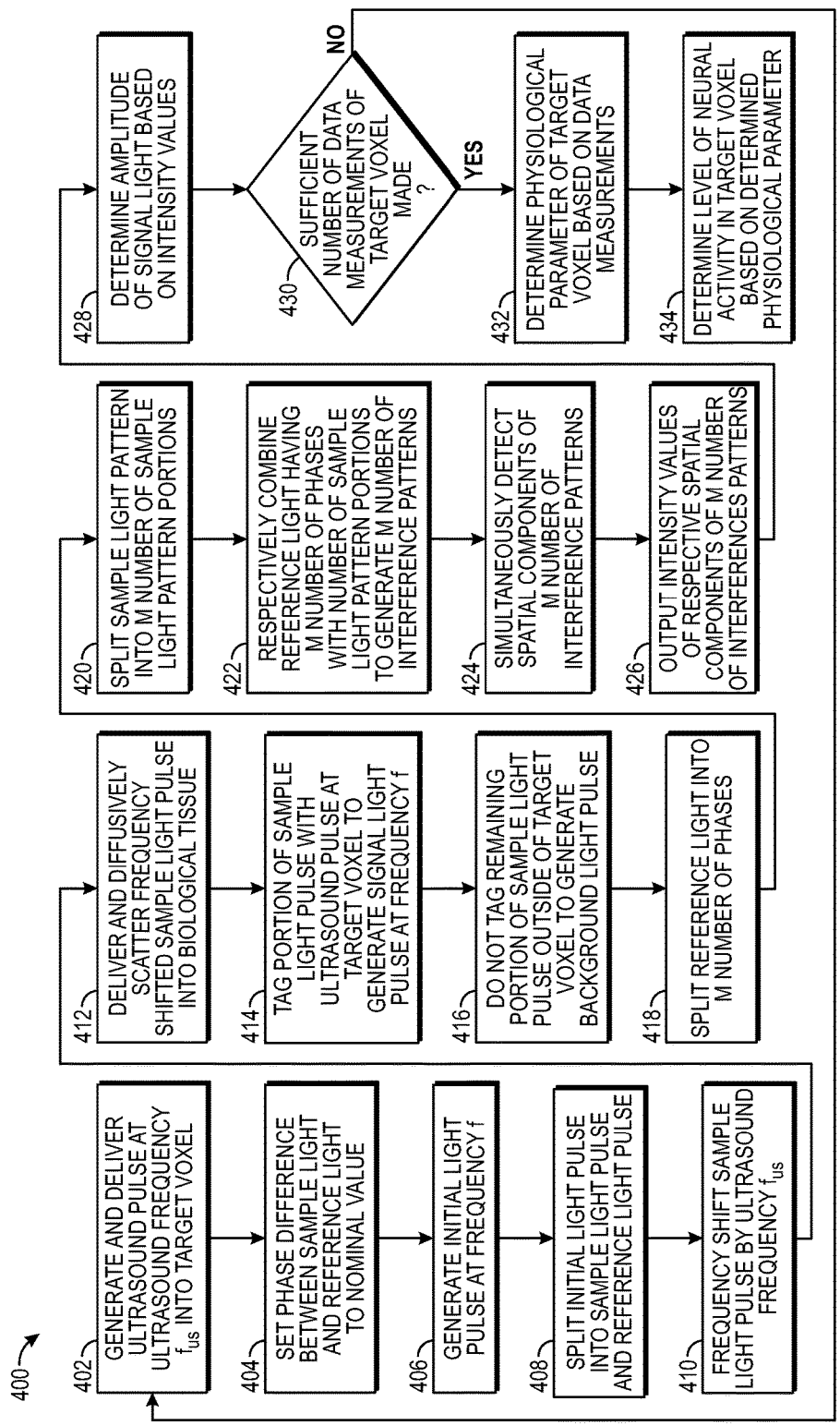
FIG. 31 is a flow diagram of one method used by the UOT system of FIG. 15 to non-invasively measure a physiologically-dependent optical parameter.

Referring to FIG. 31, one particular method 400 performed by the UOT system 210 to non-invasively image the target voxel 14 in anatomical structure 16 will now be described.

The controller 24 operates the acoustic assembly 20 to generate and deliver a pulse of ultrasound 32 having a frequency $f_{us}$ into the anatomical structure 16, e.g., by sending a control signal to the signal generator 36 to pulse an electrical signal on and off (step 402). The controller 24 sets the phase difference between the sample light 40 and the reference light 42 to a nominal value (e.g., 0) (step 404). Next, the controller 24 operates the interferometer 222 to generate and emit a pulse of source light 38 having a frequency f, e.g., by sending a control signal to the drive circuit to pulse the light source 50 on and off (step 406). The interferometer 222 (e.g., via the beam splitter 52) splits the pulse of source light 38 into a pulse of sample light 40 and a pulse of reference light 42 (step 408).

The wavelength (and thus, the frequency f) of the source light 38 may be selected based on the physiologically-dependent optical parameter to be ultimately determined. For example, if the physiologically-dependent optical parameter is the level of deoxygenated and/or oxygenated hemoglobin concentration or relative abundance, the wavelength of the source light 38 may be in the range of 605 nanometers to 950 nanometers, whereas if the physiologically-dependent optical parameter to be determined is a water absorption level (level of water concentration or relative water concentration), the wavelength of the source light 38 may be in the range of 950-1080 nanometers.

Next, prior to the pulse of sample light 40 entering the anatomical structure 16, the controller 24 operates the interferometer 222 to frequency shift the pulse of sample light 40 by the ultrasound frequency $f_{us}$, e.g., by sending a control signal to the frequency shifter 56, resulting in the pulse of sample light 40 having a frequency $f-f_{us}$ (step 410). It should be appreciated that, although this frequency shifting technique implements the frequency shifting technique illustrated in FIG. 3a, other frequency shifting techniques can be utilized, such as those illustrated in FIGS. 3b-3d. The frequency-shifted pulse of sample light 40 is then delivered into and diffusively scattered within the anatomical structure 16 (step 412). As the pulse of frequency shifted sample light 40 scatters diffusively through the anatomical structure 16, a portion will pass through the target voxel 14 and be frequency shifted (i.e., tagged) back to its original frequency f by the pulse of ultrasound 32 passing through the target voxel 14, resulting in a pulse of scattered signal light 44 having the same frequency f (step 414); and remaining portion will not pass through the target voxel 14, and thus will not be frequency shifted by the pulse of ultrasound 32, resulting in a pulse of scattered background light 46 having a frequency $f-f_{us}$ (the same frequency as the frequency shifted sample light 40 prior to entering the anatomical structure 16) (step 416).

Next, the interferometer 222 then concurrently, via the one or more beam splitter/combiners 258, splits the reference light 42 respectively into an M number of different phases (step 418), splits the sample light pattern 47 into an M number of sample light pattern portions (step 420), and respectively combines the sample light pattern portions and the reference light 42 to respectively generate the interference light patterns 48 (step 422).

Then, under control of the controller 24, each of M number of detector arrays 228 simultaneously detect respective spatial components of the corresponding interference light pattern 48 (i.e., speckle grains in the case where the interference light pattern includes a speckle light pattern) (step 424), and output intensity values for the respective spatial components of the N number of interference light patterns 48 (step 426). The processor (e.g., a portion of which may include processing circuitry 306) then determines the amplitude of the signal light 44 based on these intensity values (e.g., using equations [20] or [21] if M equal two, and using equations [26]-[29] if M equals four) (step 428).

Steps 402-428 can be iterated to repeatedly acquire data measurements of the target voxel 14, and if a sufficient number of data measurements have been acquired (step 430), the processor 30 may then determine the physiologically-dependent optical parameter (e.g., level of deoxygenated and/or oxygenated hemoglobin concentration or relative abundance or level of water concentration or relative water concentration) of the target voxel 14 based on the data measurements (step 432). In the case where the target voxel 14 is brain matter, the processor 30 may further determine the level of neural activity within the target voxel 14 based on the determined physiologically-dependent optical parameter (step 434), e.g., in the manner described above with respect to step 134 of the method 100 illustrated in FIG. 13.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A non-invasive optical detection system, comprising:
    an interferometer configured for delivering sample light into the anatomical structure having a target voxel, whereby a portion of the sample light passing through the target voxel is scattered by the anatomical structure as signal light, and another portion of the sample light not passing through the target voxel is scattered by the anatomical structure as background light that is combined with the signal light to create a sample light pattern, the interferometer comprising:
        a single beam splitter configured for splitting the sample light pattern into first and second sample light pattern portions;
        a first beam splitter/combiner configured for splitting the reference light respectively into a first two of four different phases, and concurrently combining the first sample light portion and the reference light having the first two of the four different phases to respectively generate a first two of four interference light patterns; and
        a second beam splitter/combiner configured for splitting the reference light respectively into a second two of the four different phases, and concurrently combining the second sample light pattern portion and the reference light having the second two of the four different phases to respectively generate the second two of the four interference light patterns;
    a camera system having four optically registered detector arrays respectively configured for detecting the four interference light patterns, and generating four pluralities of values representative of spatial components of the respective four interference light patterns; and
    a processor configured for determining a physiologically-dependent optical parameter of the target voxel based on the four pluralities of values.

2. The system of claim 1, wherein the first two of the four different phases and the second two of the four different phases are ninety degrees out of phase with each other.

3. The system of claim 1, wherein the four detector arrays are mechanically disposed on separate camera microchips.

4. The system of claim 1, wherein the four detector arrays are mechanically integrated together on a single camera microchip.

5. The system of claim 4, further comprising processing circuitry integrated within the single camera microchip, the processing circuitry configured for performing an arithmetic function on the four pluralities of values, and outputting at least one value, wherein the processor is configured for determining the physiologically-dependent optical parameter of the target voxel based on the at least one value.

6. The system of claim 5, wherein the function comprises a sum of the absolute differences between corresponding values of the four pluralities of values.

7. The system of claim 4, wherein the interferometer comprises at least one array of beam splitter/combiners integrated within the single camera microchip, the at least one array of beam splitter/combiners configured for splitting the reference light respectively into the four different phases, and concurrently combining the sample light pattern and the reference light having the four different phases to respectively generate the four interference light patterns.

8. The system of claim 7, wherein the four detector arrays are interlaced with each other on the single camera microchip.

9. The system of claim 1, wherein the physiologically-dependent optical parameter is at least one of the level of deoxygenated and/or oxygenated hemoglobin concentration or relative abundance, and the level of water concentration or relative water concentration of brain matter.

10. The system of claim 1, wherein the signal light is frequency encoded.

11. The system of claim 10, further comprising an acoustic assembly configured for delivering ultrasound into the target voxel, such that the signal light is frequency shifted by the ultrasound.

12. The system of claim 11, further comprising a controller configured for operating the acoustic assembly and the interferometer to pulse the ultrasound and the sample light in synchrony, such that only the signal light is frequency shifted by the ultrasound.

13. The system of claim 12, wherein the controller is configured for operating the acoustic assembly and the interferometer to pulse the ultrasound and the sample light in synchrony, such that only a single pulse of the sample light is delivered into the anatomical structure for each pulse of the ultrasound delivered into the target voxel.

14. The system of claim 10, wherein the interferometer is configured for combining the signal light and the reference light in a homodyne manner.

15. The system of claim 14, wherein the interferometer is further configured for frequency shifting the sample light by the frequency of the ultrasound, such that the signal light and the reference light are combined in the homodyne manner.

16. The system of claim 1, wherein the interferometer comprises a light source configured for generating source light, a beam splitter configured for splitting the source light into the sample light and the reference light.

17. The system of claim 1, wherein the processor is configured for computing the amplitude of the signal light using the plurality of values generated by each detector array, and determining the physiologically-dependent optical parameter of the target voxel based on the computed amplitude of the signal light.

18. The system of claim 17, wherein the plurality of values generated by each detector array are intensities of the spatial components of the respective interference light pattern, the processor is configured for using the plurality of values generated by each detector array to determine a product of the amplitude of the signal light and a known amplitude of the reference light, and determining the amplitude of the signal light from the determined product.

19. A non-invasive optical detection method, comprising:
    delivering sample light into an anatomical structure having a target voxel, whereby a portion of the sample light passing through the target voxel is scattered by the anatomical structure as signal light, and another portion of the sample light not passing through the target voxel is scattered by the anatomical structure as background light that is combined with the signal light to create a sample light pattern;

splitting the sample light pattern into first and second sample light pattern portions;

splitting the reference light respectively into a first two of four different phases;

concurrently combining the first sample light portion and the reference light having the first two of the four different phases to respectively generate a first two of four interference light patterns;

splitting the reference light respectively into a second two of the four different phases;

concurrently combining the second sample light pattern portion and the reference light having the second two of the four different phases to respectively generate the second two of the four interference light patterns;

detecting the four interference light patterns;

generating four pluralities of values representative of spatial components of the respective four interference light patterns; and determining a physiologically-dependent optical parameter of the target voxel based on the four pluralities of values.

20. The method of claim 19, further comprising delivering ultrasound into the target voxel, such that the signal light is frequency shifted by the ultrasound.

21. The system of claim 20, further comprising pulsing the ultrasound and the sample light in synchrony, such that only the signal light is frequency shifted by the ultrasound.

22. The method of claim 21, wherein the ultrasound and the sample light are pulsed in synchrony, such that only a single pulse of the sample light is delivered into the anatomical structure for each pulse of the ultrasound delivered into the target voxel.

23. A non-invasive optical detection system, comprising:
a single camera microchip comprising an array of reference input ports and an array of sample input ports;
an interferometer configured for delivering sample light into the anatomical structure having a target voxel, whereby a portion of the sample light passing through the target voxel is scattered by the anatomical structure as signal light, and another portion of the sample light not passing through the target voxel is scattered by the anatomical structure as background light that is combined with the signal light to create a sample light pattern, the interferometer comprising:
a first grate configured for transforming reference light into an array of reference beamlets;
a first lens configured for focusing the array of reference beamlets into the array of reference input ports;
a second grate configured for transforming the sample light pattern into an array of sample light pattern beamlets;
a second lens configured for focusing the array of sample light pattern beamlets into the array of sample input ports; and
at least one array of beam splitter/combiners integrated within the single camera microchip, the at least one array of beam splitter/combiners configured for splitting the array of reference beamlets respectively into an M number of different phases relative to the sample light pattern, and concurrently combining the array of sample light pattern beamlets and the array of reference beamlets having the M number of different phases to respectively generate an M number of interference light patterns;
a camera system having an M number of optically registered detector arrays mechanically integrated together on the single camera microchip, the M number of optically registered detector arrays respectively configured for detecting the M number of interference light patterns, and generating M pluralities of values representative of spatial components of the respective M number of interference light patterns; and
a processor configured for determining a physiologically-dependent optical parameter of the target voxel based on the M pluralities of values.

24. The system of claim 23, further comprising processing circuitry integrated within the single camera microchip, the processing circuitry configured for performing an arithmetic function on the M pluralities of values, and outputting at least one value, wherein the processor is configured for determining the physiologically-dependent optical parameter of the target voxel based on the at least one value.

25. The system of claim 24, wherein the function comprises a sum of the absolute differences between corresponding values of the M pluralities of values.

26. The system of claim 23, wherein M equals two, and the two detector arrays are respectively mechanically integrated on opposite sides of the single camera microchip.

27. The system of claim 23, wherein the interferometer comprises at least one array of beam splitter/combiners integrated within the single camera microchip, the at least one array of beam splitter/combiners configured for splitting the reference light respectively into the M number of different phases, and concurrently combining the sample light pattern and the reference light having the M number of different phases to respectively generate the M number of interference light patterns.

28. The system of claim 27, wherein the M number of detector arrays are interlaced with each other on the single camera microchip.

29. The system of claim 23, further comprising an acoustic assembly configured for delivering ultrasound into the target voxel, such that the signal light is frequency shifted by the ultrasound.

30. The system of claim 29, further comprising a controller configured for operating the acoustic assembly and the interferometer to pulse the ultrasound and the sample light in synchrony, such that only the signal light is frequency shifted by the ultrasound.

* * * * *